United States Patent
Hanon et al.

(10) Patent No.: US 10,555,999 B2
(45) Date of Patent: *Feb. 11, 2020

(54) INFLUENZA VACCINE

(71) Applicant: GLAXOSMITHKLINE BIOLOGICALS S.A., Rixensart (BE)

(72) Inventors: Emmanuel Jules Hanon, Rixensart (BE); Jean Stephenne, Rixensart (BE)

(73) Assignee: GLAXOSMITHKLINE BIOLOGICASL SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/920,519

(22) Filed: Mar. 14, 2018

(65) Prior Publication Data

US 2019/0054162 A1  Feb. 21, 2019

Related U.S. Application Data

(63) Continuation of application No. 14/996,446, filed on Jan. 15, 2016, now Pat. No. 9,943,588, which is a continuation of application No. 13/163,002, filed on Jun. 17, 2011, now Pat. No. 9,278,127, which is a continuation of application No. 11/692,792, filed on Mar. 28, 2007, now abandoned.

(60) Provisional application No. 60/831,437, filed on Jul. 17, 2006.

(30) Foreign Application Priority Data

| Sep. 15, 2006 | (GB) | 0618195.2 |
| Sep. 27, 2006 | (GB) | 0619090.4 |
| Oct. 27, 2006 | (WO) | PCT/EP2006/010439 |
| Nov. 21, 2006 | (GB) | 0623218.5 |
| Nov. 29, 2006 | (GB) | 0623865.3 |
| Dec. 20, 2006 | (GB) | 0625453.6 |

(51) Int. Cl.
| *A61K 39/145* | (2006.01) |
| *A61K 39/12* | (2006.01) |
| *A61K 39/39* | (2006.01) |
| *C12N 7/00* | (2006.01) |
| *A61K 39/00* | (2006.01) |

(52) U.S. Cl.
CPC ............ *A61K 39/145* (2013.01); *A61K 39/12* (2013.01); *A61K 39/39* (2013.01); *C12N 7/00* (2013.01); *A61K 2039/5252* (2013.01); *A61K 2039/545* (2013.01); *A61K 2039/55566* (2013.01); *A61K 2039/572* (2013.01); *A61K 2039/575* (2013.01); *C12N 2760/16134* (2013.01); *C12N 2760/16171* (2013.01); *C12N 2760/16234* (2013.01)

(58) Field of Classification Search
None
See application file for complete search history.

(56) References Cited

U.S. PATENT DOCUMENTS 9,278,127 B2 * 3/2016 Hanon ................. A61K 39/145
9,943,588 B2 * 4/2018 Hanon ................. A61K 39/145

FOREIGN PATENT DOCUMENTS

WO   WO-2001-022992   *  4/2001

OTHER PUBLICATIONS

CDC Avian influenza (Bird Flu) fact sheet, 2005.*
Bardiya and Bae, Influenza vaccines: recent advances in production technologies, 2005, Applied Microbiol Biotechnology, vol. 67, pp. 299-305.*
Stephenson et al., Confronting the avian influenza threat: vaccine development fora potential pandemic, 2004, Lancet Infect Dis, vol. 4, pp. 499-509.*

* cited by examiner

*Primary Examiner* — Benjamin P Blumel

(57) ABSTRACT

The present invention relates to monovalent influenza vaccine formulations and vaccination regimes for immunising against influenza disease, their use in medicine, in particular their use in augmenting immune responses to various antigens, and to methods of preparation. In particular, the invention relates to monovalent influenza immunogenic compositions comprising an influenza antigen or antigenic preparation thereof from an influenza virus strain being associated with a pandemic outbreak or having the potential to be associated with a pandemic outbreak, in combination with an oil-in-water emulsion adjuvant comprising a metabolisable oil, a sterol and/or a tocopherol such as alpha tocopherol, and an emulsifying agent.

21 Claims, 20 Drawing Sheets

Figure 1B:
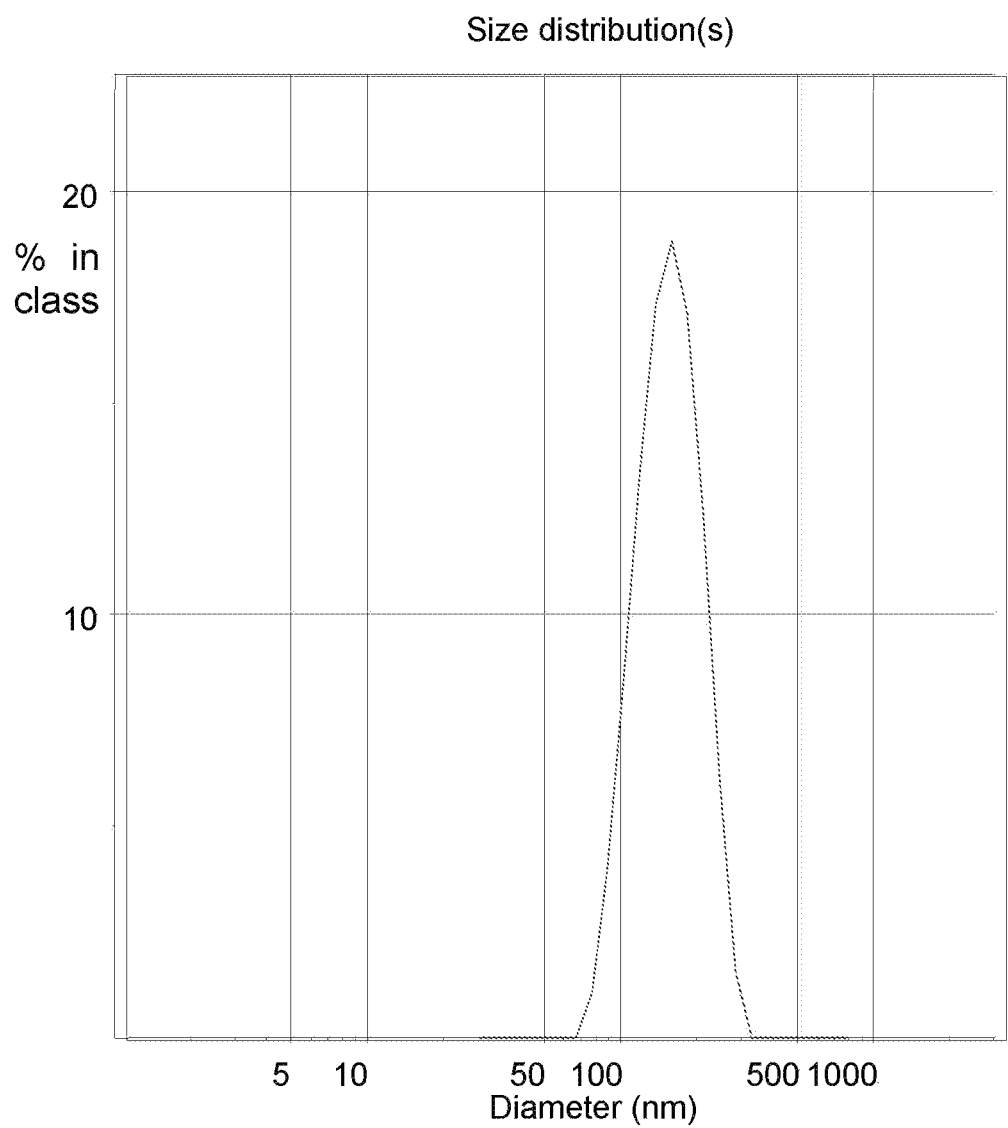

FIG.1A
Dilution A
Rec22

| Size(nm) | Intensity | Volume |
|---|---|---|
| 27.9 | 0.0 | 0.0 |
| 32.2 | 0.0 | 0.0 |
| 37.3 | 0.0 | 0.0 |
| 43.1 | 0.0 | 0.0 |
| 49.8 | 0.0 | 0.0 |
| 57.6 | 0.0 | 0.0 |
| 66.6 | 0.0 | 1.1 |
| 77.0 | 1.0 | 4.8 |
| 89.1 | 4.0 | 10.3 |
| 103.0 | 8.4 | 14.7 |
| 119.1 | 13.3 | 16.6 |
| 137.7 | 17.3 | 15.9 |
| 159.3 | 18.8 | 13.4 |
| 184.2 | 17.1 | 10.2 |
| 212.9 | 12.3 | 7.0 |
| 246.2 | 6.2 | 4.0 |
| 284.7 | 1.5 | 1.7 |
| 329.2 | 0.0 | 0.4 |
| 380.6 | 0.0 | 0.0 |
| 440.1 | 0.0 | 0.0 |
| 508.9 | 0.0 | 0.0 |
| 588.5 | 0.0 | 0.0 |
| 680.4 | 0.0 | 0.0 |
| 786.8 | 0.0 | 0.0 |

| Peak Analysis by intensity | | | |
|---|---|---|---|
| Peak | Area | Mean | Width |
| 1 | 100.0 | 160.0 | 122.3 |

| Peak Analysis by volume | | | |
|---|---|---|---|
| Peak | Area | Mean | Width |
| 1 | 100.0 | 141.3 | 116.6 |

| Peak Analysis by number | | | |
|---|---|---|---|
| Peak | Area | Mean | Width |
| 1 | 100.0 | 109.8 | 62.5 |

Rec23

| Size(nm) | Intensity | Volume |
|---|---|---|
| 23.0 | 0.0 | 0.0 |
| 27.0 | 0.0 | 0.0 |
| 31.7 | 0.0 | 0.0 |
| 37.3 | 0.0 | 0.0 |
| 43.9 | 0.0 | 0.0 |
| 51.5 | 0.0 | 0.0 |
| 60.6 | 0.0 | 1.2 |
| 71.2 | 1.1 | 5.3 |
| 83.7 | 3.8 | 10.9 |
| 98.4 | 8.0 | 15.0 |
| 115.6 | 13.0 | 16.4 |
| 135.9 | 17.2 | 15.4 |
| 159.7 | 19.2 | 12.9 |
| 187.7 | 17.7 | 9.9 |
| 220.7 | 12.8 | 6.9 |
| 259.4 | 6.1 | 4.1 |
| 304.8 | 1.2 | 1.8 |
| 358.3 | 0.0 | 0.4 |
| 421.1 | 0.0 | 0.0 |
| 495.0 | 0.0 | 0.0 |
| 581.8 | 0.0 | 0.0 |
| 683.8 | 0.0 | 0.0 |
| 803.7 | 0.0 | 0.0 |
| 944.6 | 0.0 | 0.0 |

| Peak Analysis by intensity | | | |
|---|---|---|---|
| Peak | Area | Mean | Width |
| 1 | 100.0 | 161.7 | 135.3 |

| Peak Analysis by volume | | | |
|---|---|---|---|
| Peak | Area | Mean | Width |
| 1 | 100.0 | 139.8 | 128.6 |

| Peak Analysis by number | | | |
|---|---|---|---|
| Peak | Area | Mean | Width |
| 1 | 100.0 | 102.0 | 59.8 |

FIG. 1A cont'd.
Rec24

| Size(nm) | Intensity | Volume |
|---|---|---|
| 20.2 | 0.0 | 0.0 |
| 24.0 | 0.0 | 0.0 |
| 28.6 | 0.0 | 0.0 |
| 34.0 | 0.0 | 0.0 |
| 40.4 | 0.0 | 0.0 |
| 48.0 | 0.0 | 0.0 |
| 57.1 | 0.0 | 0.5 |
| 67.9 | 0.4 | 3.5 |
| 80.7 | 2.9 | 9.5 |
| 95.9 | 7.6 | 15.4 |
| 114.0 | 13.7 | 18.1 |
| 135.6 | 19.2 | 17.4 |
| 161.2 | 21.3 | 14.4 |
| 191.7 | 18.9 | 10.6 |
| 227.9 | 12.0 | 6.7 |
| 271.0 | 3.9 | 3.2 |
| 322.2 | 0.0 | 0.8 |
| 383.1 | 0.0 | 0.0 |
| 455.5 | 0.0 | 0.0 |
| 541.5 | 0.0 | 0.0 |
| 643.9 | 0.0 | 0.0 |
| 765.5 | 0.0 | 0.0 |
| 910.2 | 0.0 | 0.0 |
| 1082.2 | 0.0 | 0.0 |

Peak Analysis by intensity

| Peak | Area | Mean | Width |
|---|---|---|---|
| 1 | 100.0 | 160.2 | 130.1 |

Peak Analysis by volume

| Peak | Area | Mean | Width |
|---|---|---|---|
| 1 | 100.0 | 139.1 | 126.2 |

Peak Analysis by number

| Peak | Area | Mean | Width |
|---|---|---|---|
| 1 | 100.0 | 104.2 | 63.0 |

Dilution B
Rec28

| Size(nm) | Intensity | Volume |
|---|---|---|
| 22.2 | 0.0 | 4.1 |
| 26.2 | 0.2 | 9.7 |
| 30.9 | 0.1 | 7.1 |
| 36.4 | 0.0 | 1.5 |
| 42.9 | 0.0 | 0.0 |
| 50.5 | 0.0 | 0.0 |
| 59.6 | 0.0 | 0.0 |
| 70.2 | 0.0 | 1.2 |
| 82.7 | 1.8 | 5.1 |
| 97.5 | 6.2 | 10.4 |
| 114.9 | 13.1 | 14.3 |
| 135.5 | 20.1 | 15.3 |
| 159.7 | 23.5 | 13.4 |
| 188.2 | 20.9 | 9.9 |
| 221.8 | 12.0 | 5.6 |
| 261.4 | 2.1 | 2.0 |
| 308.1 | 0.0 | 0.3 |
| 363.2 | 0.0 | 0.0 |
| 428.1 | 0.0 | 0.0 |
| 504.5 | 0.0 | 0.0 |
| 594.6 | 0.0 | 0.0 |
| 700.9 | 0.0 | 0.0 |
| 826.1 | 0.0 | 0.0 |
| 973.6 | 0.0 | 0.0 |

Peak Analysis by intensity

| Peak | Area | Mean | Width |
|---|---|---|---|
| 1 | 99.7 | 159.3 | 111.5 |

Peak Analysis by volume

| Peak | Area | Mean | Width |
|---|---|---|---|
| 1 | 22.5 | 27.6 | 10.3 |
| 2 | 77.5 | 143.3 | 116.1 |

Peak Analysis by number

| Peak | Area | Mean | Width |
|---|---|---|---|
| 1 | 96.4 | 27.2 | 9.8 |
| 2 | 3.6 | 115.4 | 68.8 |

FIG. 1A cont'd.
Rec29

| Size(nm) | Intensity | Volume |
|---|---|---|
| 28.1 | 0.0 | 0.0 |
| 32.5 | 0.0 | 0.0 |
| 37.6 | 0.0 | 0.0 |
| 43.4 | 0.0 | 0.0 |
| 50.2 | 0.0 | 0.0 |
| 58.1 | 0.0 | 0.3 |
| 67.1 | 0.2 | 2.1 |
| 77.6 | 1.5 | 5.9 |
| 89.7 | 4.2 | 10.6 |
| 103.7 | 8.3 | 14.2 |
| 119.9 | 12.8 | 15.6 |
| 138.6 | 16.6 | 14.9 |
| 160.2 | 18.3 | 12.8 |
| 185.2 | 17.0 | 10.0 |
| 214.1 | 12.6 | 7.0 |
| 247.6 | 6.7 | 4.3 |
| 286.2 | 1.9 | 2.0 |
| 330.9 | 0.0 | 0.5 |
| 382.5 | 0.0 | 0.0 |
| 442.2 | 0.0 | 0.0 |
| 511.2 | 0.0 | 0.0 |
| 591.0 | 0.0 | 0.0 |
| 683.2 | 0.0 | 0.0 |
| 789.8 | 0.0 | 0.0 |

Peak Analysis by intensity

| Peak | Area | Mean | Width |
|---|---|---|---|
| 1 | 100.0 | 161.7 | 127.0 |

Peak Analysis by volume

| Peak | Area | Mean | Width |
|---|---|---|---|
| 1 | 100.0 | 141.4 | 124.5 |

Peak Analysis by number

| Peak | Area | Mean | Width |
|---|---|---|---|
| 1 | 100.0 | 105.8 | 62.6 |

Rec30

| Size(nm) | Intensity | Volume |
|---|---|---|
| 29.1 | 0.0 | 0.0 |
| 33.5 | 0.0 | 0.0 |
| 38.6 | 0.0 | 0.0 |
| 44.4 | 0.0 | 0.0 |
| 51.2 | 0.0 | 0.0 |
| 58.9 | 0.0 | 0.3 |
| 67.9 | 0.2 | 2.1 |
| 78.2 | 1.5 | 6.0 |
| 90.1 | 4.3 | 10.7 |
| 103.7 | 8.3 | 14.2 |
| 119.5 | 12.8 | 15.6 |
| 137.6 | 16.5 | 14.9 |
| 158.5 | 18.1 | 12.8 |
| 182.6 | 16.9 | 10.0 |
| 210.3 | 12.6 | 7.0 |
| 242.3 | 6.8 | 4.2 |
| 279.1 | 2.0 | 1.9 |
| 321.5 | 0.0 | 0.4 |
| 370.3 | 0.0 | 0.0 |
| 426.5 | 0.0 | 0.0 |
| 491.3 | 0.0 | 0.0 |
| 565.9 | 0.0 | 0.0 |
| 651.8 | 0.0 | 0.0 |
| 750.8 | 0.0 | 0.0 |

Peak Analysis by intensity

| Peak | Area | Mean | Width |
|---|---|---|---|
| 1 | 100.0 | 159.8 | 123.3 |

Peak Analysis by volume

| Peak | Area | Mean | Width |
|---|---|---|---|
| 1 | 100.0 | 139.6 | 119.8 |

Peak Analysis by number

| Peak | Area | Mean | Width |
|---|---|---|---|
| 1 | 100.0 | 106.0 | 62.1 |

Record 22, intensity

Record 23, intensity

Fig. 2A    Hemagglutination Inhibition test (GMT) in ferrets immunized with different doses of H5N1 A/Vietnam Anti-A/Vietnam H5N1 - HI titers

| | PBS | H5N1-AS03 (15 µg) | H5N1-AS03 (5 µg) | H5N1-AS03 (1.7 µg) | H5N1-AS03 (0.6 µg) | AS03 alone |
|---|---|---|---|---|---|---|
| ■ D21 | 4 | 12 | 6 | 4 | 7 | 4 |
| ▦ D42 | 4 | 161 | 192 | 60 | 40 | 4 |

Y-axis: HI titers (GMT+/-IC95)

Fig. 2B  Mean H5N1 PCR data (upper graph A) and mean virus titration data (lower graph B) of lung tissues from ferrets challenged with homologous H5N1 viruses Upper graph - A

A - H5N1 PCR Lung Tissue y-axis: log (CDU/g), range 1.00 – 8.00

| Group | Approx. value |
|---|---|
| PBS | ~6.9 |
| AS03 alone | ~6.5 |
| H5N1-AS03 (15 µg) | ~2.8 |
| H5N1-AS03 (5 µg) | ~3.1 |
| H5N1-AS03 (1.7 µg) | ~2.8 |
| H5N1-AS03 (0.7 µg) | ~4.6 |

Lower graph - B

B - H5N1 Virus Titration Lung Tissue y-axis: log (TCID50/g Tissue), range 1.00 – 8.00

| Group | Approx. value |
|---|---|
| PBS | ~6.8 |
| AS03 alone | ~6.3 |
| H5N1-AS03 (15 µg) | ~2.1 |
| H5N1-AS03 (5 µg) | ~2.7 |
| H5N1-AS03 (1.7 µg) | ~2.5 |
| H5N1-AS03 (0.7 µg) | ~3.5 |

FIG. 3    Anti-A/Vietnam neutralizing antibody responses in ferrets immunized with different doses of H5N1 A/Vietnam

| | PBS | H5N1-AS03 (15 µg) | H5N1-AS03 (5 µg) | H5N1-AS03 (1.7 µg) | H5N1-AS03 (0.6 µg) | AS03 alone |
|---|---|---|---|---|---|---|
| ☐ Post-I immunization | 14 | 24 | 14 | 20 | 24 | 14 |
| ■ Post-II immunization | 14 | 113 | 226 | 320 | 118 | 14 | anti-A/Vietnam neutralizing titers (GMT)

FIG. 4   Overview of the manufacture of influenza monovalent bulks

| Step | Manufacturing Step | |
|---|---|---|
| | Preparation of inoculum | |
| | ↓ | |
| | Inoculation of eggs | |
| | ↓ | |
| | Incubation | |
| | ↓ | |
| | Inspection/Harvest | |
| | ↓ | |
| 1 | Crude Monovalent Whole Virus bulk | |
| | ↓ | |
| 2 | Clarification | |
| | ↓ | |
| 3/2 | Adsorption | |
| | ↓ | |
| 3/3 | Filtration to 6 μm | |
| | ↓ | |
| 4 | Flow through ultracentrifugation | |
| | ↓ | |
| 4/2 + 4/3 | Fraction selection | |
| | ↓ | |
| | Fraction 4/3 | Fraction 4/2 |
| | ↓ | ↓ |
| 5/1-5/3 | Ultrafiltration+Centrifugation | |
| | ↓ | |
| | Fraction 4/3 + Fraction 4/2 | |
| | ↓ | |
| 6 | Purified Monovalent Whole Virus Bulk | |
| | ↓ | |
| 7 | Flow through ultracentrifugation<br>Virus splitting in sodium deoxycholate | |
| | ↓ | |
| 7/2 | Fraction selection (Fraction 7/2) | |
| | ↓ | |
| 8/1 | Purified Monovalent Split Virus Bulk | |
| | ↓ | |
| 8/2 + 8/3 | Gradual filtration + Filtration 0.2 μm | |
| | ↓ | |
| | Sodium deoxycholate inactivation | |
| | ↓ | |
| 8/4 | Formaldehyde inactivation | |
| | ↓ | |
| 8/5 + 8/6 | Ultrafiltration | |
| | ↓ | |
| 8/7 + 9 | Gradual filtration + Sterile filtration | |
| | ↓ | |
| | Purified Monovalent Inactivated, Sterile Split Virus Bulk (Monovalent Bulk) | |

FIG. 5    Formulation flow sheet for final bulk of antigen
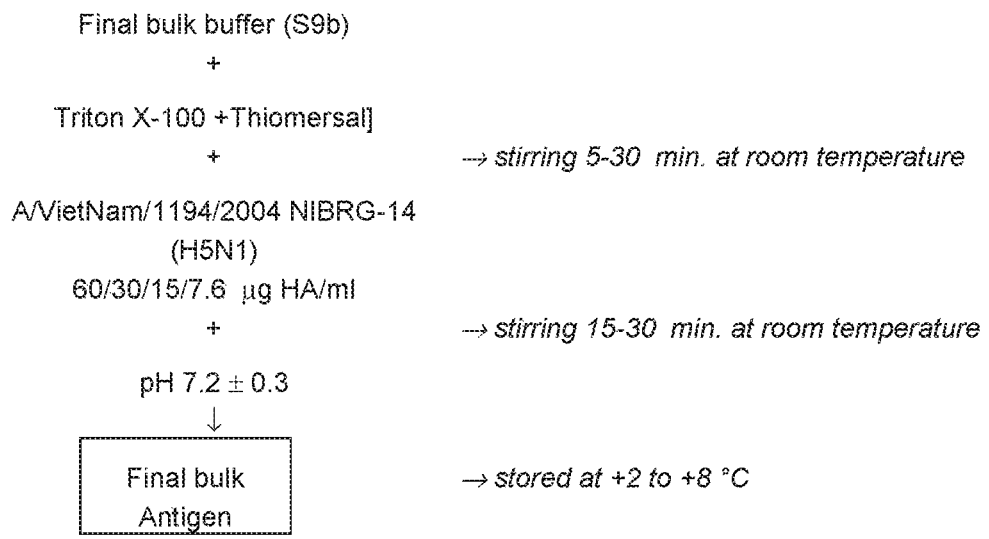
FIG. 6    Human clinical trial: GMT's (with 95%CI) for anti-HA antibody at time-points days 0, 21 and 42
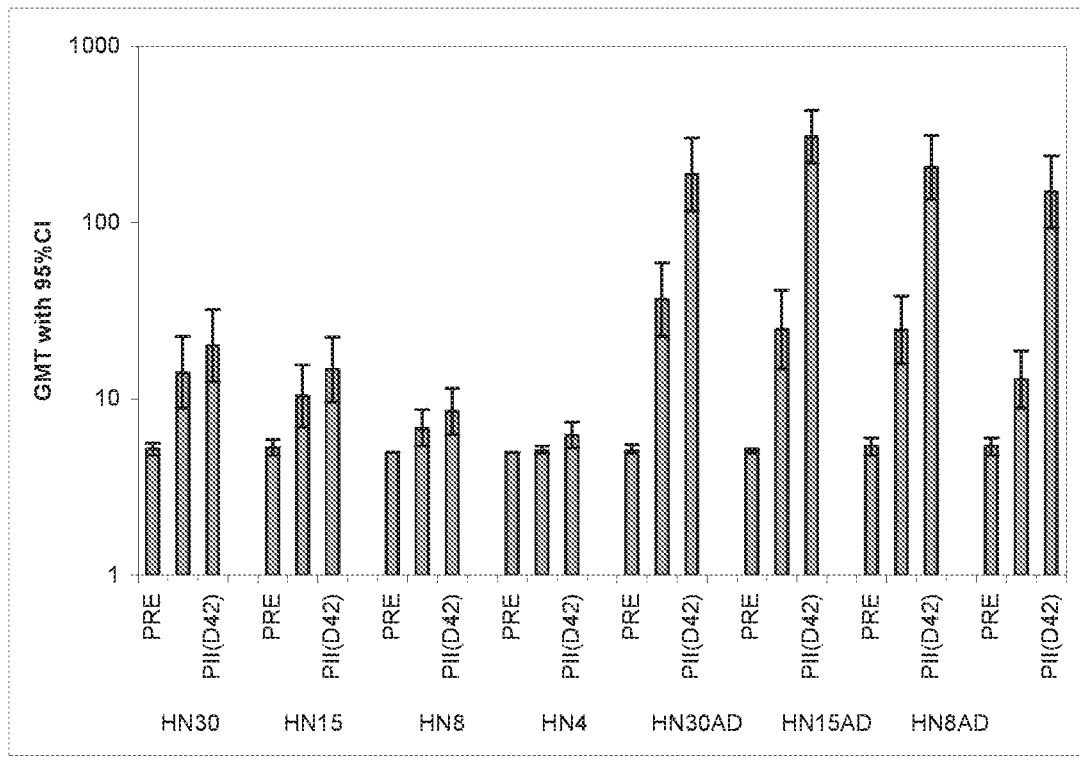

FIG. 7   Seroconversion rates (with 95%CI) for anti-HA antibody at post-vaccination day 21 and day 42
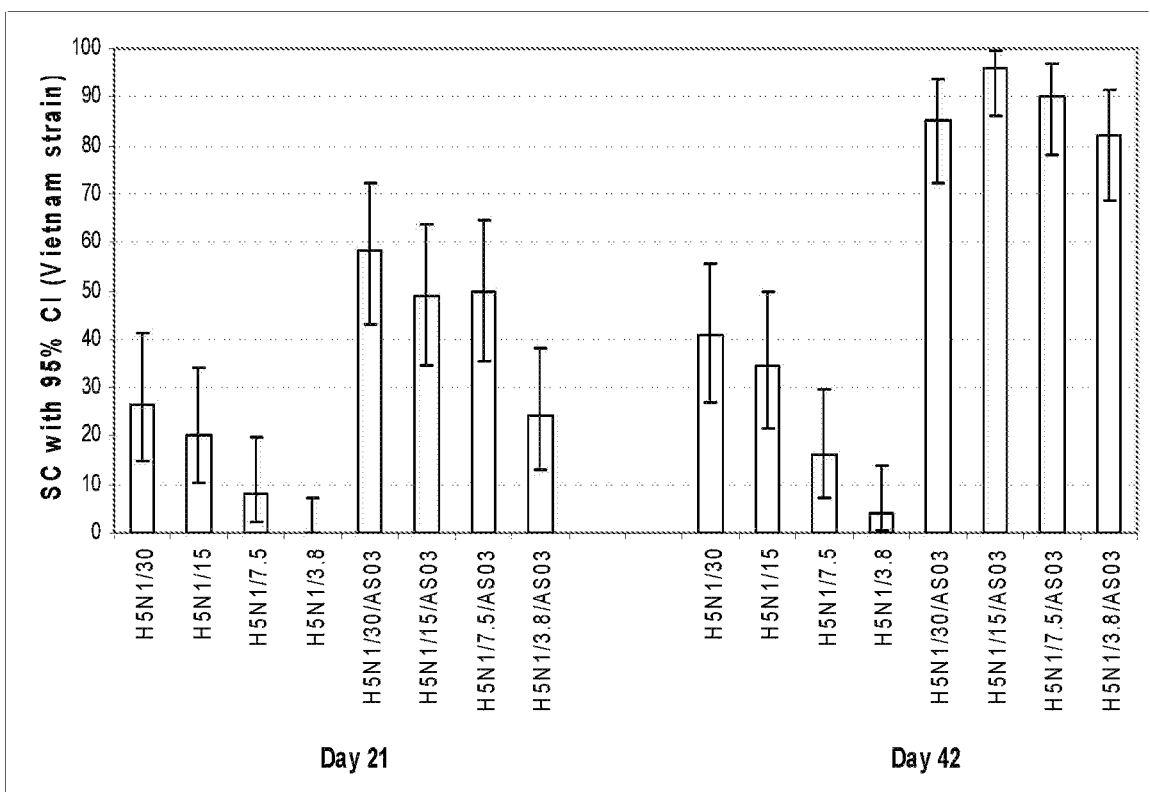

FIG. 8    Seroprotection rates (with 95%CI) for anti-HA antibody at each time-points (Day 0, Day 21 and (Day 42)
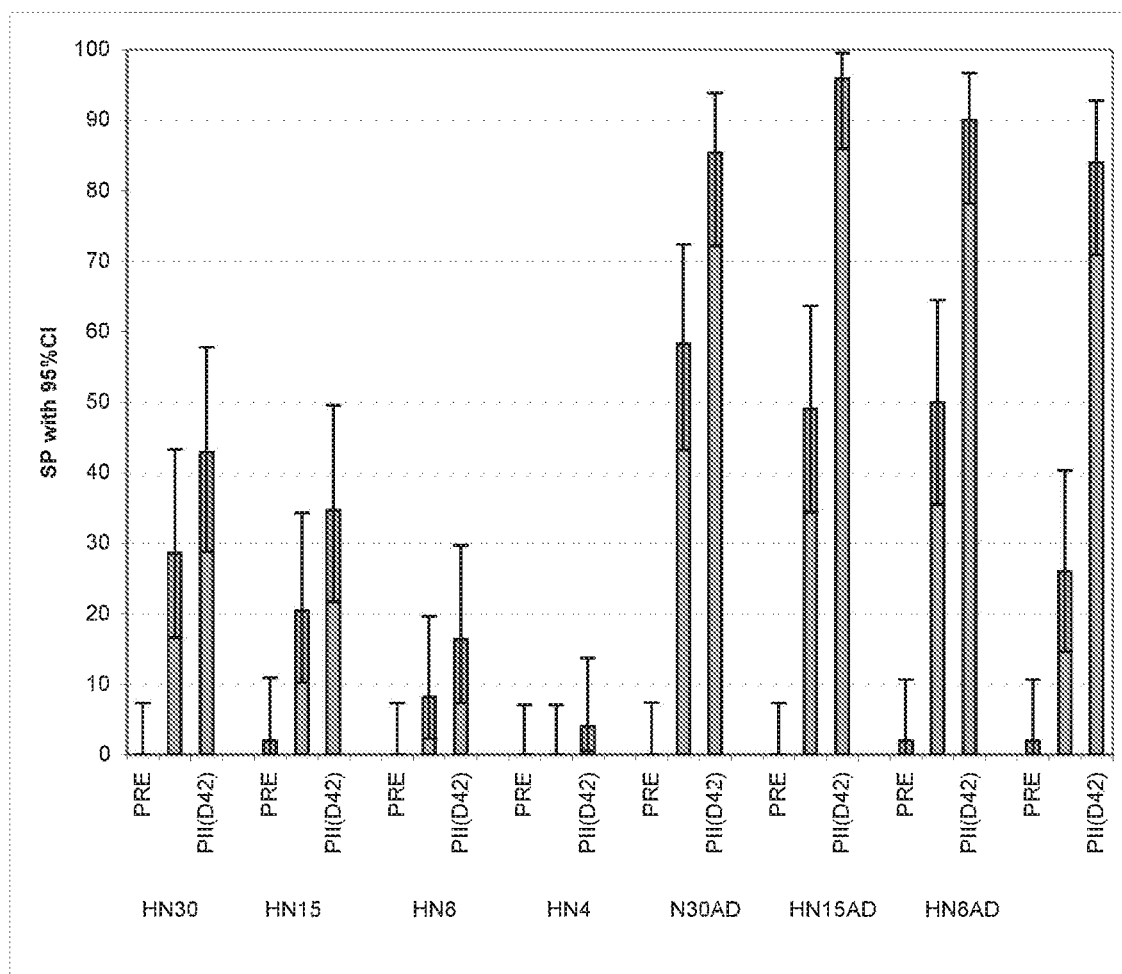

FIG. 9    Seroconversion factors (with 95%CI) for anti-HA antibody at each time-points (Day 0, Day 21 and Day 42)
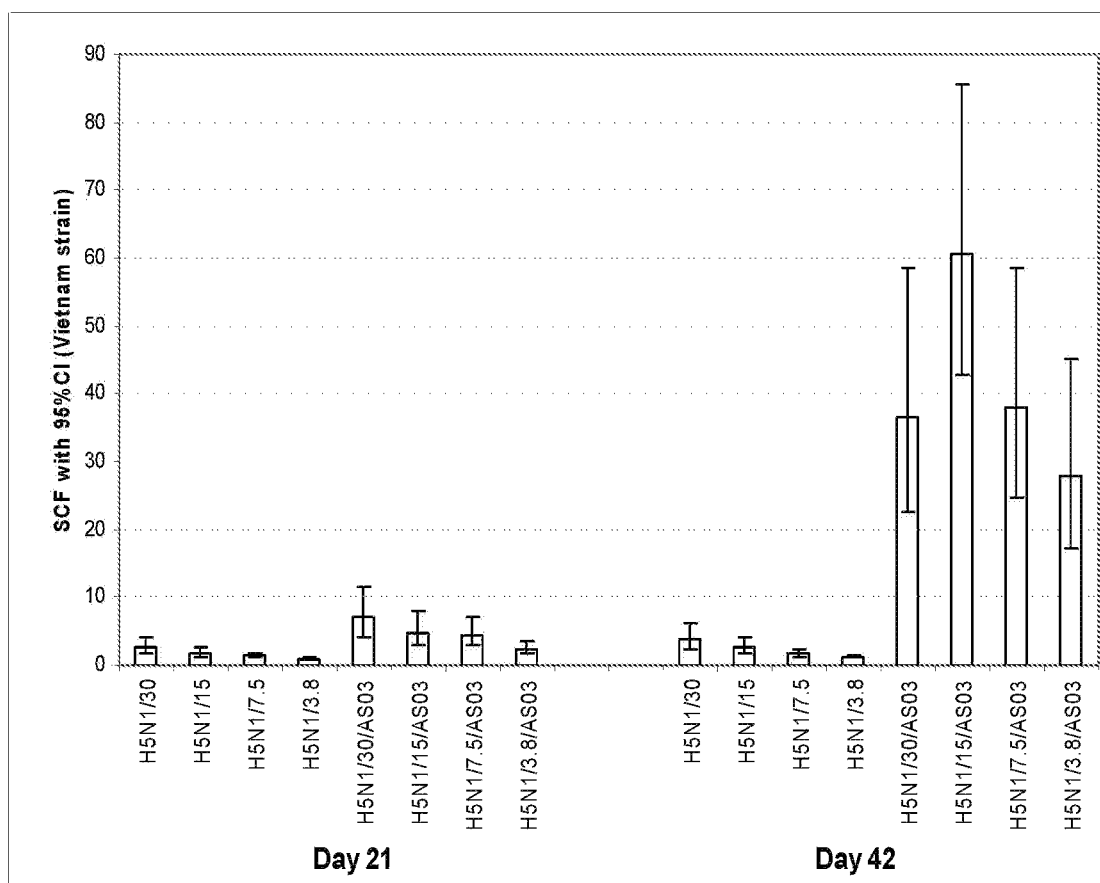

Figure 1B:
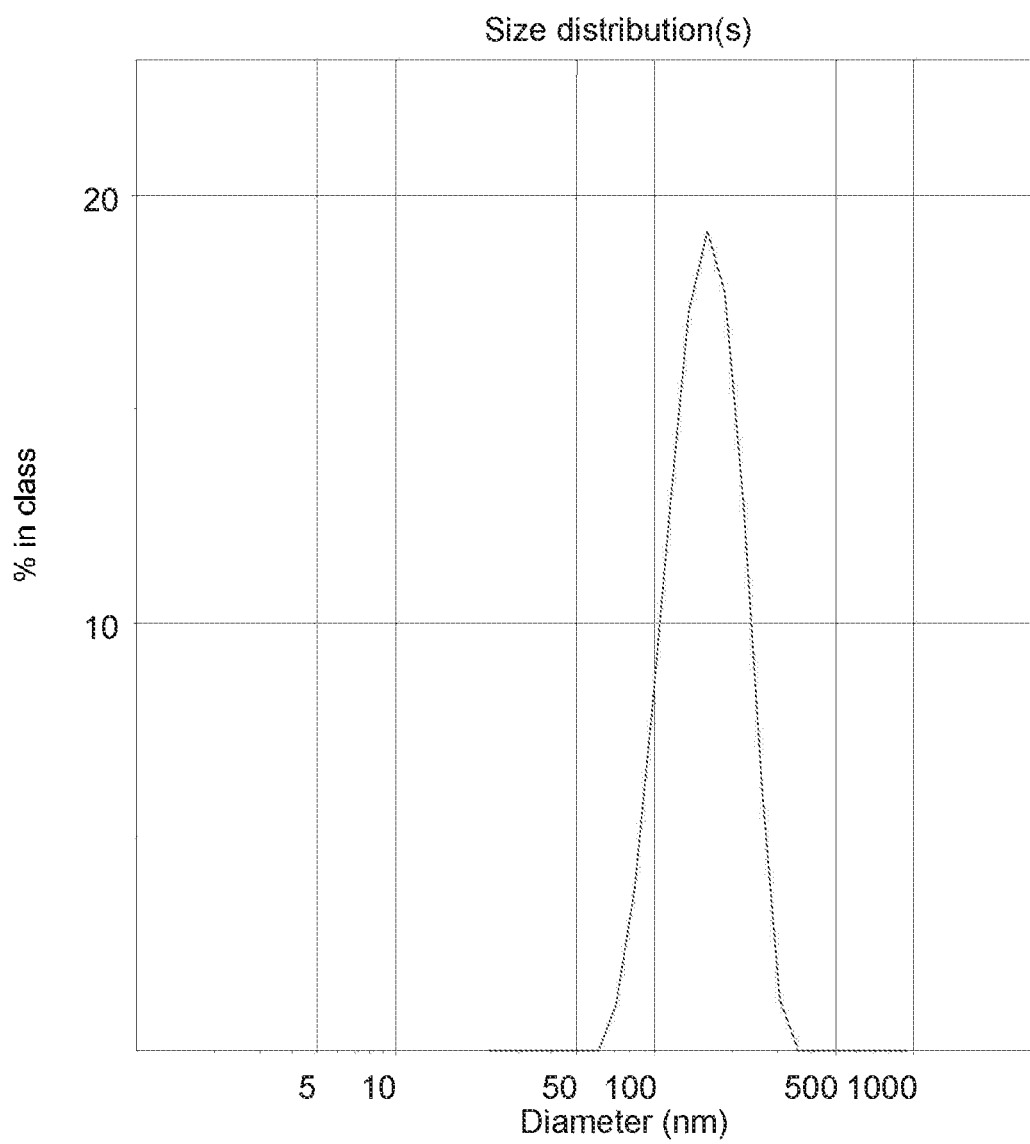

FIG. 10   GMT (with 95%CI) for the Neutralizing antibodies against the vaccine strain (Vietnam strain) (ATP cohort for Immunogenicity)
Fig. 10A1: partial analysis
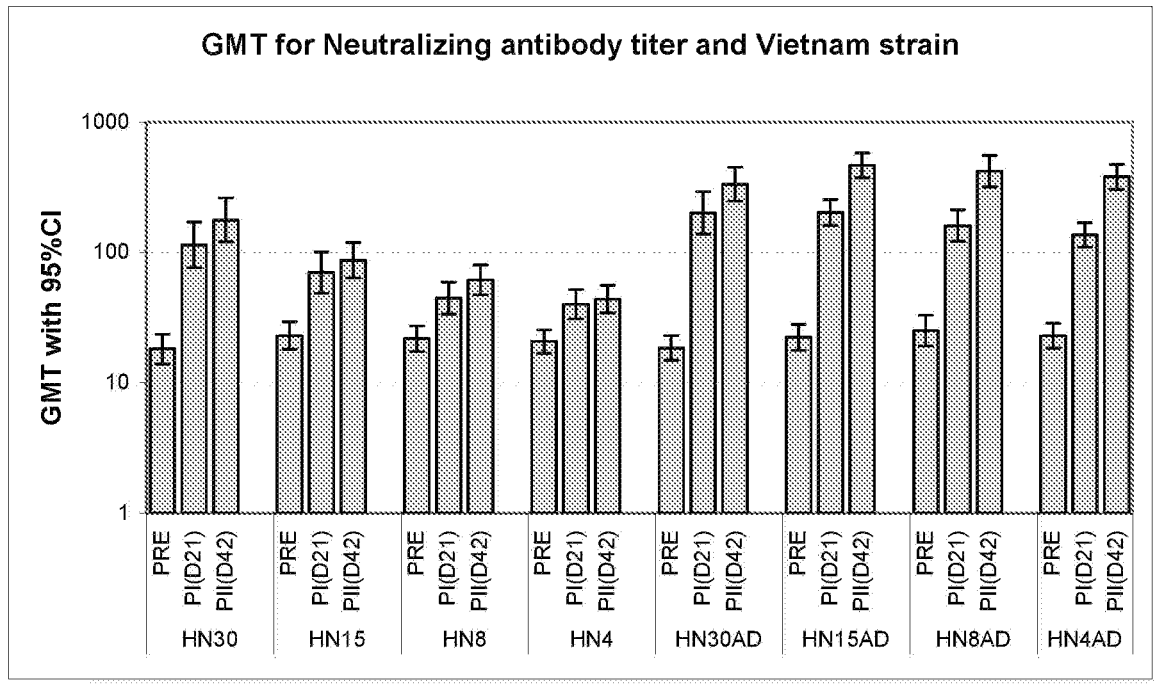
Fig. 10A2: total analysis
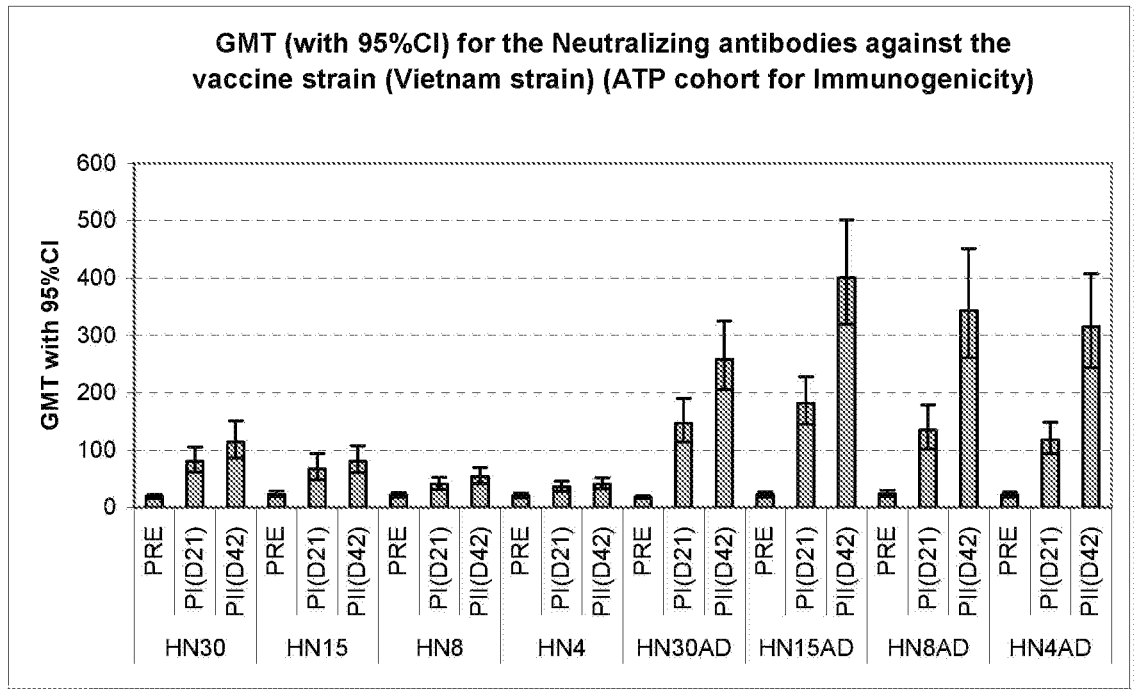

Fig. 10B    Seroconversion rates (SC with 95%CI) for the neutralizing antibodies against the vaccine strain (Vietnam strain) (ATP cohort for immunogenicity)
Fig. 10B1: partial analysis
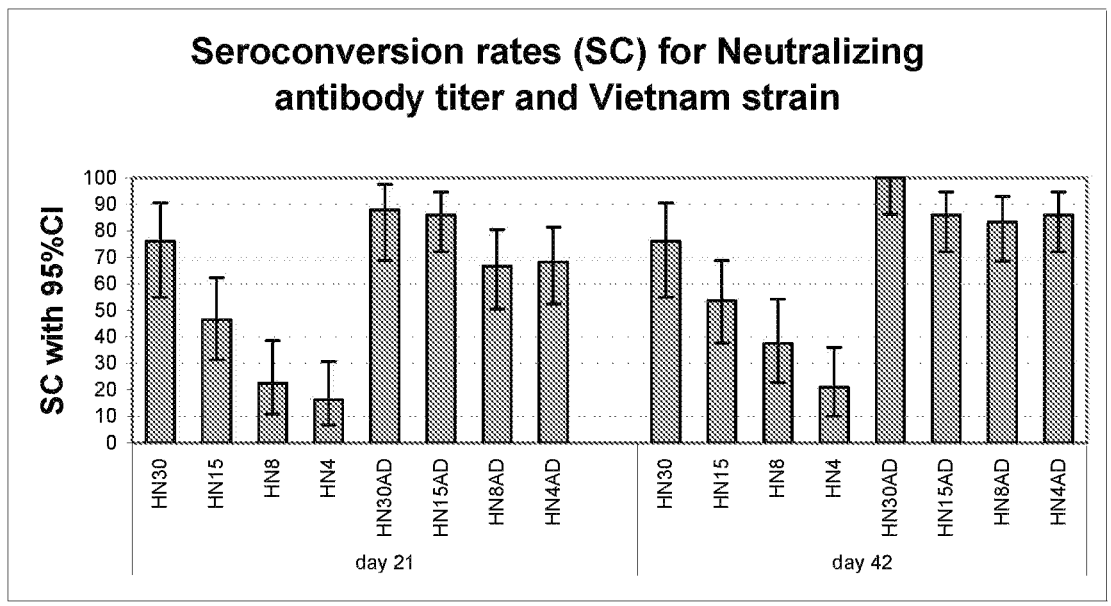
Fig. 10B2: total analysis
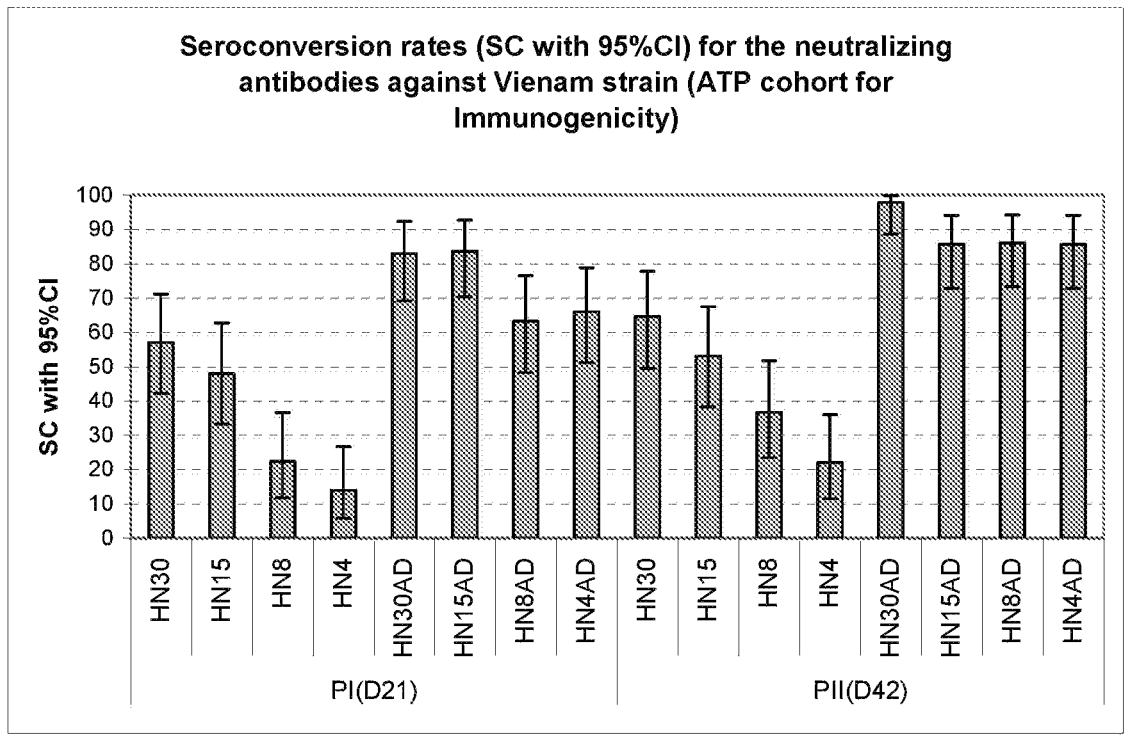

Fig. 10C    GMT (with 95%CI) for the neutralizing antibodies against Indonesia strain (ATP cohort immunogenicity)
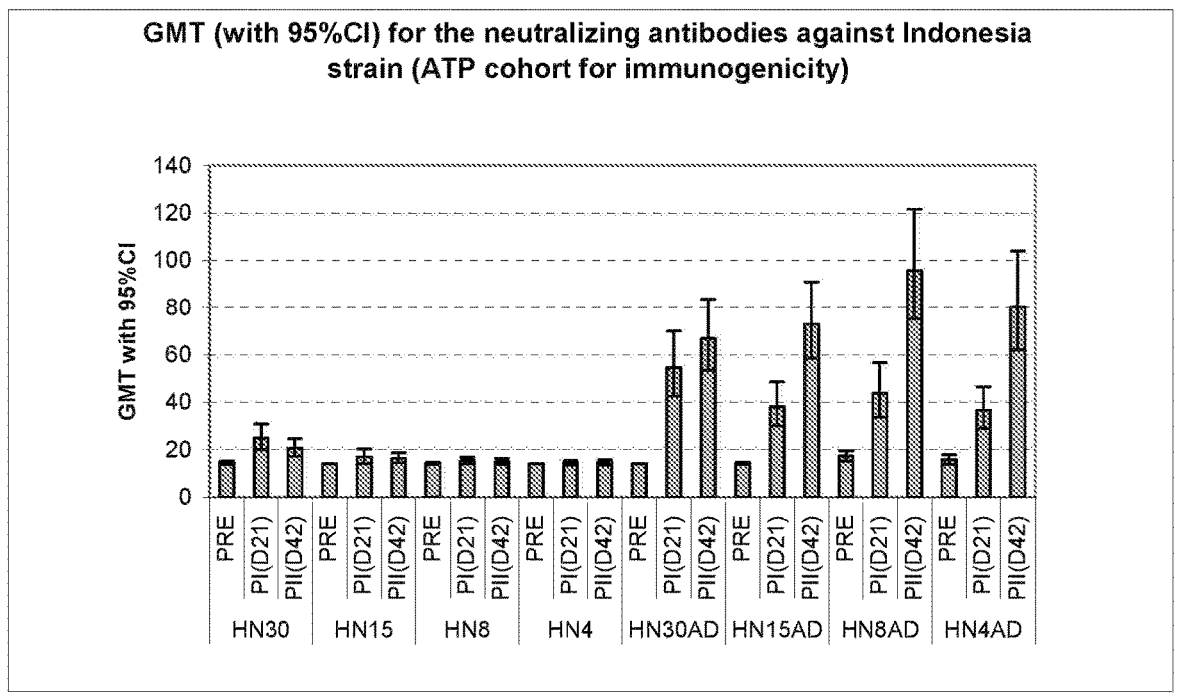
Fig. 10D    Seroconversion rates (with 95%CI) for the neutralizing antibodies against Indonesia strain (ATP cohort for immunogenicity)
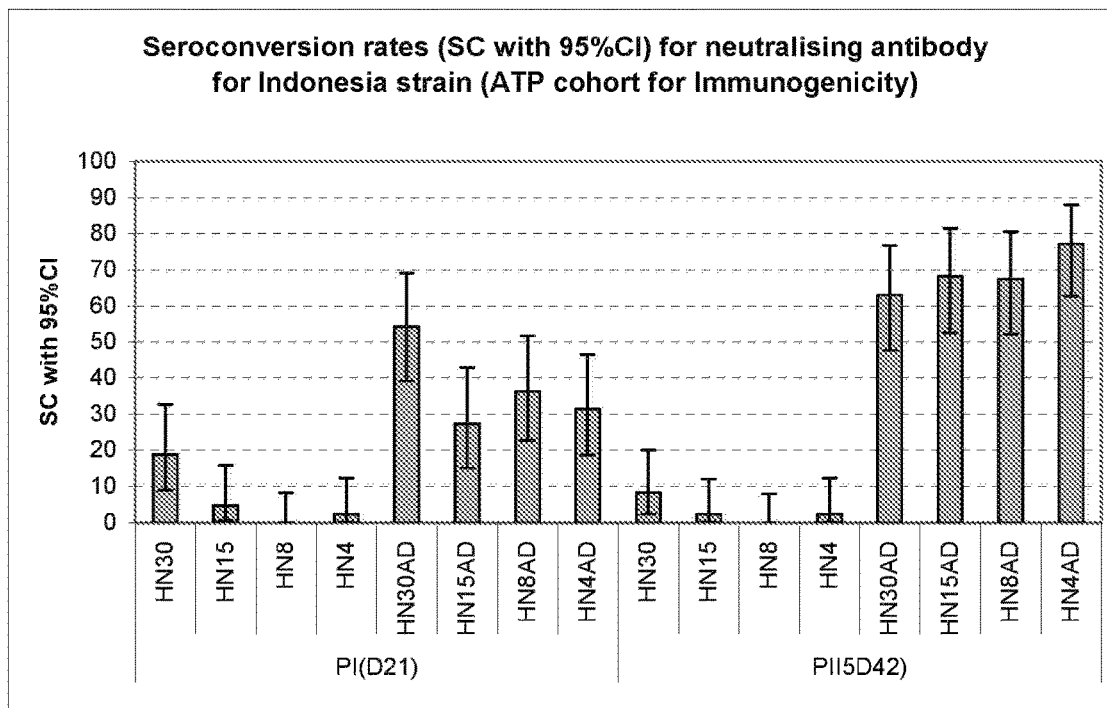

FIG. 11    CD 4 Specific response to H5N1 Vietnam strain

CD4 specific response to H5N1 Vietnam strain at Day0 and Day42

Legend: MEDIAN at Day 42 (Q1, Q3); MEDIAN at PRE

Y-axis: Specific CD4 / mio CD4 (0 to 5000)

X-axis groups (each with HN4, HN4AD, HN8, HN8AD): ALL DOUBLES, CD4OL, IFNg, IL2, TFNa FIG. 12    H5N1-specific serum IgG ELISA titers in C57Bl/6 mice (GMT +/- IC95)

Anti-A/Vietnam H5N1 - Mid-Point ELISA Values

| | H5N1 AS03 (3 µg) | H5N1 AS03 (1.5 µg) | H5N1 AS03 (0.75 µg) | H5N1 AS03 (0.38 µg) | H5N1 Plain (3 µg) | PBS |
|---|---|---|---|---|---|---|
| D14 Post Imm | 20834 | 31071 | 20309 | 30444 | 49 | 50 |

FIG. 13    Hemagglutination Inhibition test (GMT +/- IC95) in C57Bl/6 mice immunized with different doses of H5N1 A/Vietnam Anti-A/Vietnam H5N1 - HI titers

| | H5N1 AS03 (3 µg) | H5N1 AS03 (1.5 µg) | H5N1 AS03 (0.75 µg) | H5N1 AS03 (0.38 µg) | H5N1 Plain (3 µg) | PBS |
|---|---|---|---|---|---|---|
| D14 Post Imm | 3620 | 2381 | 2389 | 1810 | 11 | 5 |

FIG. 14  Anti-H5N1 A/Vietnam (A) and anti-H5N1 A/Indonesia (B) neutralizing antibody responses (GMT) in ferrets immunized with different vaccines A - Anti-H5N1 A/Vietnam response

| | AS03 alone | Non-adj H5N1 (15 µg) | AS03 H5N1 (1.7 µg) | AS03 H5N1 (3.8 µg) | AS03 H5N1 (7.5 µg) | AS03 H5N1 (15 µg) |
|---|---|---|---|---|---|---|
| ☐ Post-I immunization | 14 | 14 | 14 | 24 | 16 | 16 |
| ■ Post-II immunization | 14 | 14 | 83 | 113 | 104 | 83 |

A - Anti-H5N1 A/Indonesia response

| | AS03 alone | Non-adj H5N1 (15 µg) | AS03 H5N1 (1.7 µg) | AS03 H5N1 (3.8 µg) | AS03 H5N1 (7.5 µg) | AS03 H5N1 (15 µg) |
|---|---|---|---|---|---|---|
| ☐ Post-I immunization | 14 | 14 | 14 | 14 | 14 | 14 |
| ■ Post-II immunization | 14 | 14 | 36 | 43 | 35 | 26 |

Fig. 15   Mean virus titration data by viral culture of lung tissues from ferrets challenge with heterologous H5N1 viruses

H5N1 Virus Titration Lung Tissue log (TCID50/g Tissue)

| Non-adjuvanted (15 µg) | Adjuvant alone | H5N1-AS03 (15 µg) | H5N1-AS03 (7.5 µg) | H5N1-AS03 (3.8 µg) | H5N1-AS03 (1.7 µg) |

FIG. 16   H5N1-specific CD4+ T cell responses induced by different doses of adjuvanted H5N1 split vaccines % H5N1 split-specific CD4+ T cell

| H5N1 AS03 (1.5 µg) | H5N1 AS03 (0.38 µg) | No Adjuvant H5N1 (1.5 µg) | No Adjuvant H5N1 (0.38 µg) | PBS |

INFLUENZA VACCINE

CROSS REFERENCE TO RELATED APPLICATIONS

This application is a continuation of U.S. application Ser. No. 14/996,446, filed Jan. 15, 2016, which is a continuation of U.S. application Ser. No. 13/163,002 (now U.S. Pat. No. 9,278,127), filed Jun. 17, 2011, which is a continuation of U.S. application Ser. No. 11/692,792 (now abandoned), filed Mar. 28, 2007, which claims priority to U.S. Provisional Application No. 60/831,437, filed Jul. 17, 2006, and to Great Britain Application No. 0625453.6, filed Dec. 20, 2006, Great Britain Application No. 0623865.3, filed Nov. 29, 2006, Great Britain Application No. 0623218.5, filed Nov. 21, 2006, International Application No. PCT/EP2006/010439, filed Oct. 27, 2006, Great Britain Application No. 0619090.4, filed Sep. 27, 2006, and Great Britain Application No. 0618195.2, filed Sep. 15, 2006, and the contents of each of the preceeding applications are herein incorporated by reference in their entireties.

TECHNICAL FIELD

The present invention relates to influenza vaccine formulations and vaccination regimes for immunising against influenza disease, their use in medicine, in particular their use in augmenting immune responses to various antigens, and to methods of preparation. In particular, the invention relates to monovalent influenza immunogenic compositions comprising a low amount of influenza virus antigen or antigenic preparation thereof from an influenza virus strain that is associated with a pandemic or has the potential to be associated with a pandemic, in combination with an oil-in-water emulsion adjuvant.

TECHNICAL BACKGROUND

Influenza viruses are one of the most ubiquitous viruses present in the world, affecting both humans and livestock. Influenza results in an economic burden, morbidity and even mortality, which are significant.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. Influenza virus comprises two surface antigens, glycoproteins neuraminidase (NA) and haemagglutinin (HA), which appear as spikes, 10 to 12 nm long, at the surface of the particles. It is these surface proteins, particularly the haemagglutinin that determine the antigenic specificity of the influenza subtypes. Virus strains are classified according to host species of origin, geographic site and year of isolation, serial number, and, for influenza A, by serological properties of subtypes of HA and NA. 16 HA subtypes (H1-H16) and nine NA subtypes (N1-N9) have been identified for influenza A viruses [Webster R G et al. Evolution and ecology of influenza A viruses. *Microbiol. Rev.* 1992; 56:152-179; Fouchier R A et al. Characterization of a Novel Influenza A Virus Hemagglutinin Subtype (H16) Obtained from Black-Headed Gulls. *J. Virol.* 2005; 79:2814-2822). Viruses of all HA and NA subtypes have been recovered from aquatic birds, but only three HA subtypes (H1, H2, and H3) and two NA subtypes (N1 and N2) have established stable lineages in the human population since 1918. Only one subtype of HA and one of NA are recognised for influenza B viruses.

Influenza A viruses evolve and undergo antigenic variability continuously [Wiley D, Skehel J. The structure and the function of the hemagglutinin membrane glycoprotein of influenza virus. *Ann. Rev. Biochem.* 1987; 56:365-394]. A lack of effective proofreading by the viral RNA polymerase leads to a high rate of transcription errors that can result in amino-acid substitutions in surface glycoproteins. This is termed "antigenic drift". The segmented viral genome allows for a second type of antigenic variation. If two influenza viruses simultaneously infect a host cell, genetic reassortment, called "antigenic shift" may generate a novel virus with new surface or internal proteins. These antigenic changes, both 'drifts' and 'shifts' are unpredictable and may have a dramatic impact from an immunological point of view as they eventually lead to the emergence of new influenza strains and that enable the virus to escape the immune system causing the well known, almost annual, epidemics. Both of these genetic modifications have caused new viral variants responsible for pandemic in humans.

HA is the most important antigen in defining the serological specificity of the different influenza strains. This 75-80 kD protein contains numerous antigenic determinants, several of which are in regions that undergo sequence changes in different strains (strain-specific determinants) and others in regions which are common to many HA molecules (common to determinants).

Influenza viruses cause epidemics almost every winter, with infection rates for type A or B virus as high as 40% over a six-week period. Influenza infection results in various disease states, from a sub-clinical infection through mild upper respiratory infection to a severe viral pneumonia. Typical influenza epidemics cause increases in incidence of pneumonia and lower respiratory disease as witnessed by increased rates of hospitalization or mortality. The severity of the disease is primarily determined by the age of the host, his immune status and the site of infection.

Elderly people, 65 years old and over, are especially vulnerable, accounting for 80-90% of all influenza-related deaths in developed countries. Individuals with underlying chronic diseases are also most likely to experience such complications. Young infants also may suffer severe disease. These groups in particular therefore need to be protected. Besides these 'at risk'-groups, the health authorities are also recommending to vaccinate health care providers.

Vaccination plays a critical role in controlling annual influenza epidemics. Currently available influenza vaccines are either inactivated or live attenuated influenza vaccine. Inactivated flu vaccines are composed of three possible forms of antigen preparation: inactivated whole virus, sub-virions where purified virus particles are disrupted with detergents or other reagents to solubilise the lipid envelope (so-called "split" vaccine) or purified HA and NA (subunit vaccine). These inactivated vaccines are given intramuscularly (i.m.), subcutaneously (s.c), or intranasally (i.n.).

Influenza vaccines for interpandemic use, of all kinds, are usually trivalent vaccines. They generally contain antigens derived from two influenza A virus strains and one influenza B strain. A standard 0.5 ml injectable dose in most cases contains (at least) 15 µg of haemagglutinin antigen component from each strain, as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol.

Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330).

Interpandemic influenza virus strains to be incorporated into influenza vaccine each season are determined by the World Health Organisation in collaboration with national health authorities and vaccine manufacturers. Interpandemic Influenza vaccines currently available are considered safe in all age groups (De Donato et al. 1999, Vaccine, 17, 3094-3101). However, there is little evidence that current influenza vaccines work in small children under two years of age. Furthermore, reported rates of vaccine efficacy for prevention of typical confirmed influenza illness are 23-72% for the elderly, which are significantly lower than the 60-90% efficacy rates reported for younger adults (Govaert, 1994, J. Am. Med. Assoc., 21, 166-1665; Gross, 1995, Ann Intern. Med. 123, 523-527). The effectiveness of an influenza vaccine has been shown to correlate with serum titres of hemagglutination inhibition (HI) antibodies to the viral strain, and several studies have found that older adults exhibit lower HI titres after influenza immunisation than do younger adults (Murasko, 2002, Experimental gerontology, 37, 427-439).

A sub-unit influenza vaccine adjuvanted with the adjuvant MF59, in the form of an oil-in-water emulsion is commercially available for the elderly and at risk population, and has demonstrated its ability to induce a higher antibody titer than that obtained with the non-adjuvanted sub-unit vaccine (De Donato et al. 1999, Vaccine, 17, 3094-3101). However, in a later publication, the same vaccine has not demonstrated its improved profile compared to a non-adjuvanted split vaccine (Puig-Barbera et al., 2004, Vaccine 23, 283-289).

By way of background, during inter-pandemic periods, influenza viruses that circulate are related to those from the preceding epidemic. The viruses spread among people with varying levels of immunity from infections earlier in life. Such circulation, over a period of usually 2-3 years, promotes the selection of new strains that have changed enough to cause an epidemic again among the general population; this process is termed 'antigenic drift'. 'Drift variants' may have different impacts in different communities, regions, countries or continents in any one year, although over several years their overall impact is often similar. Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease.

At unpredictable intervals, novel influenza viruses emerge with a key surface antigen, the haemagglutinin, of a totally different subtype from strains circulating the season before. Here, the resulting antigens can vary from 20% to 50% from the corresponding protein of strains that were previously circulating in humans. This can result in virus escaping 'herd immunity' and establishing pandemics. This phenomenon is called 'antigenic shift'. In other words, an influenza pandemics occurs when a new influenza virus appears against which the human population has no immunity. It is thought that at least the past pandemics have occurred when an influenza virus from a different species, such as an avian or a porcine influenza virus, has crossed the species barrier. If such viruses have the potential to spread from human to human, they may spread worldwide within a few months to a year, resulting in a pandemic. For example, in 1957 (Asian Flu pandemic), viruses of the H2N2 subtype replaced H1N1 viruses that had been circulating in the human population since at least 1918 when the virus was first isolated. The H2 HA and N2 NA underwent antigenic drift between 1957 and 1968 until the HA was replaced in 1968 (Hong-Kong Flu pandemic) by the emergence of the H3N2 influenza subtype, after which the N2 NA continued to drift along with the H3 HA (Nakajima et al., 1991, Epidemiol. Infect. 106, 383-395).

The features of an influenza virus strain that give it the potential to cause a pandemic outbreak are: it contains a new haemagglutinin compared to the haemagglutinin in the currently circulating strains, which may or may not be accompanied by a change in neuraminidase subtype; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in birds. In either case the majority, or at least a large proportion of, or even the entire population has not previously encountered the antigen and is immunologically naïve to it.

Several clinical studies have been performed to evaluate safety and immunogenicity in unprimed populations, with monovalent candidate vaccines containing a pandemic strain such as the non-circulating H2N2 or H9N2 strains. Studies have investigated split or whole virus formulations of various HA concentrations (1.9, 3.8, 7.5 or 15 µg HA per dose), with or without alum adjuvantation. Influenza viruses of the H2N2 subtype circulated from 1957 until 1968 when they were replaced by H3N2 strains during the 'Hong Kong pandemic'. Today, individuals that were born after 1968 are immunologically naïve to H2N2 strains. These vaccine candidates have been shown to be immunogenic and well tolerated. Results are reported in Hehme, N et al. 2002, Med. Microbiol. Immunol. 191, 203-208; in Hehme N. et al. 2004, Virus Research 103, 163-171; and two studies were reported with H5N1 (Bresson J L et al. *The Lancet.* 2006:367 (9523):1657-1664; Treanor J J et al. *N Engl J Med.* 2006; 354:1343-1351). Other studies have reported results with MF59 adjuvanted influenza vaccines. One study has reported that two doses of an H5N3 influenza vaccine adjuvanted with MF59 was boosting immunity to influenza H5N1 in a primed population (Stephenson et al., Vaccine 2003, 21, 1687-1693) and another study has reported cross-reactive antibody responses to H5N1 viruses obtained after three doses of MF59-adjuvanted influenza H5N3 vaccine (Stephenson et al., J. Infect. Diseases 2005, 191, 1210-1215).

Persons at risk in case of an influenza pandemic may be different from the defined risk-groups for complications due to seasonal influenza. According to the WHO, 50% of the human cases caused by the avian influenza strain H5N1 occurred in people below 20 years of age, 90% occurred among those aged <40. (WHO, weekly epidemiological record, 30 Jun. 2006).

During a pandemic, antiviral drugs may not be sufficient or effective to cover the needs and the number of individuals at risk of influenza will be greater than in interpandemic periods, therefore the development of a suitable vaccine with the potential to be produced in large amounts and with efficient distribution and administration potential is essential. For these reasons, monovalent instead of trivalent vaccines are being developed for pandemic purposes in an attempt to reduce vaccine volume, primarily as two doses of vaccine may be necessary in order to achieve protective antibody levels in immunologically naïve recipients (Wood J M et al. Med Mircobiol Immunol. 2002; 191:197-201. Wood J M et al. Philos Trans R Soc Lond B Biol Sci. 2001; 356:1953-1960).

These problems may be countered by adjuvantation, the aim of which is to increase immunogenicity of the vaccine in order to be able to decrease the antigen content (antigen sparing) and thus increase the number of vaccine doses available. The use of an adjuvant may also overcome the potential weak immunogenicity of the antigen in a naïve population. Examples of the above have been shown using whole inactivated H2N2 or H9N2 virus adjuvanted with aluminium salt (N. Hehme et al. Virus Research 2004, 103, 163-171). Clinical trials with plain subvirion H5N1 vaccine or aluminium hydroxide adjuvanted split virus H5N1 vaccine have already been performed. The results of these trials indicate that both plain and adjuvanted H5N1 virus vaccines are safe up to an antigen dose of 90 µg (tested only as plain subvirion vaccine) (Bresson J L et al. The Lancet. 2006:367 (9523):1657-1664; Treanor J J et al. N Engl J Med. 2006; 354:1343-1351)

New vaccines with an improved immunogenicity, in particular against weakly or non-immunogenic pandemic strains or for the immuno-compromised individuals such as the elderly population, are therefore still needed. New vaccines with a cross-protection potential are also needed, that could be used as pre-pandemic or stockpiling vaccines to prime an immunologically naive population against a pandemic strain before or upon declaration of a pandemic. Formulation of vaccine antigen with potent adjuvants is a possible approach for enhancing immune responses to subvirion antigens. Novel adjuvant formulations are hereby provided which allow an antigen sparing formulation affording sufficient protection (seroconversion of previously seronegative subjects to a HI titer considered as protective, 1:40 or fourfold increase in titer) of all age groups.

STATEMENT OF THE INVENTION

In first aspect of the present invention, there is provided an influenza immunogenic composition, in particular a vaccine, comprising a low amount of influenza virus antigen or antigenic preparation from an influenza virus strain that is associated with a pandemic or has the potential to be associated with a pandemic, in combination with an adjuvant, wherein the low antigen amount does not exceed 15 µg of haemagglutinin (HA) per dose, and wherein said adjuvant is an oil-in-water emulsion comprising a metabolisable oil, a sterol and/or a tocopherol, such as alpha tocopherol, and an emulsifying agent. Suitably the vaccine composition is a monovalent composition.

Throughout the document it will be referred to a pandemic strain as an influenza strain being associated or susceptible to be associated with an outbreak of influenza disease, such as pandemic Influenza A strains. Suitable strains are in particular avian (bird) influenza strains. Suitable pandemic strains are, but not limited to: H5N1 (the highly pathogenic avian H5N1 strain, now endemic in many bird species across the world, is a candidate pandemic strain according to this invention), H9N2, H7N7, H2N2, H7N1 and H1N1. Others suitable pandemic strains in human are H7N3 (2 cases reported in Canada), H10N7 (2 cases reported in Egypt) and H5N2 (1 case reported in Japan).

In another aspect, the invention provides a method for the production of an influenza immunogenic composition, in particular a vaccine, for a pandemic situation or a pre-pandemic situation which method comprises admixing an influenza virus antigen or antigenic preparation thereof from a single influenza virus strain that is associated with a pandemic or has the potential to be associated with a pandemic, with an oil-in-water emulsion adjuvant as herein above defined, and providing vaccine units which contain no more than 15 µg influenza haemagglutinin antigen per dose. The influenza virus may be egg-derived, plant-derived, cell-culture derived, or may be recombinantly produced. Suitably the influenza virus antigen is egg-derived or cell culture-derived.

In a third aspect, there is provided an immunogenic composition as herein defined for use in medicine.

In yet another aspect there is provided the use of (a) a low amount, as herein defined, of influenza virus antigen or antigenic preparation thereof from a single strain of influenza associated with a pandemic or having the potential to be associated with a pandemic, and (b) an oil-in-water emulsion adjuvant, in the manufacture of an immunogenic composition, or a kit, for inducing at least one of i) an improved CD4 T-cell immune response, ii) an improved B cell memory response, iii) an improved humoral response, against said virus antigen or antigenic composition in a human. Said immune response is in particular induced in an immuno-compromised individual or population, such as a high risk adult or an elderly. Suitably the immunogenic composition is as herein defined.

There is also provided the use of an influenza virus or antigenic preparation thereof and an oil-in-water emulsion adjuvant in the preparation of an immunogenic composition as herein defined for vaccination of human elderly against influenza.

In a specific embodiment, the immunogenic composition is capable of inducing both an improved CD4 T-cell immune response and an improved B-memory cell response compared to that obtained with the un-adjuvanted antigen or antigenic composition. In another specific embodiment, the immunogenic composition is capable of inducing both an improved CD4 T-cell immune response and an improved humoral response compared to that obtained with the un-adjuvanted antigen or antigenic composition. In particular, said humoral immune response or protection meets at least one, suitably two typically all three EU or FDA regulatory criteria for influenza vaccine efficacy. Suitably, said immune response(s) or protection is obtained after one, suitably two, doses of vaccine. Specifically said immune response(s) or protection meets at least one, suitably two or all three EU or FDA regulatory criteria for influenza vaccine efficacy after one dose of adjuvanted vaccine. Specifically at least one, suitably two FDA or EU criteria is (are) met after only one dose of vaccine. Efficacy criteria for the composition according to the present invention are further detailed below (see Table 1 and below under "efficacy criteria"). Suitably said composition is administered parenterally, in particular via the intramuscular or the sub-cutaneous route.

In a further embodiment, there is provided the use of a low amount of an influenza virus or antigenic preparation thereof in the manufacture of an immunogenic composition for revaccination of humans previously vaccinated with a monovalent influenza immunogenic composition comprising an influenza antigen or antigenic preparation thereof from a single influenza virus strain which is associated with a pandemic or has the potential to be associated with a pandemic, in combination with an oil-in-water emulsion adjuvant as herein defined.

In a specific embodiment, the composition used for the revaccination may be un-adjuvanted or may contain an adjuvant, in particular an oil-in-water emulsion adjuvant. In another specific embodiment, the immunogenic composition for revaccination contains an influenza virus or antigenic preparation thereof which shares common CD4 T-cell epitopes with the influenza virus or virus antigenic preparation thereof used for the first vaccination. The immunogenic composition for a revaccination may contain a classical amount (i.e. about 15 µg of HA) of said variant pandemic strain.

Suitably the revaccination is made in subjects who have been vaccinated the previous season against influenza. Suitably, the revaccination is made with a vaccine comprising an influenza strain (e.g. H5N1 Vietnam) which is of the same subtype as that used for the first vaccination (e.g. H5N1 Vietnam). In a specific embodiment, the revaccination is made with a drift strain of the same sub-type, e.g. H5N1 Indonesia. In another embodiment, said influenza strain used for the revaccination is a shift strain, i.e. is different from that used for the first vaccination, e.g. it has a different HA or NA subtype, such as H5N2 (same HA subtype as H5N1 but different NA subtype) or H7N1 (different HA subtype from H5N1 but same NA subtype).

Suitably the first vaccination is made at the declaration of a pandemic and revaccination is made later. Alternatively the first vaccination is part of a pre-pandemic strategy and is made before the declaration of a pandemic, as a priming strategy, thus allowing the immune system to be primed, with the revaccination made subsequently. In this instance one or two doses of vaccine containing the same influenza strain are administered as part of the primo-vaccination. Revaccination, in particular with a variant (e.g. drift) strain, can be made at any time after the first course (one or two doses) of vaccination. Typically revaccination is made at least 1 month, suitably at least two months, suitably at least three months, or 4 months after the first vaccination, suitably 6 or 8 to 14 months after, suitably at around 10 to 12 months after or even longer. Suitably revaccination one year later or even more than one year later is capable of boosting antibody and/or cellular immune response. This is especially important as further waves of infection may occur several months after the first outbreak of a pandemic. As needed, revaccination may be made more than once.

Suitably said oil-in-water emulsion comprises a metabolisable oil, a sterol and/or a tocopherol, such as alpha tocopherol, and an emulsifying agent. In a another specific embodiment, said oil-in-water emulsion adjuvant comprises at least one metabolisable oil in an amount of 0.5% to 20% of the total volume, and has oil droplets of which at least 70% by intensity have diameters of less than 1 µm. Suitably said a tocopherol, such as alpha tocopherol, is present in an amount of 1.0% to 20%, in particular in an amount of 1.0% to 5% of the total volume of said immunogenic composition.

In a further aspect of the present invention, there is provided the use of an antigen or antigenic preparation from a first pandemic influenza strain in the manufacture of an immunogenic composition as herein defined for protection against influenza infections caused by a variant influenza strain.

In a specific aspect, there is provided a method of vaccination of an immuno-compromised human individual or population such as high risk adults or elderly, said method comprising administering to said individual or population an influenza immunogenic composition comprising a low amount of an influenza antigen or antigenic preparation thereof from a single pandemic influenza virus strain in combination with an oil-in-water emulsion adjuvant as herein defined.

In still another embodiment, the invention provides a method for revaccinating humans previously vaccinated with a monovalent influenza immunogenic composition comprising an influenza antigen or antigenic preparation thereof from a single pandemic influenza virus strain, in combination with an oil-in-water emulsion adjuvant, said method comprising administering to said human an immunogenic composition comprising an influenza virus, either adjuvanted or un-adjuvanted.

In a further embodiment there is provided a method for vaccinating a human population or individual against one pandemic influenza virus strain followed by revaccination of said human or population against a variant influenza virus strain, said method comprising administering to said human (i) a first composition comprising an influenza virus or antigenic preparation thereof from a first pandemic influenza virus strain and an oil-in-water emulsion adjuvant, and (ii) a second immunogenic composition comprising a influenza virus strain variant of said first influenza virus strain. In a specific embodiment said variant strain is associated with a pandemic or has the potential to be associated with a pandemic. In another specific embodiment said variant strain is part of a multivalent composition which comprises, in addition to said pandemic influenza virus variant, at least one circulating (seasonal) influenza virus strain. In particular, said pandemic influenza virus strain is part of a bivalent, or a trivalent, or tetravalent composition additionally comprising one, two or three seasonal strains, respectively.

Throughout the document, the use of a low amount of pandemic influenza virus antigen in the manufacture of a composition as herein defined for prevention of influenza infection or disease, and a method of treatment of humans using the claimed composition will be interchangeably used.

Other aspects and advantages of the present invention are described further in the following detailed description of preferred embodiments thereof.

LEGEND TO FIGURES

FIG. 1: Oil droplet particle size distribution in SB62 oil-in-water emulsion as measured by PCS. FIG. 1A shows SB62 lot 1023 size measurements with the Malvern Zetasizer 3000HS: A=dilution 1/10000 (Rec22 to Rec24) (Analysis in Contin and adapted optical model 1.5/0.01); B=Dilution 1/20000 (Rec28 to Rec30) (Analysis in Contin and adapted optical model 1.5/0.01). FIG. 1B shows a schematic illustration of record 22 (upper part) and record 23 (lower part) by intensity.

FIG. 2: Ferrets experiments. FIG. 2A: Hemagglutination Inhibition test (GMT) in ferrets immunized with different doses of H5N1 A/Vietnam. FIG. 2B: Mean H5N1 PCR data (upper graph) and mean virus titration data (lower graph) of lung tissues from ferrets on day of death or euthanisation (PCR data are expressed as Control Dilution Units (CDU) which are determined from a standard curve produced from a stock of virus which is serially diluted, with each dilution undergoing nucleic acid extraction and TAQMAN™. PCR amplification in the same manner as test samples. Virus titration data is expressed as TCID50/g tissue).

FIG. 3: Anti-A/Vietnam neutralizing antibody responses in ferrets immunized with different doses of H5N1 A/Vietnam.

FIG. 4: Overview of the manufacture of influenza monovalent bulks.

FIG. 5: Formulation flow sheet for final bulk of antigen.

FIG. 6: Human clinical trial with a dose-range of H5N1 split virus antigen, adjuvanted or not with AS03. GMT's (with 95% CI) for anti-HA antibody at time-points days 0, 21 and 42.

FIG. 7: Human clinical trial with a dose-range of H5N1 split virus antigen, adjuvanted or not with AS03. Seroconversion rates (with 95% CI) for anti-HA antibody at post-vaccination day 21 and day 42.

FIG. 8: Human clinical trial with a dose-range of H5N1 split virus antigen, adjuvanted or not with AS03. Seroprotection rates (with 95% CI) for anti-HA antibody at each time-points (Day 0, Day 21 and Day 42).

FIG. 9: Human clinical trial with a dose-range of H5N1 split virus antigen, adjuvanted or not with AS03. Seroconversion factor (with 95% CI) for anti-HA antibody at post-vaccination (day 21 and 42).

FIG. 10: Neutralisation titers to H5N1 Vietnam strain. The results of a partial analysis of a Hemagglutination Inhibition test (GMT) is shown in FIG. 10A1 and the results of a total analysis of a Hemagglutination Inhibition test (GMT) is shown in FIG. 10A2. The results of a partial analysis of seroconversion rates for neutralizing antibody titer is shown in FIG. 10B1 and the results of a total analysis of seroconversion rates for neutralizing antibody titer is shown in FIG. 10B2. HN4=non-adjuvanted 3.8 µg HA; HN8=nonadjuvanted 7.5 µg HA; HN4AD=AS03 adjuvanted 3.8 µg HA; HN8AD=AS03 adjuvanted 7.5 µg HA. FIG. 10C shows GMT (95% CI) for the neutralizing antibodies against Indonesia strain (ATP cohort immunogenicity). FIG. 10D shows seroconversion rates (with 95% CI) for the neutralizing antibodies against Indonesia strain (ATP cohort for immunogenicity).

FIG. 11: CD 4 Specific response to H5N1 Vietnam strain. HN4=non-adjuvanted 3.8 µg HA; HN8=non-adjuvanted 7.5 µg HA; HN4AD=AS03 adjuvanted 3.8 µg HA; HN8AD=AS03 adjuvanted 7.5 µg HA.

FIG. 12: H5N1-specific serum IgG ELISA titers in C57Bl/6 naive mice (GMT+/−IC95).

FIG. 13: Hemagglutination Inhibition test (GMT+/−IC95) in C57Bl/6 naive mice immunized with different doses of H5N1 A/Vietnam.

FIG. 14: Anti-H5N1 A/Vietnam (upper panel) and anti-H5N1 A/Indonesia (lower panel) neutralizing antibody responses (GMT) in ferrets immunized with different doses of adjuvanted H5N1 A/Vietnam vaccines, the non-adjuvanted H5N1 A/Vietnam vaccine or the adjuvant alone.

FIG. 15: Mean virus titration data by viral culture of lung tissues from ferrets challenge with heterologous H5N1 viruses.

FIG. 16: H5N1-specific CD4+ T cell responses induced by different doses of adjuvanted H5N1 split vaccines.

DETAILED DESCRIPTION

The present inventors have discovered that an influenza formulation comprising low amount of an influenza virus or antigenic preparation thereof associated with a pandemic or susceptible to be associated with a pandemic, together with an oil-in-water emulsion adjuvant comprising a metabolisable oil, a sterol and/or a tocopherol, such as alpha tocopherol, and an emulsifying agent, was capable of improving the humoral immune response, and/or the CD4 T-cell immune response and/or B cell memory response against said antigen or antigenic composition in a human or population, compared to that obtained with the un-adjuvanted virus or antigenic preparation thereof. They will allow to achieve protection against morbidity/mortality caused by a homologous influenza strain. The formulations adjuvanted with an oil-in-water emulsion adjuvant as herein defined will advantageously be used to induce anti-influenza CD4-T cell response capable of detection of influenza epitopes presented by MHC class II molecules. The formulations adjuvanted with an oil-in-water emulsion adjuvant as herein defined will advantageously be used to induce a cross-reactive immune response, i.e. detectable immunity (humoral and/or cellular) against a variant strain or against a range of related strains. The adjuvanted formulations will advantageously be effective to target the humoral and/or the cell-mediated immune system in order to increase responsiveness against homologous and drift influenza strains (upon vaccination and infection). They will also advantageously be used to induce, after one or two doses, a cross-priming strategy, i.e. induce "primed" immunological memory facilitating response upon revaccination (one-dose) with a variant strain. In this case i.e. after a course of pre-pandemic vaccine (administered in one or two doses), a recipient would need just one dose of pandemic vaccine (instead of two), to be fully protected against the actual pandemic strain.

The adjuvanted pandemic influenza compositions according to the invention have several advantages:
1) An improved immunogenicity: they will allow to improve weak immune response to less immunogenic influenza strains to level higher than those obtained with the un-adjuvanted formulations;
2) The use of adjuvants can overcome the potential weak immunogenicity of the antigen in a naïve population;
3) They may lead to an improved immunogenicity in specific populations such as in the elderly people (typically over 60 years of age) to levels seen in younger people aged 18 to 60 (antibody and/or T cell responses);
4) They may lead to an improved cross-protection profile: increased cross-reactivity, cross-protection against variant (drifted) influenza strains allowing the set-up of a cross-priming strategy where they can be used as pre-pandemic vaccines further allowing only one dose of a pandemic vaccine to be required to enhance the protection against the (circulating) pandemic strain;
5) By reaching any or all of these further advantages with a reduced antigen dosage, they will ensure an increased capacity in case of emergency or for preparedness of a pandemic situation (antigen-sparing in the pandemic situation) and offering a possibility of higher number of vaccine doses available to the population.

Other advantages will be apparent from the description and the example section below. The compositions for use in the present invention may be able to provide better seroprotection against influenza following revaccination, as assessed by the number of human subjects meeting the influenza correlates of protections. Furthermore, the composition for use in the present invention may also be able to induce a higher humoral response or B cell memory response following the first vaccination of a human subject, and a higher response following revaccination, compared to the non-adjuvanted composition.

The claimed adjuvanted compositions may also be able not only to induce but also maintain protective levels of antibodies against the influenza strain present in the vaccine, in more individuals than those obtained with the un-adjuvanted composition.

Thus, in still another embodiment, the claimed composition is capable of ensuring a persistent immune response against influenza related disease. In particular, by persistence it is meant an HI antibody immune response which is capable of meeting regulatory criteria after at least three months, suitably after at least 6 months after the vaccination. In particular, the claimed composition is able to induce protective levels of antibodies as measured by the protection rate (see Table 1) in >50%, suitably in >60% of individuals >70% of individuals, suitably in >80% of individuals or suitably in >90% of individuals for the pandemic influenza strain present in the vaccine, after at least three months. In a specific aspect, protective levels of antibodies of >90% are obtained at least 6 months post-vaccination against the influenza strain of the vaccine composition.

According to further aspects of the present invention, the claimed composition is capable to induce seroprotection and seroconversion to a higher degree than that provided for by the EU requirements for vaccine influenza strains. This will be further detailed below (see Table 1 and below under "efficacy criteria").

Influenza Viral Strains and Antigens

In one embodiment, an influenza virus or antigenic preparation thereof for use according to the present invention may be a split influenza virus or split virus antigenic preparation thereof. In an alternative embodiment the influenza preparation may contain another type of inactivated influenza antigen, such as inactivated whole virus or recombinant and/or purified HA and NA (subunit vaccine), or an influenza virosome. In a still further embodiment, the influenza virus may be a live attenuated influenza preparation.

A split influenza virus or split virus antigenic preparation thereof for use according to the present invention is suitably an inactivated virus preparation where virus particles are disrupted with detergents or other reagents to solubilise the lipid envelope. Split virus or split virus antigenic preparations thereof are suitably prepared by fragmentation of whole influenza virus, either infectious or inactivated, with solubilising concentrations of organic solvents or detergents and subsequent removal of all or the majority of the solubilising agent and some or most of the viral lipid material. By split virus antigenic preparation thereof is meant a split virus preparation which may have undergone some degree of purification compared to the split virus whilst retaining most of the antigenic properties of the split virus components. For example, when produced in eggs, the split virus may be depleted from egg-contaminating proteins, or when produced in cell culture, the split virus may be depleted from host cell contaminants. A split virus antigenic preparation may comprise split virus antigenic components of more than one viral strain. Vaccines containing split virus (called 'influenza split vaccine') or split virus antigenic preparations generally contain residual matrix protein and nucleoprotein and sometimes lipid, as well as the membrane envelope proteins. Such split virus vaccines will usually contain most or all of the virus structural proteins although not necessarily in the same proportions as they occur in the whole virus.

Alternatively, the influenza virus may be in the form of a whole virus vaccine. This may prove to be an advantage over a split virus vaccine for a pandemic situation as it avoids the uncertainty over whether a split virus vaccine can be successfully produced for a new strain of influenza virus. For some strains the conventional detergents used for producing the split virus can damage the virus and render it unusable. Although there is always the possibility to use different detergents and/or to develop a different process for producing a split vaccine, this would take time, which may not be available in a pandemic situation. In addition to the greater degree of certainty with a whole virus approach, there is also a greater vaccine production capacity than for split virus since considerable amounts of antigen are lost during additional purification steps necessary for preparing a suitable split vaccine.

In another embodiment, the influenza virus preparation is in the form of a purified sub-unit influenza vaccine. Sub-unit influenza vaccines generally contain the two major envelope proteins, HA and NA, and may have an additional advantage over whole virion vaccines as they are generally less reactogenic, particularly in young vaccinees. Sub-unit vaccines can be produced either recombinantly or purified from disrupted viral particles.

In another embodiment, the influenza virus preparation is in the form of a virosome. Virosomes are spherical, unilamellar vesicles which retain the functional viral envelope glycoproteins HA and NA in authentic conformation, intercalated in the virosomes' phospholipids bilayer membrane.

Said influenza virus or antigenic preparation thereof may be egg-derived or cell-culture derived. They may also be produced in other systems such as insect cells, plants, yeast or bacteria or be recombinantly produced.

For example, the influenza virus antigen or antigenic preparations thereof according to the invention may be derived from the conventional embryonated egg method, by growing influenza virus in eggs and purifying the harvested allantoic fluid. Eggs can be accumulated in large numbers at short notice. Alternatively, they may be derived from any of the new generation methods using tissue culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 or Per-C6 cells. Suitable cell substrates are not limited to cell lines; for example primary cells such as chicken embryo fibroblasts and avian cell lines are also included.

The influenza virus antigen or antigenic preparation thereof may be produced by any of a number of commercially applicable processes, for example the split flu process described in patent no. DD 300 833 and DD 211 444, incorporated herein by reference. Traditionally split flu was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or sodium-dodecyl sulfate or non-ionic detergents such as the ones described above including Triton X-100 (for example in a process described in Lina et al, 2000, Biologicals 28, 95-103) and Triton N-101, or combinations of any two or more detergents.

The preparation process for a split vaccine may include a number of different filtration and/or other separation steps such as ultracentrifugation, ultrafiltration, zonal centrifugation and chromatography (e.g. ion exchange) steps in a variety of combinations, and optionally an inactivation step eg with heat, formaldehyde or β-propiolactone or U.V. irradiation which may be carried out before or after splitting. The splitting process may be carried out as a batch, continuous or semi-continuous process. A suitable splitting and purification process for a split immunogenic composition is described in WO 02/097072.

Suitable split flu vaccine antigen preparations according to the invention comprise a residual amount of Tween 80 and/or Triton X-100 remaining from the production process, although these may be added or their concentrations adjusted after preparation of the split antigen. Suitably both Tween 80 and Triton X-100 are present. Suitable ranges for the final concentrations of these non-ionic surfactants in the vaccine dose are: Tween 80: 0.01 to 1%, suitably about 0.1% (v/v) Triton X-100: 0.001 to 0.1 (% w/v), suitably 0.005 to 0.02% (w/v).

In a specific embodiment, the final concentration for Tween 80 ranges from 0.045%-0.09% w/v. In another specific embodiment, the antigen is provided as a 2-fold concentrated mixture, which has a Tween 80 concentration ranging from 0.045%-0.2% (w/v) and has to be diluted two times upon final formulation with the adjuvanted (or the buffer in the control formulation).

In another specific embodiment, the final concentration for Triton X-100 ranges from 0.005%-0.017% w/v. In another specific embodiment, the antigen is provided as a 2 fold concentrated mixture, which has a Triton X-100 concentration ranging from 0.005%-0.034% (w/v) and has to be diluted two times upon final formulation with the adjuvanted (or the buffer in the control formulation).

The influenza preparation may be prepared in the presence of a preservative such as thiomersal. Suitably the preservative, in particular thiomersal, is present at a concentration of around 100 µg/ml. Alternatively, the influenza preparation is prepared in the presence of low level of preservative in particular thiomersal, such as a concentration not exceeding 20 µg/ml or suitably less than 5 µg/ml. In another suitable alternative embodiment, the influenza preparation is made in the absence of thiomersal. Suitably the resulting influenza preparation is stable in the absence of organomercurial preservatives, in particular the preparation contains no residual thiomersal. In particular the influenza virus preparation comprises a haemagglutinin antigen stabilised in the absence of thiomersal, or at low levels of thiomersal (generally 5 µg/ml or less). Specifically the stabilization of B influenza strain is performed by a derivative of alpha tocopherol, such as alpha tocopherol succinate (also known as vitamin E succinate, i.e. VES). Such preparations and methods to prepare them are disclosed in WO 02/097072.

Alternatively, especially for multi-dose containers, thiomersal or any other suitable preservative is present in order to reduce the contamination risks. This is particularly of relevance for pandemic vaccines, designed to vaccinate as many people as possible in the shortest possible time.

A suitable composition for revaccination contains three inactivated split virion antigens prepared from the WHO recommended strains of the appropriate influenza season, in addition to a pandemic influenza strain.

In one embodiment the influenza virus or antigenic preparation thereof and the oil-in-water emulsion adjuvant are contained in the same container. It is referred to as 'one vial approach'. Suitably the vial is a pre-filled syringe or a 10-dose multi-dose vial or a 12-dose ampoule. In an alternative embodiment, the influenza virus or antigenic preparation thereof and the oil-in-water emulsion adjuvant are contained in separate containers or vials or units and admixed shortly before or upon administration into the subject. It is referred to as 'two vials approach'. By way of example, when the vaccine is a 2 components vaccine for a total dose volume of injected dose of 0.5 ml, the concentrated antigens (for example the concentrated inactivated split virion antigens) may be presented in one vial (330 µl) (antigen container, such as a vial) and a pre-filled syringe contains the adjuvant (400 µl) (adjuvant container, such as a syringe). Typically, the pandemic vaccine is a 0.5 ml injected dose and multidose vials contain a 1:1 vial:vial mixture prior to first subject injected. Alternatively, the pandemic vaccine is a 1.0 ml vial:syringe injected dose. At the time of injection, the content of the vial containing the concentrated inactivated split virion antigens is removed from the vial by using the syringe containing the adjuvant followed by gentle mixing of the syringe. Prior to injection, the used needle is replaced by an intramuscular needle and the volume is corrected to 530 µl. One dose of the reconstituted adjuvanted influenza vaccine candidate corresponds to 530 µl.

Suitably the adjuvanted pandemic influenza candidate vaccine is a 2 component vaccine consisting of 0.5 ml of concentrated inactivated split virion antigens presented in a type I glass vial and of a pre-filled type I glass syringe containing 0.5 ml of the adjuvant. Alternatively the vaccine is a 2 components vaccine presented in 2 vials (one for the antigen one for the adjuvant, of 10 doses each) for mixture prior to the administration to the first patient within 24 hours at room temperature and subsequent storage at 4° C. for a short period of time (e.g. up to one week) for subsequent administration. At the time of injection, the content of the multi-dose vial or the syringe containing the adjuvant is injected into the vial that contains the concentrated split virion antigen. After mixing the content is withdrawn into the syringe and the needle is replaced by an intramuscular needle. One dose of the reconstituted adjuvanted influenza candidate vaccine corresponds to 0.5 ml. Each vaccine dose of 0.5 ml contains a low dose of haemagglutinin (HA), such as a dose less than 15 µg of HA, suitably less than 10 µg. Suitable amounts are 1.9 µg, 3.8 µg, 7.5 µg, or 10 µg HA or any suitable amount of HA lower than 15 µg which would have be determined such that the vaccine composition meets the efficacy criteria as defined herein. Advantageously an HA dose of 1 µg of HA or even less such as 0.5 µg of HA that would allow meeting the regulatory criteria defined above may be used. A vaccine dose of 0.5 ml is suitably used. A vaccine dose of 1 ml (0.5 ml adjuvant plus 0.5 ml antigen preparation) is also suitable.

According to the present invention, the influenza strain in the monovalent immunogenic composition as herein defined is associated with a pandemic or has the potential to be associated with a pandemic. Such strain may also be referred to as 'pandemic strains' in the text below. In particular, when the vaccine is a multivalent vaccine for revaccination, such as a bivalent, or a trivalent or a quadrivalent vaccine, at least one strain is associated with a pandemic or has the potential to be associated with a pandemic. Suitable strains are, but not limited to: H5N1, H9N2, H7N7, H2N2, H7N1 and H1N1. Other pandemic strains in human: H7N3 (2 cases reported in Canada), H10N7 (2 cases reported in Egypt) and H5N2 (1 case reported in Japan).

Said influenza virus or antigenic preparation thereof for revaccination is suitably multivalent such as bivalent or trivalent or quadrivalent or contain even more influenza strains. Suitably the influenza virus or antigenic preparation thereof for revaccination is trivalent or quadrivalent, having an antigen from three different influenza strains, at least one strain being associated with a pandemic or having the potential to be associated with a pandemic outbreak. Suitably the revaccination composition comprises a pandemic strain, which may be a variant of the pandemic strain present in the composition for the first vaccination, and three other strains, typically the classical circulating strains.

Alternatively a suitable pre-pandemic vaccine strategy entails periodic (such as every 1-2 years) immunization with influenza strains with pandemic potential with the goal of maintaining and broadening responses to these viruses over time. While waiting for the optimally matched and regulatory-approved H5N1 pandemic vaccine, pre-pandemic strategy of vaccination is carried out with an adjuvanted vaccine produced with an H5 strain that is antigenically distinct or from a different clade from the pandemic one will prime people before the spread of the pandemic strain and improve their protection at the time of vaccination with the H5N1 pandemic vaccine. Accordingly in one embodiment, the first vaccination is made with the claimed adjuvanted monovalent vaccine comprising one pandemic strain such as H5N1 in one year, followed by an adjuvanted composition comprising a different pandemic influenza strain such as for example a H5N1 strain from a different clade or H9N2 at the next time point (e.g. after 6 months, one year, or two years), then followed by vaccination with an adjuvanted composition comprising still another pandemic influenza strain such as H7N7 for example, and so forth. Since it is impossible to predict a) the timing of a potential pandemic and b) the specific pandemic strain, this strategy relying on the claimed adjuvanted composition will provide increased insurance for maximizing magnitude and breadth of protective immune responses at the right time. In these strategies the adjuvant is suitably as defined herein.

The features of an influenza virus strain that give it the potential to cause a pandemic or an outbreak of influenza disease associated with pandemic influenza strains are: it contains a new haemagglutinin compared to the haemagglutinin in the currently circulating strains and therefore nearly all people are immunologically naive; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in avian species (birds). In either case the majority, or at least a large proportion of, or even the entire population has not previously encountered the antigen and is immunologically naïve to it. At present, the influenza A virus that has been identified by the WHO as one that potentially could cause a pandemic in humans is the highly pathogenic H5N1 avian influenza virus. Therefore, the pandemic vaccine according to the invention will suitably comprise H5N1 virus. Two other suitable strains for inclusion into the claimed composition are H9N2 or H7N1.

Certain parties are generally at an increased risk of becoming infected with influenza in a pandemic situation. The elderly, the chronically ill and small children are particularly susceptible but many young adults and apparently healthy people are also at risk. For H2 influenza, the part of the population born after 1968 is at an increased risk. It is important for these groups to be protected effectively as soon as possible and in a simple way.

Another group of people who are at increased risk are travelers. People travel more today than ever before and the regions where most new viruses emerge, China and South East Asia, have become popular travel destinations in recent years. This change in travel patterns enables new viruses to reach around the globe in a matter of weeks rather than months or years.

Thus for these groups of people there is a particular need for vaccination to protect against influenza in a pandemic situation or a potential pandemic situation. Suitable pandemic strains are, but not limited to: H5N1, H9N2, H7N7, H7N1, H2N2 and H1N1. Others pandemic strains in human: H7N3 (2 cases reported in Canada), H10N7 (2 cases reported in Egypt) and H5N2 (1 case reported in Japan).

Oil-in-Water Emulsion Adjuvant

The adjuvant composition of the invention contains an oil-in-water emulsion adjuvant, suitably said emulsion comprises a metabolisable oil in an amount of 0.5% to 20% of the total volume, and having oil droplets of which at least 70% by intensity have diameters of less than 1 µm.

In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly suitable oil for use in this invention. Squalene is a metabolisable oil by virtue of the fact that it is an intermediate in the biosynthesis of cholesterol (Merck index, 10th Edition, entry no. 8619).

Oil in water emulsions per se are well known in the art, and have been suggested to be useful as adjuvant compositions (EP 399843; WO 95/17210).

Suitably the metabolisable oil is present in an amount of 0.5% to 20% (final concentration) of the total volume of the immunogenic composition, suitably an amount of 1.0% to 10% of the total volume, suitably in an amount of 2.0% to 6.0% of the total volume.

In a specific embodiment, the metabolisable oil is present in a final amount of about 0.5%, 1%, 3.5% or 5% of the total volume of the immunogenic composition. In another specific embodiment, the metabolisable oil is present in a final amount of 0.5%, 1%, 3.57% or 5% of the total volume of the immunogenic composition. A suitable amount of squalene is about 10.7 mg per vaccine dose, suitably from 10.4 to 11.0 mg per vaccine dose.

Suitably the oil-in-water emulsion systems of the present invention have a small oil droplet size in the sub-micron range. Suitably the droplet sizes will be in the range 120 to 750 nm, suitably sizes from 120 to 600 nm in diameter. Typically the oil-in water emulsion contains oil droplets of which at least 70% by intensity are less than 500 nm in diameter, in particular at least 80% by intensity are less than 300 nm in diameter, suitably at least 90% by intensity are in the range of 120 to 200 nm in diameter.

The oil droplet size, i.e. diameter, according to the present invention is given by intensity. There are several ways of determining the diameter of the oil droplet size by intensity. Intensity is measured by use of a sizing instrument, suitably by dynamic light scattering such as the Malvern Zetasizer 4000 or suitably the Malvern Zetasizer 3000HS. A detailed procedure is given in Example II.2. A first possibility is to determine the z average diameter ZAD by dynamic light scattering (PCS-Photon correlation spectroscopy); this method additionally give the polydispersity index (PDI), and both the ZAD and PDI are calculated with the cumulants algorithm. These values do not require the knowledge of the particle refractive index. A second mean is to calculate the diameter of the oil droplet by determining the whole particle size distribution by another algorithm, either the Contin, or NNLS, or the automatic "Malvern" one (the default algorithm provided for by the sizing instrument). Most of the time, as the particle refractive index of a complex composition is unknown, only the intensity distribution is taken into consideration, and if necessary the intensity mean originating from this distribution.

The oil in water emulsion according to the invention comprises a sterol and/or a tocol such as tocopherol, in particular alpha tocopherol. Sterols are well known in the art, for example cholesterol is well known and is, for example, disclosed in the Merck Index, 11th Edn., page 341, as a naturally occurring sterol found in animal fat. Other suitable sterols include β-sitosterol, stigmasterol, ergosterol and ergocalciferol. Said sterol is suitably present in an amount of 0.01% to 20% (w/v) of the total volume of the immunogenic composition, suitably at an amount of 0.1% to 5% (w/v). Suitably, when the sterol is cholesterol, it is present in an amount of between 0.02% and 0.2% (w/v) of the total volume of the immunogenic composition, typically at an amount of 0.02% (w/v) in a 0.5 ml vaccine dose volume, or 0.07% (w/v) in 0.5 ml vaccine dose volume or 0.1% (w/v) in 0.7 ml vaccine dose volume.

Tocols (e.g. vitamin E) are also often used in oil emulsions adjuvants (EP 0 382 271 B1; U.S. Pat. No. 5,667,784; WO 95/17210). Tocols used in the oil emulsions (optionally oil in water emulsions) of the invention may be formulated as described in EP 0 382 271 B1, in that the tocols may be dispersions of tocol droplets, optionally comprising an emulsifier, of optionally less than 1 micron in diameter. Alternatively, the tocols may be used in combination with another oil, to form the oil phase of an oil emulsion. Examples of oil emulsions which may be used in combination with the tocol are described herein, such as the metabolisable oils described above.

Suitably alpha-tocopherol or a derivative thereof such as alpha-tocopherol succinate is present. Suitably alpha-tocopherol is present in an amount of between 0.2% and 5.0% (v/v) of the total volume of the immunogenic composition, suitably at an amount of 2.5% (v/v) in a 0.5 ml vaccine dose volume, or 0.5% (v/v) in 0.5 ml vaccine dose volume or 1.7-1.9% (v/v), suitably 1.8% in 0.7 ml vaccine dose volume. By way of clarification, concentrations given in v/v can be converted into concentration in w/v by applying the following conversion factor: a 5% (v/v) alpha-tocopherol concentration is equivalent to a 4.8% (w/v) alpha-tocopherol concentration. A suitable amount of alpha-tocopherol is about 11.9 mg per vaccine dose, suitably from 11.6 to 12.2 mg per vaccine dose.

The oil in water emulsion comprises an emulsifying agent. The emulsifying agent may be present at an amount of 0.01 to 5.0% by weight of the immunogenic composition (w/w), suitably present at an amount of 0.1 to 2.0% by weight (w/w). Suitable concentration are 0.5 to 1.5% by weight (w/w) of the total composition.

The emulsifying agent may suitably be polyoxyethylene sorbitan monooleate (Tween 80). In a specific embodiment, a 0.5 ml vaccine dose volume contains 1% (w/w) Tween 80, and a 0.7 ml vaccine dose volume contains 0.7% (w/w) Tween 80. In another specific embodiment the concentration of Tween 80 is 0.2% (w/w). A suitable amount of polysorbate 80 is about 4.9 mg per vaccine dose, suitably from 4.6 to 5.2 mg per vaccine dose.

Suitably a vaccine dose comprises alpha-tocopherol in an amount of about 11.9 mg per vaccine dose, squalene in an amount of 10.7 mg per vaccine dose, and polysorbate 80 in an amount of about 4.9 mg per vaccine dose.

The oil in water emulsion adjuvant may be utilised with other adjuvants or immuno-stimulants and therefore an important embodiment of the invention is an oil in water formulation comprising squalene or another metabolisable oil, a tocopherol, such as alpha tocopherol, and tween 80. The oil in water emulsion may also contain span 85 and/or Lecithin. Typically the oil in water will comprise from 2 to 10% squalene of the total volume of the immunogenic composition, from 2 to 10% alpha tocopherol and from 0.3 to 3% Tween 80, and may be produced according to the procedure described in WO 95/17210. Suitably the ratio of squalene: alpha tocopherol is equal or less than 1 as this provides a more stable emulsion. Span 85 (polyoxyethylene sorbitan trioleate) may also be present, for example at a level of 1%.

Immunogenic Properties of the Immunogenic Composition Used for the First Vaccination of the Present Invention In the present invention the monovalent influenza composition is capable of inducing an improved CD4 T-cell immune response against at least one of the component antigen(s) or antigenic composition compared to the CD4 T-cell immune response obtained with the corresponding composition which in un-adjuvanted, i.e. does not contain any exogeneous adjuvant (herein also referred to as 'plain composition'). In a specific embodiment, said improved CD4 T-cell immune response is against the pandemic influenza strain.

By 'improved CD4 T-cell immune response is meant that a higher CD4 response is obtained in a human patient after administration of the adjuvanted immunogenic composition than that obtained after administration of the same composition without adjuvant. For example, a higher CD4 T-cell response is obtained in a human patient upon administration of an immunogenic composition comprising an influenza virus or antigenic preparation thereof together with an oil-in-water emulsion adjuvant comprising a metabolisable oil, a tocopherol, such as alpha tocopherol, and an emulsifying agent, compared to the response induced after administration of an immunogenic composition comprising an influenza virus or antigenic preparation thereof which is un-adjuvanted. Such formulation will advantageously be used to induce anti-influenza CD4-T cell response capable of detection of influenza epitopes presented by MHC class II molecules.

Suitably said immunological response induced by an adjuvanted split influenza composition for use in the present invention is higher than the immunological response induced by any other un-adjuvanted influenza conventional vaccine, such as sub-unit influenza vaccine or whole influenza virus vaccine.

In particular but not exclusively, said 'improved CD4 T-cell immune response' is obtained in an immunologically unprimed patient, i.e. a patient who is seronegative to said influenza virus or antigen. This seronegativity may be the result of said patient having never faced such virus or antigen (so-called 'naive' patient) or, alternatively, having failed to respond to said antigen once encountered. Suitably said improved CD4 T-cell immune response is obtained in an immunocompromised subject such as an elderly, typically at least 50 years of age, typically 65 years of age or above, or an adult below 65 years of age with a high risk medical condition ('high risk' adult), or a child under the age of two.

The improved CD4 T-cell immune response may be assessed by measuring the number of cells producing any of the following cytokines:
- cells producing at least two different cytokines (CD40L, IL-2, IFNγ, TNFα)
- cells producing at least CD40L and another cytokine (IL-2, TNFα, IFNγ)
- cells producing at least IL-2 and another cytokine (CD40L, TNFα, IFNγ)
- cells producing at least IFNγ and another cytokine (IL-2, TNFα, CD40L)
- cells producing at least TNFα and another cytokine (IL-2, CD40L, IFNγ)

There will be improved CD4 T-cell immune response when cells producing any of the above cytokines will be in a higher amount following administration of the adjuvanted composition compared to the administration of the un-adjuvanted composition. Typically at least one, suitably two of the five conditions mentioned herein above will be fulfilled. In a particular embodiment, the cells producing all four cytokines will be present at a higher amount in the adjuvanted group compared to the un-adjuvanted group.

In a specific embodiment, an improved CD4 T-cell immune response may be conferred by the adjuvanted influenza composition of the present invention and may be ideally obtained after one single administration. The single dose approach will be extremely relevant for example in a rapidly evolving outbreak situation. In certain circumstances, especially for the elderly population, or in the case of young children (below 9 years of age) who are vaccinated for the first time against influenza, or in the case of a pandemics, it may be beneficial to administer two doses of the same composition for that season. The second dose of said same composition (still considered as 'composition for first vaccination') may be administered during the on-going primary immune response and is adequately spaced. Typically the second dose of the composition is given a few weeks, or about one month, e.g. 2 weeks, 3 weeks, 4 weeks, 5 weeks, or 6 weeks after the first dose, to help prime the immune system in unresponsive or poorly responsive individuals. In a specific aspect, the primo-vaccination is followed by a subsequent vaccination course of adjuvanted vaccine product containing a heterologous influenza strain.

In a specific embodiment, the administration of said immunogenic composition alternatively or additionally induces an improved B-memory cell response in patients administered with the adjuvanted immunogenic composition compared to the B-memory cell response induced in individuals immunized with the un-adjuvanted composition. An improved B-memory cell response is intended to mean an increased frequency of peripheral blood B lymphocytes capable of differentiation into antibody-secreting plasma cells upon antigen encounter as measured by stimulation of in-vitro differentiation (see Example sections, e.g. methods of Elispot B cells memory).

In a still further specific embodiment, the vaccination with the composition for the first vaccination, adjuvanted, has no measurable impact on the CD8 response.

Suitably, the claimed composition comprising an influenza virus or antigenic preparation thereof formulated with an oil-in-water emulsion adjuvant, in particular an oil-in-water emulsion adjuvant comprising a metabolisable oil, a sterol and/or a tocopherol, such as alpha tocopherol, and an emulsifying agent, will be effective in promoting T cell responses in an immuno-compromised human population. Suitably, the administration of a single dose of the immunogenic composition for first vaccination, as described in the invention will be capable of providing better sero-protection, as assessed by the correlates of protection for influenza vaccines, following revaccination against influenza, than does the vaccination with an un-adjuvanted influenza vaccine. The claimed adjuvanted formulation will also induce an improved CD4 T-cell immune response against influenza virus compared to that obtained with the un-adjuvanted formulation. This property can be associated with an increased responsiveness upon vaccination or infection vis-à-vis influenza antigenic exposure. Furthermore, this may also be associated with a cross-responsiveness, i.e. a higher ability to respond against variant influenza strains. This qualitatively and/or quantitatively improved response may be beneficial in all populations in the case of pandemics, and especially in an immuno-compromised human population such as the elderly population (65 years of age and above) and in particular the high risk elderly population. This may also be of benefit to the infant population (below 5 years, suitably below 2 years of age). This improved response will be of benefit for usage for priming e.g. from stockpiled vaccine containing a drift variant, before or at onset of pandemic outbreak. This may result in reducing the overall morbidity and mortality rate and preventing emergency admissions to hospital for pneumonia and other influenza-like illness. Furthermore it allows inducing a CD4 T cell response which is more persistent in time, e.g. still present one year after the first vaccination, compared to the response induced with the un-adjuvanted formulation.

Suitably the CD4 T-cell immune response, such as the improved CD4 T-cell immune response obtained in an unprimed subject, involves the induction of a cross-reactive CD4 T helper response. In particular, the amount of cross-reactive CD4 T cells is increased. By 'cross-reactive' CD4 response is meant CD4 T-cell targeting shared epitopes between influenza strains.

Usually, available influenza vaccines are effective only against infecting strains of influenza virus that have haemagglutinin of similar antigenic characteristics. When the infecting (circulating) influenza virus has undergone minor changes (such as a point mutation or an accumulation of point mutations resulting in amino acid changes in the for example) in the surface glycoproteins in particular haemagglutinin (antigenic drift variant virus strain) the vaccine may still provide some protection, although it may only provide limited protection as the newly created variants may escape immunity induced by prior influenza infection or vaccination. Antigenic drift is responsible for annual epidemics that occur during interpandemic periods (Wiley & Skehel, 1987, Ann. Rev. Biochem. 56, 365-394). The induction of cross-reactive CD4 T cells provides an additional advantage to the composition of the invention, in that it may provide also cross-protection, in other words protection against heterologous infections, i.e. infections caused by a circulating influenza strain which is a variant (e.g. a drift) of the influenza strain contained in the immunogenic composition. This may be advantageous when the circulating strain is difficult to propagate in eggs or to produce in cell culture, rendering the use of a drifted strain a working alternative. This may also be advantageous when the subject received a first and a second vaccination several months or a year apart, and the influenza strain in the immunogenic composition used for a second immunization is a drift variant strain of the strain used in the composition used for the first vaccination.

The adjuvanted influenza immunogenic composition as herein defined has therefore a higher ability to induce sero-protection and cross-reactive CD4 T cells in vaccinated elderly subjects. This characteristic may be associated with a higher ability to respond against a variant strain of the strain present in the immunogenic composition. This may prove to be an important advantage in a pandemic situation. For example a monovalent influenza immunogenic composition comprising any of H5, a H2, a H9, H7 or H6 strain(s) may provide a higher ability to respond against a pandemic variant, i.e. a drift strain of said pandemic strain(s), either upon subsequent vaccination with or upon infection by said drift strain.

Detection of Cross-Reactive CD4 T-Cells Following Vaccination with Influenza Vaccine Following classical trivalent Influenza vaccine administration (3 weeks), there is a substantial increase in the frequency of peripheral blood CD4 T-cells responding to antigenic strain preparation (whole virus or split antigen) that is homologous to the one present in the vaccine (H3N2: A/Panama/2007/99, H1N1: A/New Caledonia/20/99, B: B/Shangdong/7/97) (see Example III). A comparable increase in frequency can be seen if peripheral blood CD4 T-cells are restimulated with influenza strains classified as drifted strains (H3N2: A/Sydney/5/97, H1N1: A/Beijing/262/95, B: B/Yamanashi/166/98).

In contrast, if peripheral blood CD4 T-cells are restimulated with influenza strains classified as shift strains (H2N2: A/Singapore/1/57, H9N2: A/Hongkong/1073/99) by expert in the field, there is no observable increase following vaccination.

CD4 T-cells that are able to recognize both homologous and drifted Influenza strains have been named in the present document "cross-reactive". The adjuvanted influenza compositions as described herein have been capable to show heterosubtypic cross-reactivity since there is observable cross-reactivity against drifted Influenza strains. As said above, the ability of a pandemic vaccine formulation to be effective against drift pandemic strains may prove to be an important characteristic in the case of pandemics.

Consistently with the above observations, CD4 T-cell epitopes shared by different Influenza strains have been identified in human (Gelder C et al. 1998, Int Immunol. 10(2):211-22; Gelder C M et al. 1996 J Virol. 70(7):4787-90; Gelder C M et al. 1995 J Virol. 1995 69(12):7497-506).

Due to its immunogenic properties, the claimed composition will be able to establish a proactive vaccination strategy against the threat of a human influenza pandemic, including the stockpiling of pre-pandemic vaccine in order to better prepare against the onset of a pandemic.

Specifically, the pre-pandemic vaccine is one that has been produced, for example through to use of reverse genetics, using a strain of H5N1 (avian flu) similar to the ones currently circulating in the bird population. The immunity developed in response to the pre-pandemic vaccine will allow the immune system to be 'primed' or 'educated' in readiness and thereby allowing for more rapid development of protective immune responses after encountering the actual pandemic virus strain leading to a decreased susceptibility to a related pandemic strain of the influenza. Once a pandemic has been declared by WHO and the final pandemic strain identified (be it a drift strain), the pre-pandemic vaccine will also allow a more rapid immune response to the pandemic vaccine when the latter becomes available.

In a specific embodiment, the adjuvanted composition may offer the additional benefit of providing better protection against circulating strains which have undergone a major change (such as gene recombination for example, between two different species) in the haemagglutinin (antigenic shift) against which currently available vaccines have no efficacy.

Other Adjuvants

The composition may comprise an additional adjuvant, in particular a TRL-4 ligand adjuvant, suitably a non-toxic derivative of lipid A. A suitable TRL-4 ligand is 3 de-O-acylated monophosphoryl lipid A (3D-MPL). Other suitable TLR-4 ligands are lipopolysaccharide (LPS) and derivatives, MDP (muramyl dipeptide) and F protein of RSV.

In one embodiment the composition may additionally include a Toll like receptor (TLR) 4 ligand, such as a non-toxic derivative of lipid A, particularly monophosphoryl lipid A or more particularly 3-Deacylated monophoshoryl lipid A (3D-MPL).

3D-MPL is sold under the trademark MPL® by Corixa corporation now GSK (herein MPL) and primarily promotes CD4+ T cell responses with an IFN-γ (Th1) phenotype. It can be produced according to the methods disclosed in GB 2 220 211 A. Chemically it is a mixture of 3-deacylated monophosphoryl lipid A with 3, 4, 5 or 6 acylated chains. In particular, in the compositions of the present invention small particle 3 D-MPL is used. Small particle 3D-MPL has a particle size such that it may be sterile-filtered through a 0.22 μm filter. Such preparations are described in WO94/21292 and in Example II.

3D-MPL can be used, for example, at an amount of 1 to 100 μg (w/v) per composition dose, suitably in an amount of 10 to 50 μg (w/v) per composition dose. A suitable amount of 3D-MPL is for example any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μg (w/v) per composition dose. Suitably, 3D-MPL amount ranges from 25 to 75 μg (w/v) per composition dose. Usually a composition dose will be ranging from about 0.5 ml to about 1 ml. A typical vaccine dose are 0.5 ml, 0.6 ml, 0.7 ml, 0.8 ml, 0.9 ml or 1 ml. In a suitable embodiment, a final concentration of 50 μg of 3D-MPL is contained per ml of vaccine composition, or 25 μg per 0.5 ml vaccine dose. In other suitable embodiments, a final concentration of 35.7 μg or 71.4 μg of 3D-MPL is contained per ml of vaccine composition. Specifically, a 0.5 ml vaccine dose volume contains 25 μg or 50 μg of 3D-MPL per dose.

The dose of MPL is suitably able to enhance an immune response to an antigen in a human. In particular a suitable MPL amount is that which improves the immunological potential of the composition compared to the unadjuvanted composition, or compared to the composition adjuvanted with another MPL amount, whilst being acceptable from a reactogenicity profile.

Synthetic derivatives of lipid A are known, some being described as TLR-4 agonists, and include, but are not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S, 9 R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S—, 9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Other suitable TLR-4 ligands are, for example, lipopolysaccharide and its derivatives, muramyl dipeptide (MDP) or F protein of respiratory syncitial virus.

Another suitable immunostimulant for use in the present invention is Quil A and its derivatives. Quil A is a saponin preparation isolated from the South American tree *Quilaja Saponaria* Molina and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, which induces CD8+ cytotoxic T cells (CTLs), Th1 cells and a predominant IgG2a antibody response and is a suitable saponin in the context of the present invention.

Particular formulations of QS21 have been described which are particularly suitable, these formulations further comprise a sterol (WO96/33739). The saponins forming part of the present invention may be in the form of an oil in water emulsion (WO 95/17210).

Revaccination and Composition Used for Revaccination (Boosting Composition)

An aspect of the present invention provides the use of an influenza antigen in the manufacture of an influenza immunogenic composition for revaccination of humans previously vaccinated with an monovalent influenza composition as claimed herein or with said monovalent influenza composition comprising a variant influenza strain, formulated with an oil-in-water emulsion adjuvant as herein defined.

Typically revaccination is made at least 1 month, suitably at least two months, suitably at least three months, or 4 months after the first vaccination, suitably 8 to 14 months after, suitably at around 10 to 12 months after or even longer. Suitably revaccination is made at least 6 months after the first vaccination(s), suitably 8 to 14 months after, suitably at around 10 to 12 months after.

The immunogenic composition for revaccination (the boosting composition) may contain any type of antigen preparation, either inactivated, recombinant or live attenuated. It may contain the same type of antigen preparation i.e. split influenza virus or split influenza virus antigenic preparation thereof, a whole virion, a purified HA and NA (sub-unit) vaccine or a virosome, as the immunogenic composition used for the first vaccination. Alternatively the boosting composition may contain another type of influenza antigen, i.e. split influenza virus or split influenza virus antigenic preparation thereof, a whole virion, a purified HA and NA (sub-unit) vaccine or a virosome, than that used for the first vaccination. Suitably a split virus or a whole virion vaccine is used.

Accordingly, in one embodiment, the invention provides for the use of an influenza virus or antigenic preparation thereof in the manufacture of an immunogenic composition for revaccination of humans previously vaccinated with a monovalent pandemic immunogenic composition as claimed herein.

The boosting composition may be adjuvanted or unadjuvanted. In one embodiment the composition for revaccination is not adjuvanted and is a classical influenza vaccine containing three inactivated split virion antigens prepared from the WHO recommended strains of the appropriate influenza season, such as Fluarix™/α-Rix®/Influsplit® or FluLaval™ given intramuscularly.

In another embodiment the composition for revaccination is adjuvanted. Suitably the boosting composition comprises an oil-in-water emulsion adjuvant, in particular an oil-in-water emulsion adjuvant comprising a metabolisable oil, a sterol and/or a tocopherol, such as alpha tocopherol, and an emulsifying agent. Specifically, said oil-in-water emulsion adjuvant comprises at least one metabolisable oil in an amount of 0.5% to 20% of the total volume, and has oil droplets of which at least 70% by intensity have diameters of less than 1 μm. Alternatively the boosting composition comprises an alum adjuvant, either aluminium hydroxide or aluminium phosphate or a mixture of both.

In one embodiment, the first vaccination is made with a pandemic influenza composition as herein defined, suitably a split influenza composition, and the revaccination is made as follows.

In a specific embodiment, the immunogenic composition for revaccination contains an influenza virus or antigenic preparation thereof which shares common CD4 T-cell epitopes with the influenza virus or antigenic preparation thereof used for the first vaccination. A common CD4 T cell epitope is intended to mean peptides/sequences/epitopes from different antigens which can be recognised by the same CD4 cell (see examples of described epitopes in: Gelder C et al. 1998, Int Immunol. 10(2):211-22; Gelder C M et al. 1996 J Virol. 70(7):4787-90; Gelder C M et al. 1995 J Virol. 1995 69(12):7497-506).

In an embodiment according to the invention, the boosting composition is a monovalent influenza composition comprising an influenza strain which is associated with a pandemic or has the potential to be associated with a pandemic. Suitable strains are, but not limited to: H5N1, H9N2, H7N7, H2N2, H7N1 and H1N1. Said strain may be the same as that, or one of those, present in the composition used for the first vaccination. In an alternative embodiment said strain may be a variant strain, i.e. a drift strain, of the strain present in the composition used for the first vaccination.

In another specific embodiment, the composition for revaccination is a multivalent influenza vaccine. In particular, when the boosting composition is a multivalent vaccine such as a bivalent, trivalent or quadrivalent vaccine, at least one strain is associated with a pandemic or has the potential to be associated with a pandemic. In a specific embodiment, two or more strains in the boosting composition are pandemic strains. In another specific embodiment, the at least one pandemic strain in the boosting composition is of the same type as that, or one of those, present in the composition used for the first vaccination. In an alternative embodiment the at least one strain may be a variant strain, i.e. a drift strain, of the at least one pandemic strain present in the composition used for the first vaccination.

Accordingly, in another aspect of the present invention, there is provided the use of an influenza virus or antigenic preparation thereof, from a first pandemic influenza strain, in the manufacture of an immunogenic composition as herein defined, for protection against influenza infections caused by a influenza strain which is a variant of said first influenza strain.

Accordingly, in another aspect of the present invention, there is provided the use of:

(a) an influenza virus or antigenic preparation thereof, from a first influenza strain, and (b) an oil-in-water emulsion adjuvant as herein defined in the manufacture of an immunogenic composition as herein defined, for protection against influenza infections caused by a influenza strain which is a variant of said first influenza strain.

The composition for revaccination may be adjuvanted or not.

Typically a boosting composition, where used, is given at the next influenza season, e.g. approximately one year after the first immunogenic composition. The boosting composition may also be given every subsequent year (third, fourth, fifth vaccination and so forth). The boosting composition may be the same as the composition used for the first vaccination. Suitably, the boosting composition contains an influenza virus or antigenic preparation thereof which is a variant strain of the influenza virus used for the first vaccination. In particular, the influenza viral strains or antigenic preparation thereof are selected according to the reference material distributed by the World Health Organisation such that they are adapted to the influenza strain which is circulating on the year of the revaccination. Suitably the first vaccination is made at the declaration of a pandemic and revaccination is made later. Suitably, the revaccination is made with a vaccine comprising an influenza strain (e.g. H5N1 Vietnam) which is of the same subtype as that used for the first vaccination (e.g. H5N1 Vietnam). In a specific embodiment, the revaccination is made with a drift strain of the same sub-type, e.g. H5N1 Indonesia. In another embodiment, said influenza strain used for the revaccination is a shift strain, i.e. is different from that used for the first vaccination, e.g. it has a different HA or NA subtype, such as H5N2 (same HA subtype as H5N1 but different NA subtype) or H7N1 (different HA subtype from H5N1 but same NA subtype).

The influenza antigen or antigenic composition used in revaccination suitably comprises an adjuvant or an oil-in-water emulsion, suitably as described above. The adjuvant may be an oil-in-water emulsion adjuvant as herein above described, which is suitable, optionally containing an additional adjuvant such as TLR-4 ligand such as 3D-MPL or a saponin, or may be another suitable adjuvant such as alum or alum alternatives such as polyphosphazene for example.

Suitably revaccination induces any, suitably two or all, of the following: (i) an improved CD4 response against the influenza virus or antigenic preparation thereof, or (ii) an improved B cell memory response or (iii) an improved humoral response, compared to the equivalent response induced after a first vaccination with the un-adjuvanted influenza virus or antigenic preparation thereof. Suitably the immunological responses induced after revaccination with the adjuvanted influenza virus or antigenic preparation thereof as herein defined, are higher than the corresponding response induced after the revaccination with the un-adjuvanted composition. Suitably the immunological responses induced after revaccination with an un-adjuvanted, suitably split, influenza virus are higher in the population first vaccinated with the adjuvanted, suitably split, influenza composition than the corresponding response in the population first vaccinated with the un-adjuvanted, suitably split, influenza composition.

In one aspect according to the invention, the revaccination of the subjects with a boosting composition comprising an influenza virus and an oil-in-water emulsion adjuvant comprising a metabolisable oil, a sterol and/or a tocopherol, such as alpha tocopherol, and an emulsifying agent, as defined herein above, will show higher antibody titers than the corresponding values in the group of people first vaccinated with the un-adjuvanted composition and boosted with the un-adjuvanted composition. The effect of the adjuvant in enhancing the antibody response to revaccination is especially of importance in the elderly population which is known to have a low response to vaccination or infection by influenza virus. In particular, the adjuvanted composition-associated benefit will also be marked in terms of improving the CD4 T-cell response following revaccination.

The adjuvanted composition of the invention will be capable of inducing a better cross-responsiveness against drifted strain (the influenza strain from the next influenza season) compared to the protection conferred by the control vaccine. Said cross-responsiveness has shown a higher persistence compared to that obtained with the un-adjuvanted formulation. The effect of the adjuvant in enhancing the cross-responsiveness against drifted strain is of important in a pandemic situation.

In a further embodiment the invention relates to a vaccination regime in which the first vaccination is made with an influenza composition, suitably a split influenza composition, containing an influenza strain that could potentially cause a pandemic and the revaccination is made with a composition, either monovalent or multivalent, comprising at least one circulating strain, either a pandemic strain or a classical strain.

CD4 Epitope in HA

This antigenic drift mainly resides in epitope regions of the viral surface proteins haemagglutinin (HA) and neuraminidase (NA). It is known that any difference in CD4 and B cell epitopes between different influenza strains, being used by the virus to evade the adaptive response of the host immune system, will play a major role in influenza vaccination.

CD4 T-cell epitopes shared by different Influenza strains have been identified in human (see for example: Gelder C et al. 1998, Int Immunol. 10(2):211-22; Gelder C M et al. 1996 J Virol. 70(7):4787-90; and Gelder C M et al. 1995 J Virol. 1995 69(12):7497-506).

In a specific embodiment, the revaccination is made by using a boosting composition which contains an influenza virus or antigenic preparation thereof which shares common CD4 T-cell epitopes with the influenza virus antigen or antigenic preparation thereof used for the first vaccination. The invention thus relates to the use of the immunogenic composition comprising a pandemic influenza virus or antigenic preparation thereof and an oil-in-water emulsion adjuvant, in particular an oil-in-water emulsion adjuvant comprising a metabolisable oil, a sterol and/or a tocopherol, such as alpha tocopherol, and an emulsifying agent, in the manufacture of a first vaccination-component of a multi-dose vaccine, the multi-dose vaccine further comprising, as a boosting dose, an influenza virus or antigenic preparation thereof which shares common CD4 T-cell epitopes with the pandemic influenza virus antigen or virus antigenic preparation thereof of the dose given at the first vaccination.

Vaccination Means

The composition of the invention may be administered by any suitable delivery route, such as intradermal, mucosal e.g. intranasal, oral, intramuscular or subcutaneous. Other delivery routes are well known in the art.

The intramuscular delivery route is particularly suitable for the adjuvanted influenza composition. The composition according to the invention may be presented in a monodose container, or alternatively, a multidose container, particularly suitable for a pandemic vaccine. In this instance an antimicrobial preservative such a thiomersal is typically present to prevent contamination during use. Thiomersal concentration may be at 25 µg/0.5 ml dose (i.e. 50 µg/mL). A thiomersal concentration of 5 µg/0.5 ml dose (i.e. 10 µg/ml) or 10 µg/0.5 ml dose (i.e. 20 µg/ml) is suitably present. A suitable IM delivery device could be used such as a needle-free liquid jet injection device, for example the Biojector 2000 (Bioject, Portland, Oreg.). Alternatively a pen-injector device, such as is used for at-home delivery of epinephrine, could be used to allow self administration of vaccine. The use of such delivery devices may be particularly amenable to large scale immunization campaigns such as would be required during a pandemic.

Intradermal delivery is another suitable route. Any suitable device may be used for intradermal delivery, for example short needle devices such as those described in U.S. Pat. Nos. 4,886,499, 5,190,521, 5,328,483, 5,527,288, 4,270,537, 5,015,235, 5,141,496, 5,417,662. Intradermal vaccines may also be administered by devices which limit the effective penetration length of a needle into the skin, such as those described in WO99/34850 and EP1092444, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556 U.S. Pat. Nos. 4,790,824, 4,941,880, 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal administration.

Another suitable administration route is the subcutaneous route. Any suitable device may be used for subcutaneous delivery, for example classical needle. Suitably, a needle-free jet injector service is used, such as that published in WO 01/05453, WO 01/05452, WO 01/05451, WO 01/32243, WO 01/41840, WO 01/41839, WO 01/47585, WO 01/56637, WO 01/58512, WO 01/64269, WO 01/78810, WO 01/91835, WO 01/97884, WO 02/09796, WO 02/34317. Suitably said device is pre-filled with the liquid vaccine formulation.

Alternatively the vaccine is administered intranasally. Typically, the vaccine is administered locally to the nasopharyngeal area, suitably without being inhaled into the lungs. It is desirable to use an intranasal delivery device which delivers the vaccine formulation to the nasopharyngeal area, without or substantially without it entering the lungs.

Suitable devices for intranasal administration of the vaccines according to the invention are spray devices. Suitable commercially available nasal spray devices include Accuspray™ (Becton Dickinson). Nebulisers produce a very fine spray which can be easily inhaled into the lungs and therefore does not efficiently reach the nasal mucosa. Nebulisers are therefore not preferred.

Suitable spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO 91/13281 and EP 311 863 B and EP 516 636, incorporated herein by reference. Such devices are commercially available from Pfeiffer GmbH and are also described in Bommer, R. Pharmaceutical Technology Europe, September 1999.

Suitable intranasal devices produce droplets (measured using water as the liquid) in the range 1 to 200 μm, suitably 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Bi-dose delivery is a further suitable feature of an intranasal delivery system for use with the vaccines according to the invention. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a monodose device may be used for administering the vaccines according to the invention.

Alternatively, the epidermal or transdermal vaccination route is also contemplated in the present invention.

In one aspect of the present invention, the adjuvanted immunogenic composition for the first administration may be given intramuscularly, and the boosting composition, either adjuvanted or not, may be administered through a different route, for example intradermal, subcutaneous or intranasal. In a specific embodiment, the composition for the first administration contains a HA amount of less than 15 μg for the pandemic influenza strain, and the boosting composition may contain a standard amount of 15 μg or, suitably a low amount of HA, i.e. below 15 μg, which, depending on the administration route, may be given in a smaller volume.

Populations to Vaccinate

The target population to vaccinate is the entire population, e.g. healthy young adults (e.g. aged 18-60), elderly (typically aged above 60) or infants/children. The target population may in particular be immuno-compromised. Immunocompromised humans generally are less well able to respond to an antigen, in particular to an influenza antigen, in comparison to healthy adults.

In one aspect according to the invention, the target population is a population which is unprimed against influenza, either being naïve (such as vis à vis a pandemic strain), or having failed to respond previously to influenza infection or vaccination. Suitably the target population is elderly persons suitably aged at least 60, or 65 years and over, younger high-risk adults (i.e. between 18 and 60 years of age) such as people working in health institutions, or those young adults with a risk factor such as cardiovascular and pulmonary disease, or diabetes. Another target population is all children 6 months of age and over, especially children 6-23 months of age who experience a relatively high influenza-related hospitalization rate. Another target population is younger children from birth to 6 months of age.

Vaccination Regimes, Dosing and Efficacy Criteria

Suitably the immunogenic compositions according to the present invention are a standard 0.5 ml injectable dose in most cases, and contains less than 15 μg of haemagglutinin antigen component from a pandemic influenza strain, as measured by single radial immunodiffusion (SRD) (J. M. Wood et al.: J. Biol. Stand. 5 (1977) 237-247; J. M. Wood et al., J. Biol. Stand. 9 (1981) 317-330). Suitably the vaccine dose volume will be between 0.5 ml and 1 ml, in particular a standard 0.5 ml, or 0.7 ml vaccine dose volume. Slight adaptation of the dose volume will be made routinely depending on the HA concentration in the original bulk sample and depending also on the delivery route with smaller doses being given by the intranasal or intradermal route.

Suitably said immunogenic composition contains a low amount of HA antigen—e.g any of 1, 2, 3, 4, 5, 6, 7, 8, 9, 10, 11, 12, 13, 14 μg of HA per influenza strain or which does not exceed 15 μg of HA per strain. Said low amount of HA amount may be as low as practically feasible provided that it allows to formulate a vaccine which meets the international e.g. EU or FDA criteria for efficacy, as detailed below (see Table 1 and the specific parameters as set forth).

A suitable low amount of HA is between 1 to 7.5 µg of HA per influenza strain, suitably between 3.5 to 5 µg such as 3.75 or 3.8 µg of HA per influenza strain, typically about 5 µg of HA per influenza strain. Another suitable amount of HA is between 0.1 and 5 µg of HA per influenza strain, suitably between 1.0 and 2 µg of HA per influenza strain such as 1.9 µg of HA per influenza strain.

Advantageously, a vaccine dose according to the invention, in particular a low HA amount vaccine, may be provided in a smaller volume than the conventional injected split flu vaccines, which are generally around 0.5, 0.7 or 1 ml per dose. The low volume doses according to the invention are suitably below 500 typically below 300 µl and suitably not more than about 200 µl or less per dose.

Thus, a suitable low volume vaccine dose according to one aspect of the invention is a dose with a low antigen dose in a low volume, e.g. about 15 µg or about 7.5 µg HA or about 3.0 µg HA (per strain) in a volume of about 200 µl.

The influenza medicament of the invention suitably meets certain international criteria for vaccines. Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). *Note for harmonization of requirements for influenza vaccines*, 1997. CHMP/BWP/214/96 circular No 96-0666:1-22) for clinical trials related to annual licensing procedures of influenza vaccines (Table 1). The requirements are different for adult populations (18-60 years) and elderly populations (>60 years) (Table 1). For interpandemic influenza vaccines, at least one of the assessments (seroconversion factor, seroconversion rate, seroprotection rate) should meet the European requirements, for all strains of influenza included in the vaccine. The proportion of titres equal or greater than 1:40 is regarded most relevant because these titres are expected to be the best correlate of protection [Beyer W et al. 1998. Clin Drug Invest.; 15:1-12].

As specified in the "Guideline on dossier structure and content for pandemic influenza vaccine marketing authorisation. (CHMP/VEG/4717/03, Apr. 5, 2004, or more recently EMEA/CHMP/VWP/263499/2006 of 24 Jan. 2007 entitled 'Guidelines on flu vaccines prepared from viruses with a potential to cause a pandemic', available on www.emea.eu.int), in the absence of specific criteria for influenza vaccines derived from non circulating strains, it is anticipated that a pandemic candidate vaccine should (at least) be able to elicit sufficient immunological responses to meet suitably all three of the current standards set for existing vaccines in unprimed adults or elderly subjects, after two doses of vaccine. The EMEA Guideline describes the situation that in case of a pandemic the population will be immunologically naive and therefore it is assumed that all three CHMP criteria for seasonal vaccines will be fulfilled by pandemic candidate vaccines. No explicit requirement to prove it in pre-vaccination seronegative subjects is required.

The compositions of the present invention suitably meet at least one such criteria for the pandemic strain included in the composition (one criteria is enough to obtain approval), suitably at least two, or typically at least all three criteria for protection as set forth in Table 1A.

TABLE 1A (CHMP criteria)

|  | 18-60 years | >60 years |
|---|---|---|
| Seroconversion rate* | >40% | >30% |
| Conversion factor** | >2.5 | >2.0 |
| Protection rate*** | >70% | >60% |

*Seroconversion rate is defined as the proportion of subjects in each group having a protective post-vaccination titre ≥1:40. The seroconversion rate simply put is the % of subjects who have an HI titre before vaccination of <1:10 and ≥1:40 after vaccination. However, if the initial titre is ≥1:10 then there needs to be at least a fourfold increase in the amount of antibody after vaccination.
**Conversion factor is defined as the fold increase in serum HI geometric mean titres (GMTs) after vaccination, for each vaccine strain.
***Protection rate is defined as the proportion of subjects who were either seronegative prior to vaccination and have a (protective) post-vaccination HI titre of ≥1:40 or who were seropositive prior to vaccination and have a significant 4-fold increase in titre post-vaccination; it is normally accepted as indicating protection.

A 70% seroprotection rate is defined by the European health regulatory authority (CHMP—Committee for Medicinal Products for Human Use) is one of three criteria normally required to be met for an annual seasonal influenza vaccine and which CHMP is also expecting a pandemic candidate vaccine to meet. However, mathematical modelling has indicated that a vaccine that is, at the population level, only 30% efficient against certain drifted strains may also be of benefit in helping to reduce the magnitude of a pandemic and that a pandemic vaccination campaign using a (pre-pandemic) vaccine with 30% efficacy against the pandemic strain (cross-protection of 30%) could effectively reduce the clinical attack rate by 75% and consequently morbidity/mortality within the population (Ferguson et al, Nature 2006).

FDA has published a draft guidance (CBER draft criteria) (available from the Office of Communication, Training and Manufacturers Assistance (HFM-40), 1401 Rockville Pike, Suite 200N, Rockville, Md. 20852-1448, or by calling 1-800-835-4709 or 301-827-1800, or from the Internet at http://www.fda.gov/cber/guidelines.htm) on Clinical Data Needed to Support the Licensure of Pandemic Influenza Vaccines, and the proposed criteria are also based on the CHMP criteria. FDA uses slightly different age cut-off points. Appropriate endpoints similarly include: 1) the percent of subjects achieving an HI antibody titer 1:40, and 2) rates of seroconversion, defined as a four-fold rise in HI antibody titer post-vaccination. The geometric mean titer (GMT) should be included in the results, but the data should include not only the point estimate, but also the lower bound of the 95% confidence interval of the incidence rate of seroconversion, and the day 42 incidence rate of HI titers ≥1:40 must exceed the target value. These data and the 95% confidence intervals (CI) of the point estimates of these evaluations should therefore be provided. FDA draft guidance requires that both targets be met. This is summarised in Table 1B.

TABLE 1B (CBER draft criteria)

|  | 18-64 years | >64 years |
|---|---|---|
| Seroconversion rate * | >40% | >30% |
| Rate of HI titers ≥1:40 | >70% | >60% |

* The seroconversion rate is is defined as: a) for subjects with a baseline titer ≥1:10, a 4-fold or greater rise; or b) for subjects with a baseline titer <1:10, a rise to ≥1:40. These criteria must be met at the lower bound of the 95% CI for the true value.

Accordingly, in one aspect of the invention, it is provided for a composition, method or use as claimed herein wherein said immune response or protection induced by the administration of the contemplated pandemic composition meets all three EU regulatory criteria for influenza vaccine efficacy. Suitably at least one, suitably two, or three of following criteria are met for the pandemic strain of the composition:
- a seroconversion rate of >50%, of >60%, of >70%, suitably of >80% or >90% in the adult population (aged 18-60), and/or suitably also in the elderly population (aged >60 years);
- a protection rate of >75%, of >80%, of >85%, suitably of >90% in the adult population (aged 18-60), and/or suitably also in the elderly population (aged >60 years);
- a conversion factor of >4.0, of >5.0, of >6.0, of >7.0, of >8.0, of >9.0 or of 10 or above 10 in the adult population (aged 18-60), and/or suitably also in the elderly population (aged >60 years).

In a specific embodiment the composition according to the invention will meet both a seroconversion rate of >60%, or >70%, or suitably >80% and a protection rate of >75%, suitably of >80% in the adult population. In another specific embodiment the composition according to the invention will meet both a conversion factor of >5.0, or >7.0 or suitably >10.0 and a seroconversion rate of >60%, or >70%, or suitably >80% in the adult population. In another specific embodiment, the composition according to the invention will meet both a conversion factor of >5.0, or >7.0 or suitably >10.0, and a protection rate of >75%, suitably >80% in the adult population. In still another specific embodiment the composition according to the invention will meet both a conversion factor of 10.0 or above, a seroconversion rate of 80% or above, and a protection rate of 80% or above.

In another embodiment, the claimed vaccine, suitably a pre-pandemic vaccine, will have 30% efficacy against the circulating pandemic strain (cross-protection of 30%). In particular the claimed vaccine will meet a seroprotection rate of at least 30% against drifted strains, suitably of at least 40%, or >50% or >60% against drifted strains. Suitably the seroprotection rate will be >70%, or suitably >80% against drift strains. Said pre-pandemic vaccine, capable of conferring cross-protection, will be able to reduce substantially the overall infection attack rate, by at least 50%, or suitably at least 75%, and consequently morbidity/mortality within the population.

In still another embodiment, the claimed adjuvanted vaccine is able to induce neutralizing antibodies in at least 50% of subjects, at least 60%, suitable at least 70%, or suitably in more than 75% of subjects against a drifted strain or a strain from a different clade. Suitably this effect is achieved with a low dose of antigen, such as with 7.5 µg HA or even a lower antigen dose such as 3.8 µg or 1.9 µg of HA.

Suitably any or all of such criteria are also met for other populations, such as in children and in any immuno-compromised population.

Suitably the above response(s) is(are) obtained after one dose, or typically after two doses. It is a particular advantage of the claimed composition that the immune response is obtained after only one dose of adjuvanted vaccine. Accordingly, there is provided in one aspect of the invention the use of a non-live pandemic influenza virus antigen preparation, in particular a split influenza virus preparation, in the manufacture of a vaccine composition for a one-dose vaccination against influenza, wherein the one-dose vaccination generates an immune response which meets at least one, suitably two or three, international regulatory requirements for influenza vaccines. In another particular embodiment said one-dose vaccination also or additionally generates a CD4 T cell immune response and/or a B cell memory response which is higher than that obtained with the non adjuvanted vaccine. In a particular embodiment said immune response is a cross-reactive antibody response or a cross-reactive CD4 T cell response or both. In a specific embodiment the human patient is immunologically naïve (i.e. does not have pre-existing immunity) to the vaccinating strain. Specifically the vaccine composition contains a low HA antigen amount. Specifically the vaccine composition is as defined herein. In particular the immunogenic properties of the vaccine composition are as defined herein. Suitably the vaccine is administered intramuscularly.

In respect of the composition for revaccination, when it is a multivalent composition, at least two or all three of the criteria will need to be met for all strains, particularly for a new vaccine such as a new vaccine for delivery via a different route. Under some circumstances two criteria may be sufficient. For example, it may be acceptable for two of the three criteria to be met by all strains while the third criterion is met by some but not all strains (e.g. two out of three strains).

In a further aspect the invention provides a method of designing a vaccine for diseases known to be cured or treated through a CD4+ T cell activation, comprising
1) selecting an antigen containing CD4+ epitopes, and
2) combining said antigen with an oil-in-water emulsion adjuvant as defined herein above, wherein said vaccine upon administration in said mammal is capable of inducing an enhanced CD4 T cell response in said mammal.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance.

The invention will be further described by reference to the following, non-limiting, examples:

Example I describes immunological read-out methods used in mice, ferrets and human studies.

Example II describes the preparation and characterization of the oil in water emulsion and adjuvant formulations used in the studies exemplified.

Example III shows a pre-clinical evaluation of adjuvanted and un-adjuvanted influenza vaccines in ferrets.

Example IV describes a clinical trial in an adult population aged 18-60 years with a vaccine containing a split influenza antigen preparation from a pandemic H5N1 strain and AS03 adjuvant.

Example V shows a pre-clinical evaluation of adjuvanted and unadjuvanted split influenza vaccines (comprising H5N1 strain) in C57131/6 naive mice.

Example VI shows a pre-clinical evaluation of an adjuvanted pandemic split influenza vaccines (comprising H5N1 strain) after heterologous challenge in ferrets.

Example 1—Immunological Read-Out Methods

I.1. Ferrets Methods
Suitable methods are given below which are routinely used for experiments performed with seasonal strains. The skilled reader will understand that it may need some adaptation or optimization depending on the influenza strain used.

I.1.1. Hemagglutination Inhibition Test (HI)

Test Procedure.

Anti-Hemagglutinin antibody titers to the influenza virus strain are determined using the hemagglutination inhibition test (HI). The principle of the HI test is based on the ability of specific anti-Influenza antibodies to inhibit hemagglutination of horse red blood cells (RBC) by influenza virus hemagglutinin (HA). After pre-treatment of sera (cholera, RDE, heat inactivation, . . . ), two-fold dilutions of sera are incubated with 4 hemagglutination units of the influenza strain. Horse (adaptation: turkey, or horse) red blood cells are then added and the inhibition of agglutination is scored. The titers are expressed as the reciprocal of the highest dilution of serum that completely inhibited hemagglutination. As the first dilution of sera was 1:10, an undetectable level was scored as a titer equal to 5. More details can be found in the section 1.2.1. below.

I.1.2. Body Temperature Monitoring

Body temperature was registered by means of temperature sensors (Star Oddi, Iceland) implanted on Day −14 under anesthesia with ketamine-rompun-atropine mix (2.5%-0.25%-0.025%) via small incision in the linea alba into the peritoneal cavity. The wound was closed with stitches and inspected daily.

I.2.3. Viral Titration

Pharyngeal, nasal and rectal swabs were collected from all animals. Individual swabs were placed in 3 ml virus transport medium (VTM; sterile PBS or suitable isotonic solution such as Hank's BSS containing antibiotics (100 units/ml penicillin, 100 μg/ml streptomycin) and either 2% fetal bovine serum or 0.5% gelatin) and stored at −80° C. until analysis. After necropsy cranioventral, craniodorsal, caudoventral and caudodorsal sections of the right lung from each animal were weighed and stored at −80° C. until analysis. Lung sections were homogenized in 3 ml VTM. Viral titers were determined by means of H5N1-specific TaqMan PCR and virus titration culture on Madine Darby canine kidney (MDCK) cells.

For the TaqMan PCR, viral H5N1 Flu RNAs were extracted from ferret samples and then amplified by a quantitative RT-PCR assay using primers and probes designed in a conserved region of the Influenza genome. Data were expressed as Control Dilution Units (CDU) and $TCID_{50}$ per gram of lung tissue or per ml of swab, respectively. Control Dilution Units (CDU)—CDUs are determined from a standard curve produced from a stock of virus which is serially diluted, with each dilution undergoing nucleic acid extraction and Taqman PCR amplification in the same manner as test samples.

For the viral culture, serial dilutions of all samples were transferred to microtiter plates containing medium and MDCK cells and then incubated at 35° C. for 5-7 days. After incubation, the viral shedding titers were determined by "Reed and Muench" and expressed as Log TCID50 per gram of lun tissue or per ml of swab.

I.1.4. Neutralizing Antibody Assay

Neutralizing antibody measurements were conducted on thawed frozen serum samples. Virus neutralization by antibodies contained in the serum is determined in a microneutralization assay. The sera are used without further treatment in the assay. Each serum is tested in triplicate. A standardised amount of virus is mixed with serial dilutions of serum and incubated to allow binding of the antibodies to the virus. A cell suspension, containing a defined amount of MDCK cells is then added to the mixture of virus and antiserum and incubated at 33° C. After the incubation period, virus replication is visualised by hemagglutination of chicken red blood cells. The 50% neutralization titre of a serum is calculated by the method of Reed and Muench (Am. J; Hyg. 1938, 27: 493-497).

I.2. Assays for Assessing the Immune Response in Humans

I.2.1. Hemagglutination Inhibition Assay

The immune response was determined by measuring HI antibodies using the method described by the WHO Collaborating Centre for influenza, Centres for Disease Control, Atlanta, USA (1991).

Antibody titre measurements were conducted on thawed frozen serum samples with a standardised and comprehensively validated micromethod using 4 hemagglutination-inhibiting units (4 HIU) of the appropriate antigens and a 0.5% fowl (or 0.5% fowl and horse for H5N1) erythrocyte suspension. Non-specific serum inhibitors were removed by heat treatment and receptor-destroying enzyme.

The sera obtained were evaluated for HI antibody levels. Starting with an initial dilution of 1:10, a dilution series (by a factor of 2) was prepared up to an end dilution of 1:20480. The titration end-point was taken as the highest dilution step that showed complete inhibition (100%) of hemagglutination. All assays were performed in duplicate.

Adaptation for H5N1

Specific Description of HI Using Horse Erythrocytes:

Glycoproteins (haemaglutinins) are located in the viral envelope, and are able to agglutinate erythrocytes (red blood cells) of many species e.g. chicken.

The haemagglutination inhibition test is carried out in two steps:
1. Antigen-antibody reaction: the Influenza antigen (DTA, dialysis test antigen) reacts with the antibodies of the subject's serum.
2. Agglutination of excessive antigen: excessive antigen reacts with added red blood cells Erythrocytes of horses are used for the H5N1 Pandemic strains.

0.5% (end concentration) horse red blood cell suspension in phosphate buffer containing 0.5% BSA (bovine serum albumin, end concentration).

This suspension is prepared every day by washing red blood cell with the same phosphate buffer and a subsequent centrifugation step (10 min, 2000 rpm). This washing step has to be repeated once.

After the addition of the horse red blood cells to the reaction mix of patient/subject sera and virus suspension the plates have to be incubated at room temperature (RT, 20° C.+/−2° C.) for two hours due to the low sedimentation rate of the horse red blood cells.

I.2.2. Neuraminidase Inhibition Assay

The assay was performed in fetuin-coated microtitre plates. A 2-fold dilution series of the antiserum was prepared and mixed with a standardised amount of influenza A H3N2, H1N1 or influenza B virus. The test was based on the biological activity of the neuraminidase which enzymatically releases neuraminic acid from fetuin. After cleavage of the terminal neuraminic acid ß-D-glactose-N-acetyl-galactosamin was unmasked. Horseradish peroxidase (HRP)-labelled peanut agglutinin from *Arachis hypogaea*, which binds specifically to the galactose structures, was added to the wells. The amount of bound agglutinin can be detected and quantified in a substrate reaction with tetra-methylbenzidine (TMB) The highest antibody dilution that still inhibits the viral neuraminidase activity by at least 50% was indicated is the NI titre.

I.2.3. Neutralising Antibody Assay

Neutralising antibody measurements were conducted on thawed frozen serum samples. Virus neutralisation by antibodies contained in the serum is determined in a microneutralization assay. The sera are used without further treatment in the assay.

Each serum is tested in triplicate. A standardised amount of virus is mixed with serial dilutions of serum and incubated to allow binding of the antibodies to the virus. A cell suspension, containing a defined amount of MDCK cells is then added to the mixture of virus and antiserum and incubated at 33° C. After the incubation period, virus replication is visualised by hemagglutination of chicken red blood cells. The 50% neutralisation titre of a serum is calculated by the method of Reed and Muench (Am. J; Hyg. 1938, 27: 493-497).

I.2.4. Cell-Mediated Immunity was Evaluated by Cytokine Flow Cytometry (CFC)

Peripheral blood antigen-specific CD4 and CD8 T cells can be restimulated in vitro to produce IL-2, CD40L, TNF-alpha and IFN if incubated with their corresponding antigen. Consequently, antigen-specific CD4 and CD8 T cells can be enumerated by flow cytometry following conventional immunofluorescence labelling of cellular phenotype as well as intracellular cytokines production. In the present study, Influenza vaccine antigen are used as antigen to restimulate Influenza-specific T cells. Results are expressed as a frequency of cytokine(s)-positive CD4 or CD8 T cell within the CD4 or CD8 T cell sub-population.

I.2.5. Memory B Cells by ELISPOT

The ELISPOT technology allows the quantification of memory B cells specific to a given antigen. Memory B-cells can be induced to differentiate into plasma cells in vitro following cultivation with CpG for 5 days. In vitro generated antigen-specific plasma cells can therefore be enumerated using the ELISPOT assay. Briefly, in vitro generated plasma cells are incubated in culture plates coated with antigen. Antigen-specific plasma cells form antibody/antigen spots, which can be detected by conventional immuno-enzymatic procedure. In the present study, influenza vaccine strains or anti-human Immunoglobulins are used to coat culture plates in order to enumerate influenza-specific antibody or IgG secreting plasma cells, respectively. Results are expressed as a frequency of influenza-specific antibody secreting plasma cells within the IgG-producing plasma cells.

I.2.6. Statistical Methods

I.2.6.1. Primary Endpoints

Percentage, intensity and relationship to vaccination of solicited local and general signs and symptoms during a 7 day follow-up period (i.e. day of vaccination and 6 subsequent days) after vaccination and overall.

Percentage, intensity and relationship to vaccination of unsolicited local and general signs and symptoms during a 21 day follow-up period (i.e. day of vaccination and 20 subsequent days) after vaccination and overall.

Occurrence of serious adverse events during the entire study.

I.2.6.2. Secondary Endpoints

For the Humoral Immune Response:

Observed Variables:

At days 0 and 21: serum hemagglutination-inhibition (HI) and NI antibody titres, tested separately against each of the three influenza virus strains represented in the vaccine (anti-H1N1, anti-H3N2 & anti-B-antibodies).

At days 0 and 21: neutralising antibody titres, tested separately against each of the three influenza virus strains represented in the vaccine Derived Variables (with 95% Confidence Intervals):

Geometric mean titres (GMTs) of serum HI antibodies with 95% confidence intervals (95% CI) pre and post-vaccination Seroconversion rates* with 95% CI at day 21

Conversion factors** with 95% CI at day 21

Seroprotection rates*** with 95% CI at day 21

Serum NI antibody GMTs' (with 95% confidence intervals) at all timepoints.

*Seroconversion rate defined as the percentage of vaccinees who have at least a 4-fold increase in serum HI titres on day 21 compared to day 0, for each vaccine strain.

**Conversion factor defined as the fold increase in serum HI GMTs on day 21 compared to day 0, for each vaccine strain.

***Protection rate defined as the percentage of vaccinees with a serum HI titre=40 after vaccination (for each vaccine strain) that usually is accepted as indicating protection.

For the Cell Mediated Immune (CMI) Response

Observed Variable

At days 0 and 21: frequency of cytokine-positive CD4/CD8 cells per $10^6$ in different tests. Each test quantifies the response of CD4/CD8 T cell to:

Peptide Influenza (pf) antigen (the precise nature and origin of these antigens needs to be given/explained Split Influenza (sf) antigen Whole Influenza (wf) antigen.

Derived Variables:

cells producing at least two different cytokines (CD40L, IL-2, IFNγ, TNFα)

cells producing at least CD40L and another cytokine (IL-2, TNFα, IFNγ)

cells producing at least IL-2 and another cytokine (CD40L, TNFα, IFNγ)

cells producing at least IFNγ and another cytokine (IL-2, TNFα, CD40L)

cells producing at least TNFα and another cytokine (IL-2, CD40L, IFNγ)

I.3.5.3. Analysis of Immunogenicity

The immunogenicity analysis was based on the total vaccinated cohort. For each treatment group, the following parameters (with 95% confidence intervals) were calculated:

Geometric mean titres (GMTs) of HI and NI antibody titres at days 0 and 21

Geometric mean titres (GMTs) of neutralising antibody titres at days 0 and 21.

Conversion factors at day 21.

Seroconversion rates (SC) at day 21 defined as the percentage of vaccinees that have at least a 4-fold increase in serum HI titres on day 21 compared to day 0.

Protection rates at day 21 defined as the percentage of vaccinees with a serum HI titre=1:40.

The frequency of CD4/CD8 T-lymphocytes secreting in response was summarised (descriptive statistics) for each vaccination group, at each timepoint (Day 0, Day 21) and for each antigen (Peptide influenza (pf), split influenza (sf) and whole influenza (wf)).

Descriptive statistics in individual difference between timepoint (Post-Pre) responses fore each vaccination group and each antigen (pf, sf, and wf) at each 5 different tests.

A non-parametric test (Kruskall-Wallis test) was used to compare the location differences between the 3 groups and the statistical p-value was calculated for each antigen at each 5 different tests. All significance tests were two-tailed. P-values less than or equal to 0.05 were considered as statistically significant.

I.3. Mice Methods

I.3.1. Anti-H5N1 ELISA.

Quantitation of anti-H5N1 IgG antibody was performed by ELISA using Split H5N1 as coating. Virus and antibody solutions were used at 100 µl per well. Split virus H5N1 was diluted at a final concentration of 1 µg/ml in PBS and was adsorbed overnight at 4° C. to the wells of 96 wells microtiter plates (Maxisorb Immunoplate Nunc 439454). The plates were then incubated for 1 hour at 37° C. with 200 µl per well of PBS containing 1% BSA and 0.1% Tween 20 (saturation buffer). Twelve two-fold dilutions of sera in saturation buffer were added to the H5N1-coated plates and incubated for 1 h 30 at 37° C. The plates were washed four times with PBS 0.1% Tween 20. Peroxidase-conjugated anti-mouse IgG (Sigma A5278) diluted 1/1000 in PBS 1% BSA 0.1% Tween 20 was added to each well and incubated for 1 hour at 37° C. After a washing step, plates were incubated 20 min at 22° C. with a solution of o-phenyl-diamine (Sigma P4664) 0.04% $H_2O_2$ 0.03% in 0.1 M citrate buffer pH 4.2. The reaction was stopped with $H_2SO_4$ 2 N and microplates were read at 490-630 nm.

I.3.2. Hemagglutination Inhibition (HI) Assay.

The protocol used was adapted from the classical HI assay for determining anti-HA antibodies, and relied on the use of horse RBC.

Test Principle (Classical Procedure)

Anti-Hemagglutinin antibody titers to the three (seasonal) influenza virus strains are determined using the hemagglutination inhibition test (HI). The principle of the HI test is based on the ability of specific anti-Influenza antibodies to inhibit hemagglutination of red blood cells (RBC) by influenza virus hemagglutinin (HA). Heat inactivated sera are treated by Kaolin and RBC to remove non-specific inhibitors. After pretreatment, two-fold dilutions of sera are incubated with 4 hemagglutination units of each influenza strain. Red blood cells are then added and the inhibition of agglutination is scored. The titers are expressed as the reciprocal of the highest dilution of serum that completely inhibited hemagglutination. As the first dilution of sera is 1:20, an undetectable level is scored as a titer equal to 10.

Adaptation for H5N1 (Specific Description of HI Using Horse Erythrocytes)

Erythrocytes of horses are used for the H5N1 Pandemic strains. 0.5% (end concentration) horse red blood cell suspension in phosphate buffer containing 0.5% BSA (bovine serum albumin, end concentration). This suspension is prepared every day by washing red blood cell with the same phosphate buffer and a subsequent centrifugation step (10 min, 2000 rpm). This washing step has to be repeated once. After the addition of the horse red blood cells to the reaction mix of sera and virus suspension; the plates have to be incubated at room temperature (RT, 20° C.+1-2° C.) for two hours due to the low sedimentation rate of the horse red blood cells.

Statistical Analysis

Statistical analysis were performed on post vaccination HI titers using UNISTAT. The protocol applied for analysis of variance can be briefly described as follow:

☐ Log transformation of data

Shapiro-Wilk test on each population (group) in order to verify the normality of groups distribution Cochran test in order to verify the homogenicity of variance between the different populations (groups)

Analysis of variance on selected data.

Test for interaction of two-way ANOVA

Tukey-HSD Test for multiple comparisons

I.3.3. Intracellular Cytokine Staining (ICS).

This technique allows a quantification of antigen specific T lymphocytes on the basis of cytokine production: effector T cells and/or effector-memory T cells produce IFN-γ and/or central memory T cells produce IL-2.

Intracellular staining of cytokines of T cells was performed on PBMC 7 days after the immunization. Blood was collected from mice and pooled in heparinated medium RPMI+Add*. For blood, RPMI+Add-diluted PBL suspensions were layered onto a Lympholyte-Mammal gradient according to the recommended protocol (centrifuge 20 minutes at 2500 rpm and R.T.). The mononuclear cells at the interface were removed, washed 2-fold in RPMI+Add and PBMCs suspensions were adjusted to $10^7$ cells/ml in RPMI 5% fetal calf serum.

* Composition of RMPI+Add

RPMI 1640 without L-glutamine (Gibco 31870-025/041-01870M)+Additives (for 500 ml RPMI): 5 ml sodium pyruvate 100 mM (Gibco lot 11360-039), 5 ml MEM non essential amino acids ((Gibco lot 11140-035), 5 ml Pen/Strep (Gibco lot 20F9252), 5 ml glutamine (Gibco lot 24Q0803), 500 μl 2-mercaptoethanol 1000× (Gibco ref. 31350-010).

In vitro antigen stimulation of PBMCs was carried out at a final concentration of $10^6$ cells/wells (microplate) with Formalin-inactivated split 1 μg HA/strain and then incubated 2 hours at 37° C. with the addition of anti-CD28 and anti-CD49d (1 μg/ml for the both). The addition of both antibodies increased proliferation and cytokine production by activated T and NK cells and can provide a costimulatory signal for CTL induction.

Following the antigen restimulation step, PBMC are incubated O.N. at 37° C. in presence of Brefeldin (1 μg/ml) at 37° C. to inhibit cytokine secretion. IFN-γ/IL-2/CD4/CD8 staining was performed as follows: cell suspensions were washed, resuspended in 50 μl of PBS 1% FCS containing 2% Fc blocking reagent (1/50; 2.4G2). After 10 minutes incubation at 4° C., 50 μl of a mixture of anti-CD4-PE (2/50) and anti-CD8 perCp (3/50) was added and incubated 30 minutes at 4° C. After a washing in PBS 1% FCS, cells were permeabilized by resuspending in 200 μl of Cytofix-Cytoperm (Kit BD) and incubated 20 minutes at 4° C. Cells were then washed with Perm Wash (Kit BD) and resuspended with 50 μl of a mix of anti-IFN-γ APC (1/50)+anti-IL-2 FITC (1/50) diluted in Perm Wash. After incubation (minimum 2 hours and maximum overnight) at 4° C., cells were washed with Perm Wash and resuspended in PBS 1% FCS+1% paraformaldehyde. Sample analysis was performed by FACS. Live cells were gated (FSC/SSC) and acquisition was performed on ~50,000 events (lymphocytes) or 15,000 events on CD4+ T cells. The percentages of IFN-γ+ or IL2+ were calculated on CD4+ and CD8+ gated populations.

Example II—Preparation and Characterization of the Oil in Water Emulsion and Adjuvant Formulations Unless otherwise stated, the oil/water emulsion used in the subsequent examples is composed an organic phase made of 2 oils (alpha-tocopherol and squalene), and an aqueous phase of PBS containing Tween 80 as emulsifying agent. Unless otherwise stated, the oil in water emulsion adjuvant formulations used in the subsequent examples were made comprising the following oil in water emulsion component (final concentrations given): 2.5% squalene (v/v), 2.5% alpha-tocopherol (v/v), 0.9% polyoxyethylene sorbitan monooleate (v/v) (Tween 80), see WO 95/17210. This emulsion, termed AS03 in the subsequent examples, was prepared as followed as a two-fold concentrate.

II.1. Preparation of Emulsion SB62

II.1.1. Lab-Scale Preparation

Tween 80 is dissolved in phosphate buffered saline (PBS) to give a 2% solution in the PBS. To provide 100 ml two-fold concentrate emulsion 5 g of DL alpha tocopherol and 5 ml of squalene are vortexed to mix thoroughly. 90 ml of PBS/Tween solution is added and mixed thoroughly. The resulting emulsion is then passed through a syringe and finally microfluidised by using an M110S microfluidics machine. The resulting oil droplets have a size of approximately 120-180 nm (expressed as Z average measured by PCS).

The other adjuvants/antigen components are added to the emulsion in simple admixture.

II.1.2. Scaled-Up Preparation

This method was used in the studies reported in the clinical and pre-clinical examples sections. The preparation of the SB62 emulsion is made by mixing under strong agitation of an oil phase composed of hydrophobic components (α-tocopherol and squalene) and an aqueous phase containing the water soluble components (Tween 80 and PBS mod (modified), pH 6.8). While stirring, the oil phase (1/10 total volume) is transferred to the aqueous phase (9/10 total volume), and the mixture is stirred for 15 minutes at room temperature. The resulting mixture then subjected to shear, impact and cavitation forces in the interaction chamber of a microfluidizer (15000 PSI—8 cycles) to produce submicron droplets (distribution between 100 and 200 nm). The resulting pH is between 6.8±0.1. The SB62 emulsion is then sterilised by filtration through a 0.22 μm membrane and the sterile bulk emulsion is stored refrigerated in Cupac containers at 2 to 8° C. Sterile inert gas (nitrogen or argon) is flushed into the dead volume of the SB62 emulsion final bulk container for at least 15 seconds.

The final composition of the SB62 emulsion is as follows:
Tween 80: 1.8% (v/v) 19.4 mg/ml; Squalene: 5% (v/v) 42.8 mg/ml; α-tocopherol: 5 (v/v) 47.5 mg/ml; PBS-mod: NaCl 121 mM, KCl 2.38 mM, Na2HPO4 7.14 mM, KH2PO4 1.3 mM; pH 6.8±0.1.

II.2. Measure of Oil Droplet Size Dynamic Light Scattering

II.2.1. Introduction

The size of the diameter of the oil droplets is determined according to the following procedure and under the following experimental conditions. The droplet size measure is given as an intensity measure and expressed as z average measured by PCS.

II.2.2. Sample Preparation

Size measurements have been performed on the oil-in-water emulsion adjuvant: SB62 prepared following the scaled-up method, AS03 and AS03+MPL (50 μg/ml), the last two being prepared just before use. The composition of the samples is given below (see section II.2.4). Samples were diluted 4000×-8000× in PBS 7.4.

As a control, PL-Nanocal Particle size standards 100 nm (cat no 6011-1015) was diluted in 10 mM NaCl.

II.2.3. Malvern Zetasizer 3000HS Size Measurements

All size measurements were performed with both Malvern Zetasizer 3000HS.

Samples were measured into a plastic cuvette for Malvern analysis at a suitable dilution (usually at a dilution of 4000× to 20000× depending on the sample concentration), and with two optical models:

- either real particle refractive index of 0 and imaginary one of 0.
- or real particle refractive index of 1.5 and imaginary one of 0.01 (the adapted optical model for the emulsion, according to the values found in literature).

The technical conditions were:

laser wavelength: 532 nm (Zeta3000HS).
laser power: 50 mW (Zeta3000HS).
scattered light detected at 90° (Zeta3000HS).
temperature: 25° C.,
duration: automatic determination by the soft,
number: 3 consecutive measurements,
z-average diameter: by cumulants analysis
size distribution: by the Contin or the Automatic method.

The Automatic Malvern algorithm uses a combination of cumulants, Contin and non negative least squares (NNLS) algorithms.

The intensity distribution may be converted into volume distribution thanks to the Mie theory.

II.2.4. Results (See Table 2)

Cumulants Analysis (Z Average Diameter):

TABLE 2

| Sample | Dilution | Record | Count rate | ZAD | Polydispersity |
|---|---|---|---|---|---|
| SB62 | 5000 | 1 | 7987 | 153 | 0.06 |
| | | 2 | 7520 | 153 | 0.06 |
| | | 3 | 6586 | 152 | 0.07 |
| | | average | 7364 | 153 | 0.06 |
| SB62 | 8000 | 1 | 8640 | 151 | 0.03 |
| (Example IV) | | 2 | 8656 | 151 | 0.00 |
| | | 3 | 8634 | 150 | 0.00 |
| | | average | 8643 | 151 | 0.01 |
| SB62 + MPL | 8000 | 1 | 8720 | 154 | 0.03 |
| 25 μg (*) | | 2 | 8659 | 151 | 0.03 |
| | | 3 | 8710 | 152 | 0.02 |
| | | average | 8697 | 152 | 0.02 |

(*) Prepared as follows: Water for injection, PBS 10x concentrated, 250 μl of SB62 emulsion and 25 μg of MPL are mixed together to reach a final volume of 280 μl.

The z-average diameter (ZAD) size is weighed by the amount of light scattered by each size of particles in the sample. This value is related to a monomodal analysis of the sample and is mainly used for reproducibility purposes.

The count rate (CR) is a measure of scattered light: it corresponds to thousands of photons per second.

The polydispersity (Poly) index is the width of the distribution. This is a dimensionless measure of the distribution broadness.

Contin and Automatic Analysis:

Two other SB62 preparations (2 fold concentrated AS03) have been made and assessed according to the procedure explained above with the following minor modifications: Samples were measured into a plastic cuvette for Malvern analysis, at two dilutions determined to obtain an optimal count rate values: 10000× and 20000× for the Zetasizer 3000HS, the same optical models as used in the above example.

Results are shown in Table 3.

TABLE 3

| SB62 | Dilution | IR Real | IR Imaginary | Analysis in Contin (mean in nm) Intensity | Analysis in Contin (mean in nm) Volume | Analysis in Automatic (mean in nm) Intensity | Analysis in Automatic (mean in nm) Volume |
|---|---|---|---|---|---|---|---|
| 1022 | 1/10000 | 0 | 0 | 149 | 167 | 150 | — |
|  |  | 1.5 | 0.01 | 158 | 139 | 155 | 143 |
|  | 1/20000 | 0 | 0 | 159 | 200 | 155 | 196 |
|  |  | 1.5 | 0.01 | 161 | 141 | 147 | — |
| 1023 | 1/10000 | 0 | 0 | 158 | 198 | 155 | — |
|  |  | 1.5 | 0.01 | 161 | 140 | 150 | 144 |
|  | 1/20000 | 0 | 0 | 154 | 185 | 151 | 182 |
|  |  | 1.5 | 0.01 | 160 | 133 | 154 | — |

"—" when the obtained values were not coherent.

A schematic representation of these results is shown in FIG. 1 for formulation 1023. As can be seen, the great majority of the particles (e.g. at least 80%) have a diameter of less than 300 nm by intensity.

II.2.5. Overall Conclusion

SB62 formulation was measured at different dilutions with the Malvern Zetasizer 3000HS and two optical models. The particle size ZAD (i.e. intensity mean by cumulant analysis) of the formulations assessed above was around 150-155 nm.

When using the cumulants algorithm, we observed no influence of the dilution on the ZAD and polydispersity.

Example III—Pre-Clinical Evaluation of an Adjuvanted Pandemic Split Influenza Vaccines (Comprising H5N1 Strain) in Ferrets III.1. Rationale and Objectives Influenza infection in the ferret model closely mimics human influenza, with regards both to the sensitivity to infection and the clinical response. The ferret is extremely sensitive to infection with both influenza A and B viruses without prior adaptation of viral strains. Therefore, it provides an excellent model system for studies of protection conferred by administered influenza vaccines.

This study investigated the efficacy of H5N1 Split vaccines adjuvanted with AS03 to protect ferrets against a lethal challenge with the H5N1 homologous strain A/Vietnam/1194/2004 or with a heterologous strain A/Indonesia. The objective of this experiment was to demonstrate the efficacy of an adjuvanted influenza vaccine compared to ferrets immunized with PBS or the adjuvant alone.

III.2. Experimental Design

III.2.1. Treatment/Group (Table 4)

36 Young outbred adult male ferrets (*Mustela putorius furo*) (6 ferrets/group) aged approximately 8 months (body weights 0.8-1.5 kg) were injected intramuscularly on days 0 and 21 with a full human dose (500 µl vaccine dose). Four groups of ferrets (n=6) were immunised with four different concentrations of A/Vietnam/1194/2004 (NIBRG-14) (15, 5.0, 1.7 and 0.6 µg HA) in combination with AS03 (standard human dose, 250 µl/dose). Two control groups consisted of placebo- and AS03-treated animals. Sera were collected on day 21 and 42 for analysis of serological responses. Antibody titres to homologous virus were determined by hemagglutination inhibition assay (HI titers). On day 49 all animals were challenged by the intranasal route with a dose of $10^5$ $TCID_{50}$ of homotypic strain A/Vietnam/1194/04. During the course of challenge, nasal, throat and rectal swabs were collected to assess virus shedding. After necropsy, cranioventral, craniodorsal, caudoventral and caudodorsal sections of the right lung from each animal were weighed and stored at −80° C. until analysis. Viral titers were determined by means of H5N1-specific TaqMan PCR and virus titration culture on MDCK cells. Data were expressed as Control Dilution Units (CDU) and $TCID_{50}$ per gram of lung tissue or per ml of swab respectively. CDU are determined from a standard curve produced from a stock of virus which is serially diluted, with each dilution undergoing nucleic acid extraction and Taqman PCR amplification in the same manner as test samples.

TABLE 4

| Group | Antigen +/− adjuvant | Dosage | Route/ schedule | Other treatment |
|---|---|---|---|---|
| 1 | PBS |  | IM Days 0 and 21 | Challenge H5N1 (A/Vietnam/1194/04) Day 49 |
| 2 | H5N1 AS03 | 15 µg HA | IM Days 0 and 21 | Challenge H5N1 (A/Vietnam/1194/04) Day 49 |
| 3 | H5N1 AS03 | 5 µg HA | IM Days 0 and 21 | Challenge H5N1 (A/Vietnam/1194/04) Day 49 |
| 4 | H5N1 AS03 | 1.7 µg HA | IM Days 0 and 21 | Challenge H5N1 (A/Vietnam/1194/04) Day 49 |
| 5 | H5N1 AS03 | 0.6 µg HA | IM Days 0 and 21 | Challenge H5N1 (A/Vietnam/1194/04) Day 49 |
| 6 | AS03 alone |  | IM Days 0 and 21 | Challenge H5N1 (A/Vietnam/1194/04) Day 49 |

III.2.2. Preparation of the Vaccine Formulations

III.2.2.2. Split H5N1 Adjuvanted with the Oil-in-Water Emulsion Adjuvant ASO3A in a 500 µl Dose Version 1 (Used for the Study Reported in this Example)

Preparation of one liter of Final Bulk Buffer (PBS pH 7.2±0.2): to 0.800 l of water for injection, add NaCl 7.699 g, KCl 0.200 g, $MgCl_2 \times 6H_2O$ 0.100 g, $Na_2HPO_4 \times 12\ H_2O$ 2.600 g, $KH_2PO_4$ 0.373 g. After solubilization, adjust to 1.0 L with water for injection.

Thiomersal, Tween 80 (quantities taking into account their concentrations in the strain) and Triton X100 are added to the Final Bulk Buffer. This mixture is called the premixed buffer. The final concentration of Thiomersal is 10 µg/ml. HA to detergent ratios are 0.13 for Tween 80 and 0.86 for Triton X100 respectively. The day of the immunizations 15-5-1.7 or 0.6 µg of HA (H5N1 strain) are added to the premixed buffer. After 30 minutes stirring, 250 µl of SB62 emulsion is added. The formulation is stirred for 30 minutes. Injections occur within the hour following the end of the formulation.

Version 2

Alternatively, the formulation is prepared as follows. Tween 80, Triton X100 and Thiomersal are added to the Final Bulk Buffer in quantities taking into account their concentrations in the strain. After 5 min stirring, 15-5-1.7 or 0.6 µg of H5N1 strain are added. After 30 minutes stirring, 250 µl of SB62 emulsion is added. The formulation is stirred for 30 minutes. Injections occur within the hour following the end of the formulation.

III.2.2.3. ASO3A in a 500 µl Dose (Group 6)

Version 1 (Used for the Study Reported in this Example)

250 µl SB62 emulsion is mixed with 250 µl PBS pH6.8, stirred for 5 minutes and stored at 4° C. until its administration.

Version 2

Alternatively the formulation can be prepared as follows. 250 µl SB62 emulsion is mixed with 250 µl PBS pH6.8 and stirred for 5 minutes. Injections occur within the hour following the end of the formulation.

Remark: In each formulation, Final Bulk Buffer is used to reach isotonicity.

III.2.3. Read-Outs (Table 5)

TABLE 5

| Readout | Timepoint | Analysis method |
|---|---|---|
| Protection | D + 5 Post challenge | % protection (number of ferrets alive/total number ferrets per group) |
| HI titers | Day 42 | Hemagglutination inhibition assay |
| Neutralizing antibody titers | Day 42 | Neutralization assay |
| Viral shedding | Day 49 to Day 54 | Virus titration culture on MDCK or by Taq-Man PCR for throat swabs and lung tissue |
| Telemetry | Day 49 to Day 54 | Body temperature |

III.3. Results and Conclusions

Table 6 summarizes the protection data, HI titers and viral load in lung tissue and pharyngeal swabs obtained in ferrets after challenge with a homologous H5N1 strain.

TABLE 6

Protection of AS03-adjuvanted H5N1-vaccinated ferrets against challenge with homologous H5N1 influenza viruses.

| Vaccination regimen | No. dead/ total no. (% protection)[a] | HI titers[b] | Viral load (No./Total no.)[c] | |
|---|---|---|---|---|
| | | | Lung tissue (%) | Pharyngeal swabs (%) |
| PBS | 4/5 (20) | – | 5/5 (100) | 5/5 (100) |
| AS03 alone | 6/6 (0) | – | 6/6 (100) | 6/6 (100) |
| AS03-adjuvanted H5N1 (0.6 µg) | 2/6 (67) | + | 4/6 (67) | 2/6 (33) |
| AS03-adjuvanted H5N1 (1.7 µg) | 1/5 (80) | + | 1/5 (20) | 1/5 (20) |
| AS03-adjuvanted H5N1 (5 µg) | 0/6 (100) | +++ | 2/6 (33) | 2/6 (33) |
| AS03-adjuvanted H5N1 (15 µg) | 0/6 (100) | +++ | 1/6 (17) | 1/6 (17) |

[a]One animal immunized with PBS and one immunized with 1.7 µg HA of the adjuvanted vaccine were euthanized during the course of vaccination (day 25). There was no apparent link between vaccination and these mortalities.
[b]Geometric mean HI titers (D 42): +++ (>160), ++ (60-160) + (40-60), – (<40).
[c]Numbers of animals with viral load determined by viral culture >$10^2$ TCID$_{50}$ per g tissue or per ml swab.

III.3.1. Protection Data

Before the challenge with H5N1, two animals were euthanized. One animal immunized with PBS was euthanized because of excessive weight loss during the course of vaccination (day 14). One animal immunized with 1.7 µg HA of the adjuvanted vaccine was euthanized because of excessive weight loss during the course of vaccination (day 25). There was no apparent link between vaccination and these mortalities.

Challenge with A/Vietnam/1194/04 in ferrets vaccinated with AS03-adjuvanted H5N1 vaccines showed an antigen dose-dependent protection or survival curve (Table 6). All animals immunized with 5 or 15 µg HA of the AS03-adjuvanted vaccine were protected against the lethal challenge. Importantly, mean HI titers against homologous A/Vietnam/1194/2004 virus were ≥40 in all groups of ferrets immunized with AS03-adjuvanted vaccines, including in the groups having received the lowest doses, with 66.67 and 80.00% protection obtained against the homologous challenge in ferrets immunized with 0.6 and 1.7 µg H5N1 split vaccine adjuvanted with AS03, respectively. All ferrets immunized with PBS or the adjuvant alone exhibited a viral load above $10^5$ TCID$_{50}$/g of lung tissue and all animals shed high levels of virus in the upper respiratory tract (throat and nasal swabs) throughout the course of infection. Conversely, in 65% and 75% of animals, the administration of AS03-adjuvanted vaccines reduced the virus load below a threshold of $10^2$ TCID$_{50}$ per gram of lung tissue or per ml fluid from pharyngeal swabs, respectively (Table 6) demonstrating a reduced risk of viral transmission in ferrets receiving the AS03-adjuvanted vaccines. Only one or two ferrets per group immunized with AS03-adjuvanted vaccines had moderate to high viral loads (>$10^2$ TCID$_{50}$). Importantly, it should be noted that most animals from placebo (PBS) and adjuvant only groups died or were euthanized on days 2 and 3, while most animals in the vaccinated groups survived through to euthanasia on day 5. Consequently viral loads were not measured on the same day post challenge for all animals.

A statistical analysis performed on these data before the challenge led to the following conclusions:
all vaccine doses were statistically different from controls
P values (Fischer's exact test) were ranging from 0.0276 for lowest dose to 0.0006 for highest dose
the estimated dose to induce 90% protection was estimated in this model to be 2.9 µg
the lowest dose to induce 100% protection was estimated in this model to be between 2.9 and 5 µg.

III.3.2. Humoral Responses (HI Titers)

The humoral immune response to vaccination was measured after each immunization on days 21 and 42. Serum samples were tested by the hemagglutination inhibition (HI) test using horse erythrocytes. Results are presented in Table 6.

AS03 adjuvanted monovalent H5N1 split formulations induced the strongest HI responses to the homologous strain compared to ferrets immunized with PBS or AS03 alone. An antigen dose effect was observed with the highest HI titers obtained in ferrets immunized with the dose highest antigen doses (15 or 5 µg HA of the adjuvanted vaccine) compared to lower immune response in ferrets receiving the two lowest doses (1.7 or 0.8 µg HA of the adjuvanted vaccine).

As shown in Table 6 and FIG. 2A, a correlation was found between the HI titers and the protection in ferrets challenge with A/Vietnam H5N1. HI titers higher than 40 seemed to correlate with protection in ferrets immunized with H5N1 split vaccines adjuvanted with AS03.

III.3.3. Humoral Responses (Neutralizing Antibody Titers)

The humoral immune response to vaccination was also tested by neutralization assay after each immunization on days 21 and 42. Results are presented in FIG. 3.

AS03 adjuvanted monovalent H5N1 split formulations induced the strongest neutralizing antibody responses to the homolologous strain compared to ferrets immunized with PBS or AS03 alone. No antigen dose effect was observed, with the highest neutralizing antibody responses obtained in ferrets immunized with 1.7 µg of the AS03-adjuvanted H5N1 vaccine.

III.3.4. Viral Shedding after A/Vietnam H5N1 Homologous Challenge

Viral shedding was performed by viral culture and Taq-Man PCR on lung tissue and nasal/throat/rectal swabs.

As shown in Table 6, protection was also observed in terms of reduction of viral load in lung tissues and pharyngeal swabs in ferrets immunized with AS03-adjuvanted H5N1 split vaccines (most animal below $10^2$ TCID$_{50}$ per gram of tissue or per ml of swab). All ferrets immunized with PBS or the adjuvant alone exhibited high viral load in lung tissues and in the pharynx throughout the course of infection.

FIG. 2B shows mean viral load determined both by PCR and viral culture in each group. This demonstrated that all groups receiving adjuvanted vaccine tended to exhibit reduced viral loads relative to the control groups receiving PBS or the adjuvant alone, with ferrets immunized with 0.7 μg HA of the adjuvanted vaccine showing a more modest reduction in viral load. Little difference could be seen between ferrets immunized with 1.6, 5 or 15 μg HA of the adjuvanted vaccine. Finally, for the viral load in lungs, PCR results were consistent with the virus titration.

Moreover, viral shedding in nasal and rectal swabs, as well as in plasma was investigated by viral culture and PCR. Generally, virus titration was less sensitive than PCR analysis. This analysis showed the presence of H5N1 virus into the nasal cavity and rectal swabs of 2/5 ferrets receiving PBS. In this group, 1/5 animal also shed virus in the serum. No animals immunized with AS03-adjuvanted H5N1 split vaccine shed virus in rectal swabs or plasma. Interestingly, the analyze of each individual ferrets showed that some protected ferrets had high viral load and low HI titers, demonstrating that the mechanism by which the protection was achieved may but due, at least in part, to the induction of cellular immunity (not evaluated in this experiment).

III.3.5. Body Temperature

Body temperatures of all animals were registered. No changes in body temperatures were observed during the vaccination phase. Challenge with A/Vietnam/1194/04 induced onset of fever with body temperatures ranging from 40° C. to 42° C. with peaks between 12 to 24 hours after start of challenge. During the course of infection body temperatures decreased to normal levels in animals which survived the challenge. Animals which died before Day 5 showed a rapid decrease in body temperature after the peak of fever.

In summary, serological testing indicated that significantly higher HI titres were obtained in animals immunized with adjuvanted vaccines compared to animals immunized with PBS or the adjuvant alone. Challenge with the homologous A/Vietnam/1194/04 virus showed an antigen-dose dependent survival curve with reduced viral load in lung tissue and pharyngeal swabs from the groups receiving adjuvanted vaccines compared to control groups. All animals in control groups (immunized with PBS or the adjuvant alone) shed virus into the upper respiratory tract with a viral load above $10^5$ $TCID_{50}$/g of lung, while in groups receiving adjuvanted vaccines, only a proportion of animals shed virus into the upper respiratory tract (4/17 with $10^5$ to $10^7$ $TCID_{50}$/g lung tissue. majority below $10^2$ $TCID_{50}$ per gram of lung or per ml of pharyngeal swabs). Furthermore, there were reduced viral titres in lung tissue from the groups receiving adjuvanted vaccines, as compared to placebo and adjuvant only treated groups. This reduction was partially antigen dose dependent, reaching an apparent plateau at 5 μg antigen.

Example IV—Clinical Trial in an Adult Population Aged in Adults Aged Between 18 and 60 Years with a Vaccine Containing a Split Influenza Antigen Preparation and AS03 Adjuvant IV.1. Introduction A phase I, observer-blind, randomized study has been conducted in an adult population aged 18 to 60 years in 2006 in order to evaluate the reactogenicity and the immunogenicity of a pandemic influenza candidate administered at different antigen doses (3.8 μg, 7.5 μg, 15 μg and 30 μg HA) adjuvanted or not with the adjuvant AS03. The humoral immune response (i.e. anti-hemagglutinin, neutralising and anti-neuraminidase antibody titres) and cell mediated immune response (CD4 and/or CD8 T cell responses) are measured 21 days after each of the two intramuscular administration of the candidate vaccine formulations. The non-adjuvanted groups served as reference for the respective adjuvanted group receiving the same antigen content.

IV.2. Study Design

The plan was for eight groups of 50 subjects each to receive in parallel the following vaccine intramuscularly. In the trial however the groups were split as follows:

- one group of 50 subjects received two administrations of the pandemic split virus influenza vaccine containing 3.8 μg HA
- one group of 51 subjects received two administrations of the pandemic split virus influenza vaccine containing 3.8 μg HA and adjuvanted with AS03
- one group of 50 subjects received two administrations of the pandemic split virus influenza vaccine containing 7.5 μg HA
- one group of 50 subjects received two administrations of the pandemic split virus influenza vaccine containing 7.5 μg HA and adjuvanted with AS03
- one group of 50 subjects received two administrations of the pandemic split virus influenza vaccine containing 15 μg HA
- one group of 50 subjects received two administrations of the pandemic split virus influenza vaccine containing 15 μg HA and adjuvanted with AS03
- one group of 50 subjects received two administrations of the pandemic split virus influenza vaccine containing 30 μg HA
- one group of 49 subjects received two administrations of the pandemic split virus influenza vaccine containing 30 μg HA and adjuvanted with AS03

The enrolment was performed to ensure that half of subjects from each group will be aged between 18 and 30 years.

Vaccination schedule: two injection of pandemic influenza candidate vaccine at day 0 and day 21, blood sample collection, read-out analysis at day 21 and 42 (HI antibody determination, NI antibody determination, determination of neutralising antibodies, and CMI analysis), study conclusion (day 51) and study end (180 days).

IV.3. Study Objectives

IV.3.1. Primary Objectives

- To evaluate the humoral immune response induced by the study vaccines in term of anti-haemagglutinin antibody titers.
- To evaluate the safety and reactogenicity of the study vaccines in term of solicited local and general adverse events, unsolicited adverse events and serious adverse events.

For the Humoral Immune Response:

Observed variables at days 0, 21, 42 and 180: serum Heamagglutination-inhibition antibody titers.

Derived variables (with 95% confidence intervals):

- Geometric mean titers (GMTs) of serum antibodies at days 0, 21, 42 and 180
- Seroconversion rates* at days 21, 42 and 180
- Conversion factors** at days 21, 42 and 180
- Seroprotection rates*** at days 0, 21, 42 and 180

*Seroconversion rate for Haemagglutinin antibody response is defined as the percentage of vaccinees who have either a prevaccination titer <1:10 and a post-vaccination titer ≥1:40 or a prevaccination titer ≥1:10 and at least a fourfold increase in post-vaccination titer

**Conversion factor defined as the fold increase in serum HI GMTs post-vaccination compared to day 0;

***Seroprotection rate defined as the percentage of vaccinees with a serum HI titer ≥40 after vaccination that usually is accepted as indicating protection.

For the Safety/Reactogenicity Evaluation:
1. Percentage, intensity and relationship to vaccination of solicited local and general signs and symptoms during a 7 day follow-up period (i.e. day of vaccination and 6 subsequent days) after each vaccination and overall.
2. Percentage, intensity and relationship to vaccination of unsolicited local and general signs and symptoms during a 21 days follow-up period after the first vaccination, during 30 days follow-up period after the second vaccination and overall.

Occurrence of serious adverse events during the entire study.

IV.3.2. Secondary Objectives

To evaluate the humoral immune response induced by the study vaccines in term of serum neutralizing antibody titers To evaluate the cell-mediated immune response induced by the study vaccines in term of frequency of influenza-specific CD4/CD8 T lymphocytes In addition, the impact of vaccination on Influenza-specific memory B cells using the Elispot technology will be evaluated.

For the Humoral Immune Response:

Observed variables at days 0, 21, 42 and 180: serum neutralizing antibody titers.

Derived variables (with 95% confidence intervals):

Geometric mean titers (GMTs) of serum antibodies at days 0, 21, 42 and 180

Seroconversion rates* at day s21, 42 and 180

*Seroconversion rate for Neutralising antibody response is defined as the percentage of vaccinees with a minimum 4-fold increase in titer at post-vaccination.

For the CMI Response:
1. Frequency of cytokine CD4/CD8 cells per $10^6$ in tests producing at least two different cytokines (CD40L, IL-2, TNF-α, IFN-γ)
2. Frequency of cytokine-positive CD4/CD8 cells per $10^6$ in tests producing at least CD40L and another signal molecule (IL-2, IFN-γ, TNF-α)
3. Frequency of cytokine-positive CD4/CD8 cells per $10^6$ in tests producing at least IL-2 and another signal molecule (CD40L, IFN-γ, TNF-α)
4. Frequency of cytokine-positive CD4/CD8 cells per $10^6$ in tests producing at least TNF-α and another signal molecule (IL-2, IFN-γ, CD40L)

Frequency of cytokine-positive CD4/CD8 cells per $10^6$ in tests producing at least IFN-γ and another signal molecule (CD40L, IL-2, TNF-α).

At days 0, 21, 42 and 180: frequency of influenza-specific memory B cells per $10^6$ cells in test.

IV.4. Vaccine Composition and Administration (Table 7)
IV.4.1. Vaccine Preparation
IV.4.1.1. Composition of AS03 Adjuvanted Influenza Vaccine AS03 contains the oil-in-water SB62 emulsion, consisting of an oil phase containing DL-α-tocopherol and squalene, and an aqueous phase containing the non-ionic detergent polysorbate 80.

The active substance of the pandemic influenza vaccine candidate is a formaldehyde inactivated split virus antigen derived from the vaccine virus strain A/VietNam/1194/2004 (H5N1) NIBRG-14. The dose of HA antigen is ranging from 3.8 to 30 µg per dose. The split virus monovalent bulks used to produce the AS03 adjuvanted influenza vaccine are manufactured following the same procedure as used for GSK Biologicals licensed interpandemic influenza vaccine Fluarix™/α-Rix®. For the purpose of this clinical trial the virus strain used to manufacture the clinical lots is the H5N1 vaccine strain A/Vietnam/1194/04-clade 1 NIBRG-14 recombinant H5N1 prototype vaccine strain derived from the highly pathogenic A/Vietnam/1194/04. This recombinant prototype strain has been developed by NIBSC using reverse genetics (a suitable reference is Nicolson et al. 2005, Vaccine, 23, 2943-2952)). The reassortant strain combines the H5 and N1 segments to the A/PR/8/34 strain backbone, and the H5 was engineered to eliminate the polybasic stretch of amino-acids at the HA cleavage site that is responsible for high virulence of the original strains. This was achieved by transfecting Vero cells with plasmids containing the HA gene (modified to remove the high pathogenicity determinants) and NA gene of the human isolate A/VietNam/1194/2004 (H5N1) and plasmids containing the internal genes of PR8. The rescued virus was passaged twice on eggs and was then designated as the reference virus NIBRG-14. The attenuated character of this H5N1 reassortant was extensively documented in a preclinical safety assessment (performed by NIBSC), as is also done routinely for the classical flu vaccine strains.

The AS03-adjuvanted pandemic influenza candidate vaccine according to the invention is a 2 component vaccine consisting of 0.5 ml of concentrated inactivated split virion antigens presented in a type I glass vial and of a pre-filled type I glass syringe containing 0.5 ml of the AS03 adjuvant. At the time of injection, the content of the prefilled syringe containing the adjuvant is injected into the vial that contains the concentrated inactivated split virion antigens. After mixing the content is withdrawn into the syringe and the needle is replaced by an intramuscular needle. One dose of the reconstituted the AS03-adjuvanted influenza candidate vaccine corresponds to 1 ml. Each vaccine dose of 1 ml contains 3.8 µg, 7.5 µg, 15µ or 30 µg haemagglutinin (HA) or any suitable HA amount which would have be determined such that the vaccine meets the efficacy criteria as detailed herein.

Alternatively, the AS03-adjuvanted pandemic influenza candidate vaccine according to the invention is a 2 component vaccine consisting of 0.25 ml of concentrated inactivated split virion antigens presented in a type I glass vial and of a pre-filled type I glass syringe containing 0.25 ml of the AS03 adjuvant. At the time of injection, the content of the prefilled syringe containing the adjuvant is injected into the vial that contains the concentrated inactivated split virion antigens. After mixing the content is withdrawn into the syringe and the needle is replaced by an intramuscular needle. One dose of the reconstituted the AS03-adjuvanted influenza candidate vaccine corresponds to 1 ml. Each vaccine dose of 1 ml contains 3.8 µg, 7.5 µg, 15 µl or 30 µg haemagglutinin (HA) or any suitable HA amount which would have be determined such that the vaccine meets the efficacy criteria as detailed herein.

The vaccine excipients are polysorbate 80 (Tween 80), octoxynol 10 (Triton X-100), sodium chloride, disodium hydrogen phosphate, potassium dihydrogen phosphate, potassium chloride, magnesium chloride hexahydrate and water for injection. Thiomersal has been added as an antimicrobial preservative to prevent contamination during use, since it is anticipated that when a pandemic occurs the main presentation will be presented in a multidose container (vials or ampoules), for which a preservative is required. For this reason, the pandemic vaccine is formulated with thiomersal at 5 μg/dose as preservative. Suitably the pandemic vaccine may be formulated with thiomersal at 10 μg/dose as preservative or a slightly higher dose, such as up to 25 μg/dose of vaccine.

IV.4.1.2. Production of Split Inactivated Influenza H5N1 Antigen Preparation

The virus monobulks are prepared by growing H5N1 working seed in embryonated hen's eggs. The manufacturing process for the monovalent bulks of split, inactivated influenza H5N1 strain, illustrated in FIG. 4, is identical to the manufacturing process for the monovalent bulks of α-Rix™

Basically, the manufacturing process of the monovalent bulks can be divided in four main parts:

1) Propagation of the working seed in fertilized hen's eggs, harvesting and pooling of infected allantoic fluids so as to obtain the "crude monovalent whole virus bulk" (step 1).

2) Purification of each virus strain leading to the "purified monovalent whole virus bulk" (steps 2-6).

3) Splitting of the purified monovalent whole virus bulk with sodium deoxycholate resulting in the "purified monovalent split virus bulk" (steps 7-8/1).

4) Inactivation of the purified monovalent split virus bulk in two steps by incubation with sodium deoxycholate and with formaldehyde, followed by ultrafiltration and sterile filtration, in order to obtain the "purified monovalent inactivated split virus bulk", or "Monovalent Bulk" (steps 8/2-9).

1) Production of Crude Monovalent Whole Virus Bulk

Preparation of the Virus Inoculum:

On the day of inoculation of the embryonated eggs, an inoculum is prepared by mixing the working virus seed lot with phosphate buffer containing 25 µg/mL hydrocortisone, and 0.5 mg/mL gentamicin sulfate. The virus inoculum is kept at room temperature until the inoculation.

Inoculation of Embryonated Eggs:

Eleven day-old pre-incubated embryonated eggs are used for virus replication. The eggs are transferred into the production rooms after formaldehyde fumigation of the shells. Approximately 120,000 eggs are inoculated with 0.2 mL of the virus inoculum each using an automatic egg inoculation apparatus. The inoculated eggs are incubated at 34.0° C. for 72 hours.

At the end of the incubation period, the eggs are inspected visually for the presence of living embryo and age-adequate blood vessels. The embryos are killed by cooling the eggs and stored for 12-46 hours at 2-8° C. Alternatively the killed embryos may be stored for 13.5 hours at 2-10° C.

Harvest

The allantoic fluid (approximately 12 mL) from the chilled embryonated eggs is harvested by egg harvesting machines. The allantoic fluids are collected in a stainless steel tank thermo-regulated at 2-8° C. At this stage the product is called the "crude monovalent whole virus bulk". The crude monovalent whole virus bulk is not stored but immediately transferred to the clarification step.

2) Production of Purified Monovalent Whole Virus Bulk

All operations are performed at 2-8° C., until the flow through ultracentrifugation, which is performed at room temperature.

Clarification:

The harvested allantoic fluid is clarified by continuous moderate speed centrifugation. This step removes big particles that could have been collected during the harvest of the allantoic fluid (e.g. parts of egg shells).

Adsorption Step:

This step permits to clarify further the allantoic fluid through a precipitation of virus material, by adsorption to a dibasic calcium hydrogen phosphate gel.

To obtain the dibasic calcium hydrogen phosphate ($CaHPO_4$) gel, 0.5 mol/L disodium hydrogen phosphate ($Na_2HPO_4$) and 0.5 mol/L calcium chloride ($CaCl_2$) are added to the clarified virus pool to reach a final concentration of 1.87 g $CaHPO_4$ per L.

After sedimentation for at least 8 hours to maximum 36 hours, the supernatant is removed and the sediment containing the influenza viruses is re-solubilized by the addition of an 8.7% disodium EDTA solution.

Filtration:

The resuspended influenza sediment is filtered through a 6-µm filter membrane to remove potential remaining pellets.

Flow Through Ultracentrifugation:

The influenza virus is further purified (removal of proteins and phospholipids) and concentrated by isopycnic ultracentrifugation in a linear sucrose gradient (0-55%) at a flow rate of 8-20 liters per hour. The gradient is formed using the sucrose solution 55% (w/w) with 0.01% thimerosal, and a Phosphate buffer pH 7.4 with 0.01% thimerosal. This is done in the presence of 100±15 µg/mL thiomersal in order to control the process bioburden, as the centrifugation is performed at room temperature.

Four different fractions are recovered by measuring the sucrose concentration via a refractometer:

Fraction 4/1: 55-47% sucrose

Fraction 4/2: 47-38% sucrose

Fraction 4/3: 38-20% sucrose

Fraction 4/4: 20-0% sucrose

The upper limit of fraction 4/2 is selected to balance between a high purity coefficient HA/protein and a maximum recovery of whole virus. The limit between fractions 4/2 and 4/3 is selected to minimize the ovalbumin content in fraction 4/2. The lower limit of fraction 4/3 is selected on the basis of the HA content found in the low sucrose gradient range.

Fractions 4/2 and 4/3 are used for further preparations. Most of the virus is collected in Fraction 4/2. Fraction 4/3, which contains both virus and proteins, is further purified. First, the sucrose concentration of Fraction 4/3 is reduced below 6% (necessary for the subsequent centrifugation step) by ultrafiltration. Then, Fraction 4/3 is pelleted via centrifugation to remove any soluble contaminants (proteins). The pellet is re-suspended in phosphate buffer pH 7.4 and thoroughly mixed to obtain a homogeneous suspension. The holding times are maximum 36 hours for Fraction 4/3, maximum 60 hours for Fraction 4/2 and maximum 36 hours for the purified Fraction 4/3.

Dilution

Both fractions, the treated Fraction 4/3 and untreated Fraction 4/2, are pooled and diluted by adding 60 L of phosphate buffer pH 7.4.

At this stage, the pool of material corresponds to the "purified monovalent whole virus bulk".

3) Preparation of the Purified Monovalent Split Virus Bulk

Flow Through Ultracentrifugation in the Presence of Sodium Deoxycholate:

The influenza virus is splitted and further purified by centrifugation through a linear sucrose gradient (0-55%—formed with sucrose solution S8a and buffer S6a) that contains 1.5% sodium deoxycholate. Tween-80 is present at 0.1% in the gradient. The virus is processed at a rate of 8 liters per hour. At the end of the centrifugation, three different fractions are collected. The range of the main fraction (Fraction 7/2) is selected based on strain-dependent validation of splitting conditions, with as objective to collect a fraction consisting of predominantly disrupted influenza virus antigen, while minimizing as much as possible remaining whole virus particles and phospholipids coming from the virus membrane after splitting.

For A/Vietnam/1194/2004 NIBRG-145 the range of fraction 7/2 is set at 20-41% sucrose. The haemagglutinin antigen is concentrated in Fraction 7/2, which contains approximately 1.2% sodium deoxycholate. This material corresponds to the "purified monovalent split virus bulk".

4) Preparation of the Purified Final Monovalent Split, Inactivated Virus Bulk

Filtration:

Fraction 7/2 is diluted threefold in phosphate buffer S7c, which contains 0.025% Tween-80. Then, fraction 7/2 is gradually filtered down to a 0.45 μm filter membrane, briefly sonicated (to facilitate filtration) and filtered through a 0.2 μm membrane. At the end of the filtration, the filters are rinsed with phosphate buffer (5107c) containing 0.025% Tween-80. As a result of the filtration and rinsing, the final volume of the filtrate is 5 times the original fraction 7/2 volume.

Sodium Deoxycholate Inactivation:

The resulting solution is incubated at 22±2° C. for at least 84 hours.

After completion of the first inactivation step, the material is diluted with phosphate buffer S7c to reduce the total protein content to a calculated concentration of 500 μg/mL:

Formaldehyde Inactivation:

Formaldehyde is added to a calculated final concentration of 100 μg/mL. Inactivation takes place in a single use low density polyethylene 100 L bag at 20±2° C. for at least 72 hours.

Ultrafiltration:

The inactivated split virus material is ultrafiltered through membranes with a molecular weight cut off of 30,000 Dalton, using consecutively buffers S7b and S1b After a volume reduction, the volume remains constant during ultrafiltration (diafiltration) by adding phosphate buffer and phosphate buffered saline (S1b) containing 0.01% Tween-80.

During ultrafiltration, the content of formaldehyde, NaDoc and sucrose is reduced.

The material is concentrated to 15-25 liters and is transferred immediately to the final filtration step.

Sterile Filtration:

After ultrafiltration, the split inactivated material is gradually filtered down to a 0.2 μm membrane.

The final sterile filtration through a 0.22 μm sterile grade membrane is performed in a Class 100 environment. At the end of the filtration the filters are rinsed with phosphate buffered saline solution S1 b, containing 0.01% Tween-80. Herewith, the filtrate is diluted to a protein concentration less than 1000 μg/mL, to avoid aggregation during subsequent storage.

The resulting material is the "purified monovalent inactivated split virus bulk" or "monovalent bulk".

Storage:

The final monovalent bulks of split inactivated influenza H5N1 viruses are stored at 2-8° C. for a maximum of 18 months in Type I glass bottles.

IV.4.1.3. Preparation of the Vaccine Compositions with AS03 Adjuvanted H5N1

1) Composition

The AS03 adjuvanted inactivated split virus pandemic influenza candidate vaccine to be evaluated in the phase I clinical trial H5N1-007 is intended for intramuscular administration. The vaccine is a 2 component vaccine consisting of 2× concentrated inactivated split virion (H5N1) antigens presented in a type I glass vial, and of the AS03 adjuvant contained in a pre-filled type I glass syringe.

One dose of reconstituted AS03-adjuvanted pandemic influenza vaccine corresponds to 1 ml. The composition is given in Table 7. Since study H5N1-007 is a dose finding study, the HA content per dose is different for each of the clinical lots to be tested. One dose contains 3.8, 7.5, 15 or 30 μg HA. The vaccine contains the following residuals from the manufacturing process of the drug substance: formaldehyde, ovalbumin, sucrose, thiomersal and sodium deoxycholate.

TABLE 7

Composition of the reconstituted AS03 adjuvanted pandemic influenza candidate vaccine

| Component | Quantity per dose |
|---|---|
| Active Ingredients | |
| Inactivated split virions A/VietNam/1194/2004 NIBRG-14 (H5N1) | 30/15/7.5/3.8 μg HA |
| AS03 Adjuvant | |
| SB62 emulsion | |
| squalene | 10.68 mg |
| DL-α-tocopherol | 11.86 mg |
| Polysorbate 80 (Tween 80) | 4.85 mg |
| Excipients | |
| Polysorbate 80 (Tween 80)[1] | 12.26 μg/μg HA |
| Octoxynol 10 (Triton X-100)[2] | 1.16 μg/μg HA |
| Thiomersal | 5 μg |
| Sodium chloride | 7.5 mg |
| Disodium hydrogen phosphate | 1 mg |
| Potassium dihydrogen phosphate | 0.36 mg |
| Potassium chloride | 0.19 mg |
| Magnesium chloride | 23.27 μg |

2) Formulation

The manufacturing of the AS03-adjuvanted pandemic influenza vaccine consists of three main steps:

(a) Formulation of the split virus final bulk (2× concentrated) without adjuvant and filling in the antigen container (b) Preparation of the AS03 adjuvant and filling in the adjuvant container (c) Extemporaneous reconstitution of the AS03 adjuvanted split virus vaccine 1) Formulation of the Final Bulk without Adjuvant and Filling in the Antigen Container.

The formulation flow diagram is presented in FIG. 5.

The volume of the monovalent bulk is based on the HA content measured in the monovalent bulk prior to the formulation and on a target volume of 4000 ml.

The final bulk buffer (Formulation buffer comprising: Sodium chloride: 7.699 g/l; Disodium phosphate dodecahydrate: 2.600 g/l; Potassium dihydrogen phosphate: 0.373 g/l; potassium chloride: 0.2 g/l; Magnesium chloride hexahydrate: 0.1 g/l) and the correct volumes of Triton X-100 (5 Octoxynol 10 (Triton X-100) solution) and thiomersal (0.9% Thiomersal stock solution) taking into account any residual thiomersal from the antigen preparation, are mixed together under continuous stirring. The monobulk H5N1 is then diluted in the resulting bulk buffer-Triton X-100-thiomersal in order to have a final concentration of 60/30/15/7.6 µg H5N1 per ml of final bulk per ml (30, 15, 7.5 or 3.8 µg HA/500 µl final bulk). The mixture is stirred during 30-60 minutes. The pH is checked to be at 7.2±0.3. There was no need to add Tween 80 because the concentration of Tween 80 (822 µg/ml) present in the monobulk was sufficient to reach the concentration target (12.26 µg/µg HA).

The final bulk is aseptically filled into 3-ml sterile Type I (Ph. Eur.) glass vials. Each vial contains a volume of 0.65 ml±0.05 ml.

2) Preparation of the AS03 Sterile Adjuvant Bulk and Filling in the Adjuvant Container.

The adjuvant AS03 is prepared by mixing of two components: SB62 emulsion and phosphate buffer.

SB62 Emulsion

The preparation of the SB62 emulsion is realised by mixing under strong agitation of an oil phase composed of hydrophobic components (α-tocopherol and squalene) and an aqueous phase containing the water soluble components (Tween 80 and phosphate-saline buffer at pH 6.8). While stirring, the oil phase (1/10 total volume) is transferred to the aqueous phase (9/10 total volume), and the mixture is stirred for 15 minutes at room temperature. The resulting mixture then subjected to shear, impact and cavitation forces in the interaction chamber of a microfluidizer (15000 PSI—8 cycles) to produce submicron droplets (distribution between 100 and 200 nm). The resulting pH is between 6.8±0.1. The SB62 emulsion is then sterilised by filtration through a 0.22 µm membrane and the sterile bulk emulsion is stored refrigerated in Cupac containers at 2 to 8° C. Sterile inert gas (nitrogen) is flushed into the dead volume of the SB62 emulsion final bulk container for at least 15 seconds.

The final composition of the SB62 emulsion is as follows (Table 8):

TABLE 8

| Tween 80: | 1.8% (v/v) | 19.4 mg/ml |
|---|---|---|
| Squalene: | 5% (v/v) | 42.8 mg/ml |
| α-tocopherol: | 5% (v/v) | 47.5 mg/ml |
| Phosphate-saline buffer | | |
| NaCl | | 121 mM |
| KCl | | 2.38 mM |
| Na$_2$HPO$_4$ | | 7.14 mM |
| KH$_2$PO$_4$ | | 1.3 mM |
| pH | | 6.8 ± 0.1 |

AS03 Adjuvant System

The AS03 adjuvant system is prepared by mixing buffer (PBS mod) with SB62 bulk. The mixture is stirred for 15-45 minutes at room temperature, and the pH is adjusted to 6.8±0.1 with NAOH (0.05 or 0.5 M)/HCl (0.03 M or 0.3 M). After another stirring for 15-20 minutes at room temperature, the pH is measured and the mixture is sterilised by filtration through a 0.22 µm membrane. The sterile AS03 adjuvant is stored at +2-8° C. until aseptical filling into 1.25-ml sterile Type I (Ph. Eur.) glass syringes. Each syringe contains a volume overage of 720 µl (500 µl+220 µl overfill) The final composition of the AS03 adjuvant is as follows (Table 9):

TABLE 9

| SB62 | 0.25 ml |
|---|---|
| Squalene | 10.68 mg |

TABLE 9-continued

| Tocopherol | 11.86 mg |
|---|---|
| Polysorbate 80 | 4.85 mg |
| PBS-mod: | |
| NaCl | 137 mM |
| KCl | 2.7 mM |
| Na$_2$HPO$_4$ | 8.1 mM |
| KH$_2$PO$_4$ | 1.47 mM |
| pH | 6.8 ± 0.1 |
| Volume | 0.5 ml |

3) Extemporaneous Reconstitution of the AS03 Adjuvanted Split Virus Vaccine.

At the time of injection, the content of the prefilled syringe containing the adjuvant is injected into the vial that contains the concentrated trivalent inactivated split virion antigens. After mixing the content is withdrawn into the syringe and the needle is replaced by an intramuscular needle. One dose of the reconstituted the AS03-adjuvanted influenza candidate vaccine corresponds to 1 ml IV.4.2 Vaccine Preparation The vaccines were administered intramuscularly in the deltoid region of the non-dominant arm. The pandemic influenza candidate vaccines are 2 components vaccines consisting of antigens presented in a vial (antigen container) and a pre-filled syringe containing either the adjuvant (adjuvant container) or the diluent. At the time of injection, the content of the pre-filled syringe is injected into the vial that contains the antigens. After mixing, the content is withdrawn into the syringe. The used needle is replaced by an intramuscular needle. One dose of the vaccine corresponds to 1 ml.

IV.5 Study Population Results

A total of 400 subjects were enrolled in this study: 49 to 51 subjects in each of the 8 groups. The mean age of the total vaccinated cohort at the time of vaccination was 34.3 years with a standard deviation of 12.76 years. The mean age and gender distribution of the subjects across the 8 vaccine groups was similar.

IV.6 Safety Conclusions

The administration of the pandemic influenza candidate vaccine adjuvanted with AS03 was safe and clinically well tolerated in the study population, i.e. adult people aged between 18 and 60 years.

IV.7 Immunogenicity Results

Analysis of immunogenicity was performed on the ATP (According To Protocol) cohort (394 subjects).

IV.7.1. Humoral Immune Response

In order to evaluate the humoral immune response induced by the pandemic influenza H5N1 candidate vaccine adjuvanted with AS03, the following parameters (with 95% confidence intervals) were calculated for each treatment group:

Geometric mean titres (GMTs) of HI antibody titres at days 0, 21 and 42.

Seroconversion rates (SC) at days 21 and 42;

Conversion factors at day 21 and 42;

Protection rates at day 21 and 42.

IV.7.1.1 Anti-Hemagglutinin Antibody Response a) HI Geometric Mean Titres (GMT)

The GMTs for HI antibodies with 95% CI are shown in Table 10 (GMT for anti-HI antibody) and in FIG. 6. Pre-vaccination GMTs of antibodies for the H5N1 vaccination strain were within the same range in the eight study groups. Following the first vaccination, in all non-adjuvanted groups anti-haemagglutinin antibody levels increased only very modestly in a dose dependent manner. In the adjuvanted vaccination groups, a more prominent increase in anti-haemagglutinin antibody levels was already observed after the first vaccination, with the highest GMT in the group receiving the highest antigen dose (HN30AD). Post second vaccination, GMTs in the non adjuvanted groups increased slightly over the post-first vaccination GMT. In comparison, significant higher GMTs were observed after the second vaccination in all adjuvanted groups, with a dose dependant increase observed from the 3.8 µg to the 7.5 µg to the 15 µg group. For the 30 µg group, a lower GMT than for the 7.5 µg group was observed. All adjuvanted study groups, including the lowest dose of 3.8 µg HA, elicited an immune response satisfying the criteria for licensure of pandemic vaccines based on FDA draft guidance (March 2006) as well as the criteria established by the EMEA.

Results are presented in Tables 11 (conversion factors), 12 (seroprotection rates) and 13 (seroconversion rates). A strong adjuvant effect was observed after each of the two vaccine doses.

The conversion factors (Table 11, FIG. 9) represent the fold increase in serum HI GMTs for the vaccine strain on day 21 and 42 compared to day 0. The conversion factor after the second vaccination varies from 1.2 to 3.9 in the 4 non-adjuvanted groups and from 27.9 to 60.5 in the adjuvanted groups. Conversion factors in the AS03 adjuvanted groups are largely superior to the 2.5 fold increase in GMT required by the European Authorities for interpandemic vaccines for adults (set forth in Table 1). Currently, for pandemic candidate vaccines the same criteria are applied as utilized for annual licensure of interpandemic influenza vaccine. Of note, all except the lowest antigen concentration adjuvanted groups achieve a conversion factor of 2.5 already after the first vaccination.

TABLE 10

Geometric mean titers (GMTs) for anti-HA antibody at different timepoints (ATP cohort for immunogenicity)

| Antibody | Group | Timing | N | GMT value | 95% CI LL | 95% CI UL | Min | Max |
|---|---|---|---|---|---|---|---|---|
| FLU A/VIET/04 AB | HN30 | PRE | 49 | 5.2 | 4.8 | 5.6 | <10.0 | 28.0 |
| | | PI(D 21) | 49 | 14.1 | 8.9 | 22.6 | <10.0 | 1280.0 |
| | | PII(D 42) | 49 | 20.0 | 12.5 | 32.1 | <10.0 | 905.0 |
| | HN15 | PRE | 49 | 5.3 | 4.8 | 5.9 | <10.0 | 40.0 |
| | | PI(D 21) | 49 | 10.4 | 6.9 | 15.6 | <10.0 | 640.0 |
| | | PII(D 42) | 49 | 14.7 | 9.6 | 22.4 | <10.0 | 640.0 |
| | HN8 | PRE | 49 | 5.0 | 5.0 | 5.0 | <10.0 | <10.0 |
| | | PI(D 21) | 49 | 6.8 | 5.4 | 8.7 | <10.0 | 160.0 |
| | | PII(D 42) | 49 | 8.5 | 6.3 | 11.5 | <10.0 | 160.0 |
| | HN4 | PRE | 50 | 5.0 | 5.0 | 5.0 | <10.0 | <10.0 |
| | | PI(D 21) | 50 | 5.1 | 4.9 | 5.4 | <10.0 | 20.0 |
| | | PII(D 42) | 50 | 6.2 | 5.3 | 7.4 | <10.0 | 57.0 |
| | HN30AD | PRE | 48 | 5.1 | 4.9 | 5.5 | <10.0 | 20.0 |
| | | PI(D 21) | 48 | 36.7 | 22.7 | 59.3 | <10.0 | 640.0 |
| | | PII(D 42) | 48 | 187.5 | 116.2 | 302.7 | <10.0 | 1280.0 |
| | HN15AD | PRE | 49 | 5.1 | 4.9 | 5.2 | <10.0 | 10.0 |
| | | PI(D 21) | 49 | 24.7 | 14.8 | 41.4 | <10.0 | 1280.0 |
| | | PII(D 42) | 49 | 306.7 | 218.4 | 430.8 | <10.0 | 1810.0 |
| | HN8AD | PRE | 50 | 5.4 | 4.8 | 6.0 | <10.0 | 40.0 |
| | | PI(D 21) | 50 | 24.6 | 15.8 | 38.4 | <10.0 | 640.0 |
| | | PII(D 42) | 50 | 205.3 | 135.1 | 312.0 | <10.0 | 1280.0 |
| | HN4AD | PRE | 50 | 5.4 | 4.8 | 6.0 | <10.0 | 80.0 |
| | | PI(D 21) | 50 | 12.9 | 8.9 | 18.7 | <10.0 | 640.0 |
| | | PII(D 42) | 50 | 149.3 | 93.2 | 239.1 | <10.0 | 1280.0 |

HN30 = H5N1 30 µg
HN15 = H5N1 15 µg
HN8 = H5N1 7.5 µg
HN4 = H5N1 3.8 µg
HN30AD = H5N1 30 µg + AS03
HN15AD = H5N1 15 µg + AS03
HN8AD = H5N1 7.5 µg + AS03
HN4AD = H5N1 3.8 µg + AS03
GMT = geometric mean antibody titre calculated on all subjects
N = number of subjects with available results
n/% = number/percentage of subjects with titre within the specified range
95% CI = 95% confidence interval; LL = Lower Limit, UL = Upper Limit
MIN/MAX = Minimum/Maximum
PRE = Pre-vaccination dose 1
PI(D 21) = Post-vaccination at day 21
PII(D 42) = Post-vaccination at day 42
Data source = Appendix table IIIA b) Conversion Factors of Anti-HI Antibody Titres, Seroprotection Rates and Seroconversion Rates (Correlates for Protection as Established for Influenza Vaccine in Humans)

The seroprotection rates (Table 12, FIG. 8) represent the proportion of subjects with a serum HI titre ≥40 on day 21 and 42. Prior to vaccination, 3 of the subjects (1 in group HN15, 1 in group HN8AD and 1 in group HN4D) were found to have protective levels of antibodies for vaccine strain H5N1 A/Vietnam/1194/2004. For H5N1 a very low percentage of seroprotected individuals prior to vaccination was obtained, confirming observation of previous studies (Bresson J L et al. *The Lancet.* 2006:367 (9523):1657-1664; Treanor J J et al. *N Engl J Med.* 2006; 354:1343-1351). At day 21, the seroprotection rates in the non-adjuvanted groups ranged from 0.0% to 28.6% (Table 12), while in the adjuvanted groups 26.0% to 58.3% of subjects achieved a protective titer. After the second dose of pandemic influenza candidate vaccine, 4.0 to 42.9% of subjects in the non-adjuvanted groups and 84.0% to 95.9% in the adjuvanted groups had a titer equal or above the threshold considered as protective (i.e. HI titer ≥1:40). Consequently, up to 95.9% of subjects (group 15HNAD) receiving an adjuvanted pandemic candidate vaccine had a serum HI titre ≥40 after 2 vaccinations and were deemed to be protected against the H5N1 vaccination strain. All four adjuvanted formulations exceeded the seroprotection rate of 70% required in the 18-60 year old population by the European Authorities—with a substantial proportion of subjects already achieving a protective titer after the first dose—while non of the non-adjuvanted candidates vaccines reached this criterion.

The seroconversion rates (Table 13, FIG. 7) represent the percentage of vaccinees that have either a prevaccination titer <1:10 and a post-vaccination titer ≥1:40 or a prevaccination titer ≥1:10 and at least a fourfold increase in post-vaccination titer on day 21 and 42 as compared to day 0. After the first vaccination, seroconversion rates in the non-adjuvanted groups ranged from 0.0% to 14.9% (Table 13). In the corresponding adjuvanted study groups, seroconversion rates between 24.0% and 58.3% were observed after the first vaccination, exceeding already, in 3 of the 4 adjuvanted groups receiving different antigen contents (adjuvanted formulations containing antigen doses above 7·5 μg), the requirements of the EMEA (seroconversion rate greater than 40% in the 18-60 year old population required) .—compared to none with the non-adjuvanted formulations. After the second vaccination between 4.0% and 40.8% of subjects in the non-adjuvanted groups, but 82.0% to 95.9% of subjects in the adjuvanted groups either achieved a seroconversion or four-fold increase. Therefore, after two vaccinations all four adjuvanted formulations of the candidate vaccine fulfilled the criterion for licensure as set by the EMEA, but only the highest dose of non-adjuvanted vaccine just achieved (HN30: 40.8%) this threshold.

TABLE 11

Seroconversion factor for HAI antibody titer at each post-vaccination time point (ATP cohort for immunogenicity)

| Vaccine strain | Timing | Group | N | GMR | 95% CI LL | 95% CI UL |
|---|---|---|---|---|---|---|
| FLU A/VIET/04 AB | PI(D 21) | HN30 | 49 | 2.7 | 1.7 | 4.3 |
| | | HN15 | 49 | 1.9 | 1.3 | 2.8 |
| | | HN8 | 49 | 1.4 | 1.1 | 1.7 |
| | | HN4 | 50 | 1.0 | 1.0 | 1.1 |
| | | HN30AD | 48 | 7.1 | 4.3 | 11.7 |
| | | HN15AD | 49 | 4.9 | 2.9 | 8.1 |
| | | HN8AD | 50 | 4.6 | 3.0 | 7.0 |
| | | HN4AD | 50 | 2.4 | 1.7 | 3.5 |
| | PII(D 42) | HN30 | 49 | 3.9 | 2.4 | 6.2 |
| | | HN15 | 49 | 2.8 | 1.9 | 4.1 |
| | | HN8 | 49 | 1.7 | 1.3 | 2.3 |
| | | HN4 | 50 | 1.2 | 1.1 | 1.5 |
| | | HN30AD | 48 | 36.4 | 22.7 | 58.5 |

TABLE 11-continued

Seroconversion factor for HAI antibody titer at each post-vaccination time point (ATP cohort for immunogenicity)

| Vaccine strain | Timing | Group | N | GMR | 95% CI LL | 95% CI UL |
|---|---|---|---|---|---|---|
| | | HN15AD | 49 | 60.5 | 42.8 | 85.5 |
| | | HN8AD | 50 | 38.1 | 24.8 | 58.4 |
| | | HN4AD | 50 | 27.9 | 17.2 | 45.2 |

HN30 = H5N1 30 μg
HN15 = H5N1 15 μg
HN8 = H5N1 7.5 μg
HN4 = H5N1 3.8 μg
HN30AD = H5N1 30 μg + AS03
HN15AD = H5N1 15 μg + AS03
HN8AD = H5N1 7.5 μg + AS03
HN4AD = H5N1 3.8 μg + AS03
N = number of subjects with available results
n/% = number/percentage of subjects with titre within the specified range
PRE = Pre-vaccination
PI(D 21) = Post vaccination at day 21
PII(D 42) = Post vaccination at day 42

TABLE 12

Seroprotection rates at days 0, day 21 and day 42 defined as the percentage of vaccinees with the serum anti-HA titer ≥1:40 (ATP cohort for immunogenicity)

| Antibody | Group | Timing | ≥40 1/DIL N | n | % | 95% CI LL | 95% CI UL |
|---|---|---|---|---|---|---|---|
| FLU A/ VIET/ 04 AB | HN30 | PRE | 49 | 0 | 0.0 | 0.0 | 7.3 |
| | | PI(D 21) | 49 | 14 | 28.6 | 16.6 | 43.3 |
| | | PII(D 42) | 49 | 21 | 42.9 | 28.8 | 57.8 |
| | HN15 | PRE | 49 | 1 | 2.0 | 0.1 | 10.9 |
| | | PI(D 21) | 49 | 10 | 20.4 | 10.2 | 34.3 |
| | | PII(D 42) | 49 | 17 | 34.7 | 21.7 | 49.6 |
| | HN8 | PRE | 49 | 0 | 0.0 | 0.0 | 7.3 |
| | | PI(D 21) | 49 | 4 | 8.2 | 2.3 | 19.6 |
| | | PII(D 42) | 49 | 8 | 16.3 | 7.3 | 29.7 |
| | HN4 | PRE | 50 | 0 | 0.0 | 0.0 | 7.1 |
| | | PI(D 21) | 50 | 0 | 0.0 | 0.0 | 7.1 |
| | | PII(D 42) | 50 | 2 | 4.0 | 0.5 | 13.7 |
| | HN30AD | PRE | 48 | 0 | 0.0 | 0.0 | 7.4 |
| | | PI(D 21) | 48 | 28 | 58.3 | 43.2 | 72.4 |
| | | PII(D 42) | 48 | 41 | 85.4 | 72.2 | 93.9 |
| | HN15AD | PRE | 49 | 0 | 0.0 | 0.0 | 7.3 |
| | | PI(D 21) | 49 | 24 | 49.0 | 34.4 | 63.7 |
| | | PII(D 42) | 49 | 47 | 95.9 | 86.0 | 99.5 |
| | HN8AD | PRE | 50 | 1 | 2.0 | 0.1 | 10.7 |
| | | PI(D 21) | 50 | 25 | 50.0 | 35.5 | 64.5 |
| | | PII(D 42) | 50 | 45 | 90.0 | 78.2 | 96.7 |
| | HN4AD | PRE | 50 | 1 | 2.0 | 0.1 | 10.7 |
| | | PI(D 21) | 50 | 13 | 26.0 | 14.6 | 40.3 |
| | | PII(D 42) | 50 | 42 | 84.0 | 70.9 | 92.8 |

HN30 = H5N1 30 μg
HN15 = H5N1 15 μg
HN8 = H5N1 7.5 μg
HN4 = H5N1 3.8 μg
HN30AD = H5N1 30 μg + AS03
HN15AD = H5N1 15 μg + AS03
HN8AD = H5N1 7.5 μg + AS03
HN4AD = H5N1 3.8 μg + AS03
N = number of subjects with available results
n/% = number/percentage of subjects with titre within the specified range
PRE = Pre-vaccination
PI(D 21) = Post vaccination at day 21
PII(D 42) = Post vaccination at day 42

TABLE 13

Seroconversion rates for anti-HA antibody titer at each post-vaccination at day 21 and day 42 (ATP cohort for immunogenicity)

| Vaccine strain | Timing | Group | N | n | Seroconversion % | 95% CI LL | 95% CI UL |
|---|---|---|---|---|---|---|---|
| FLU A/ VIET/ 04 AB | PI(D 21) | HN30 | 49 | 13 | 26.5 | 14.9 | 41.1 |
| | | HN15 | 49 | 10 | 20.4 | 10.2 | 34.3 |
| | | HN8 | 49 | 4 | 8.2 | 2.3 | 19.6 |
| | | HN4 | 50 | 0 | 0.0 | 0.0 | 7.1 |
| | | HN30AD | 48 | 28 | 58.3 | 43.2 | 72.4 |
| | | HN15AD | 49 | 24 | 49.0 | 34.4 | 63.7 |
| | | HN8AD | 50 | 25 | 50.0 | 35.5 | 64.5 |
| | | HN4AD | 50 | 12 | 24.0 | 13.1 | 38.2 |
| | PII(D 42) | HN30 | 49 | 20 | 40.8 | 27.0 | 55.8 |
| | | HN15 | 49 | 17 | 34.7 | 21.7 | 49.6 |
| | | HN8 | 49 | 8 | 16.3 | 7.3 | 29.7 |
| | | HN4 | 50 | 2 | 4.0 | 0.5 | 13.7 |
| | | HN30AD | 48 | 41 | 85.4 | 72.2 | 93.9 |
| | | HN15AD | 49 | 47 | 95.9 | 86.0 | 99.5 |
| | | HN8AD | 50 | 45 | 90.0 | 78.2 | 96.7 |
| | | HN4AD | 50 | 41 | 82.0 | 68.6 | 91.4 |

HN30 = H5N1 30 μg
HN15 = H5N1 15 μg
HN8 = H5N1 7.5 μg
HN4 = H5N1 3.8 μg
HN30AD = H5N1 30 μg + AS03
HN15AD = H5N1 15 μg + AS03
HN8AD = H5N1 7.5 μg + AS03
HN4AD = H5N1 3.8 μg + AS03
N = number of subjects with available results
PI(D 21) = Post vaccination at 21 days
PII(D 42) = Post vaccination at 42 days
Data source = Appendix table IIIA
n/% = number/percentage of subjects with either a pre-vaccination titer <1:10 and post-vaccination titre ≥1:40 or a pre-vaccination titer ≥1:10 and a minimum 4-fold increase in pot-vaccination titer.
95% confidence interval, LL = Lower Limit, UL = Upper Limit In Conclusion:

In case of an influenza pandemic, large proportions of the population will be naïve towards the pandemic influenza strain and will likely require 2 doses of vaccine to be protected. To reduce the antigen content in the potential pandemic vaccine and therefore increase vaccine supply, adjuvantation strategies are employed after it has been shown that non-adjuvanted H5N1 candidates vaccines (H5N1 is a leading candidate for causing the next influenza pandemic) elicit a immune response only after large doses of antigen (Treanor J J et al. *N Engl J Med.* 2006; 354:1343-1351).

In this first trial reported herein with a H5N1 pandemic influenza candidate vaccine with AS03, the following results were obtained:

There is a clear benefit of the adjuvant AS03 in comparison to the plain antigen formulations for all different hemagglutinin doses tested. Post second vaccination, there was a clear superiority of the adjuvanted groups in GMTs of HI antibody observed: The GMT of the adjuvanted group receiving the lowest antigen dose (3.8 μg HA) tested was still 7.5 fold higher than the highest GMT achieved in the non-adjuvanted groups, elicited by the highest antigen dose (2 injections a 30 μg of HA). There was no overlap of 95% CI between either of the adjuvanted groups with either of the non-adjuvanted groups at day 42.

The seroconversion rates at day 42 were 82.0%, 90.0%, 95.9% and 85.6% for the 3.8 μg, 7.5 μg, 15 μg and 30 μg plus adjuvant groups, respectively. This is for all four antigen contents adjuvanted with AS03 tested superior to the 40% required by the European Authorities. Only one of the non adjuvanted groups, the highest antigen dose group (30 μg), was just able to accomplish a percentage above the set threshold.

At day 42, the seroprotection rates in the four adjuvanted groups were 84.0%, 90.0%, 95.9% and 85.4% for the 3.8 μg, 7.5 μg, 15 μg and 30 μg plus adjuvant groups, respectively. The required percentage by the EMEA for the adult age group below 60 years of age is 70%, thereby all adjuvanted groups fulfilled this criterion, while non of the plain non adjuvanted groups could achieved the seroprotection rate required.

In this study, after two vaccinations with the different candidate vaccine formulations, the seroconversion factor was greater than 27.9 (see Table 11, value reached for the HN4AD group) for the four adjuvanted groups, thereby exceeding largely the requirement set at 2.5. Also for the non-adjuvanted groups, the 2 groups receiving the highest antigen doses (15 μg and 30 μg) fulfilled the requirement with 2.8 (HN15 group) and 3.9 (HN30 group).

Regarding the three criteria as set out by the EMEA which are also applicable for the evaluation of pandemic influenza candidate vaccines, all adjuvanted groups achieved after the second dose of the respective H5N1 vaccine adjuvanted with AS03 all three criteria defined for this age group. All adjuvanted groups also achieved the FDA proposed criteria for seroconversion, seroprotection and conversion factor, after the second dose.

IV.7.1.2 Anti-Hemagglutinin Antibody Response Heterologous Strain

Assessing immunogenicity against an antigenically different H5N1 strain from the vaccine strain is considered to allow further assess the potential of a pandemic vaccine candidate. Cross reactivity testing is performed on the sera of subjects who have received the vaccination strain and assesses the potential of the antibodies induced by the vaccine to react to an antigenically different strain. For evaluation of cross reactivity, H5N1 A/Indonesia/5/2005 was chosen. H5N1 A/Indonesia belongs to Clade 2, whereas H5N1 A/Vietnam/1194/2004, the vaccine strain, belongs to Clade 1, and is the first pandemic vaccine prototype strain from the new genetic group released by WHO. Both strains can be therefore considered antigenically different.

a) Geometric Mean Titres and Seropositivity Against H5N1 Indonesia in Study H5N1-007 (Table 14)

Seropositive was defined as a HI antibody titer of 1:10. All subjects were seronegative for Indonesia prior to the first vaccination with the Vietnam strain. After the second vaccination, up to 48% of subjects of the adjuvanted groups (28% 3.8 μg group, 48% 7.5 μg group, 26.5% 15 μg group, 33.3% 30 μg group) achieved a status of seropositivity. In comparison, no seropositivity was observed in the 3.8, 7.5 and 15 μg non-adjuvanted groups at all, while only 2% (1 subject) was found to be seropositive for H5N1 Indonesia in the highest antigen non adjuvanted group (30 μg).

TABLE 14

Seropositivity rates and GMTs for HI antibody titer at day 0, day 21 and day 42 by vaccine group (ATP cohort for immunogenicity)

| | | | | | | >=10 1/DIL | | | GMT | | | | |
|---|---|---|---|---|---|---|---|---|---|---|---|---|---|
| | | | | | | | 95% CI | | | 95% CI | | | |
| Strain | Group | Timing | N | n | % | LL | UL | value | LL | UL | Min | Max |
| FLU A/IND/05 AB | HN30 | PRE | 49 | 0 | 0.0 | 0.0 | 7.3 | 5.0 | 5.0 | 5.0 | <10.0 | <10.0 |
| | | PI(D21) | 49 | 1 | 2.0 | 0.1 | 10.9 | 5.1 | 4.9 | 5.4 | <10.0 | 20.0 |
| | | PII(D42) | 49 | 1 | 2.0 | 0.1 | 10.9 | 5.1 | 4.9 | 5.2 | <10.0 | 10.0 |
| | HN15 | PRE | 49 | 0 | 0.0 | 0.0 | 7.3 | 5.0 | 5.0 | 5.0 | <10.0 | <10.0 |
| | | PI(D21) | 49 | 0 | 0.0 | 0.0 | 7.3 | 5.0 | 5.0 | 5.0 | <10.0 | <10.0 |
| | | PII(D42) | 49 | 0 | 0.0 | 0.0 | 7.3 | 5.0 | 5.0 | 5.0 | <10.0 | <10.0 |
| | HN8 | PRE | 49 | 0 | 0.0 | 0.0 | 7.3 | 5.0 | 5.0 | 5.0 | <10.0 | <10.0 |
| | | PI(D21) | 49 | 0 | 0.0 | 0.0 | 7.3 | 5.0 | 5.0 | 5.0 | <10.0 | <10.0 |
| | | PII(D42) | 49 | 0 | 0.0 | 0.0 | 7.3 | 5.0 | 5.0 | 5.0 | <10.0 | <10.0 |
| | HN4 | PRE | 49 | 0 | 0.0 | 0.0 | 7.3 | 5.0 | 5.0 | 5.0 | <10.0 | <10.0 |
| | | PI(D21) | 49 | 0 | 0.0 | 0.0 | 7.3 | 5.0 | 5.0 | 5.0 | <10.0 | <10.0 |
| | | PII(D42) | 50 | 0 | 0.0 | 0.0 | 7.1 | 5.0 | 5.0 | 5.0 | <10.0 | <10.0 |
| | HN30AD | PRE | 48 | 0 | 0.0 | 0.0 | 7.4 | 5.0 | 5.0 | 5.0 | <10.0 | <10.0 |
| | | PI(D21) | 48 | 4 | 8.3 | 2.3 | 20.0 | 5.9 | 4.9 | 7.1 | <10.0 | 226.0 |
| | | PII(D42) | 48 | 16 | 33.3 | 20.4 | 48.4 | 11.7 | 8.0 | 17.2 | <10.0 | 226.0 |
| | HN15AD | PRE | 48 | 0 | 0.0 | 0.0 | 7.4 | 5.0 | 5.0 | 5.0 | <10.0 | <10.0 |
| | | PI(D21) | 49 | 2 | 4.1 | 0.5 | 14.0 | 5.4 | 4.8 | 6.0 | <10.0 | 80.0 |
| | | PII(D42) | 49 | 13 | 26.5 | 14.9 | 41.1 | 10.2 | 7.1 | 14.7 | <10.0 | 226.0 |
| | HN8AD | PRE | 50 | 0 | 0.0 | 0.0 | 7.1 | 5.0 | 5.0 | 5.0 | <10.0 | <10.0 |
| | | PI(D21) | 50 | 4 | 8.0 | 2.2 | 19.2 | 5.7 | 5.0 | 6.4 | <10.0 | 40.0 |
| | | PII(D42) | 50 | 24 | 48.0 | 33.7 | 62.6 | 13.9 | 9.7 | 20.1 | <10.0 | 320.0 |
| | HN4AD | PRE | 50 | 0 | 0.0 | 0.0 | 7.1 | 5.0 | 5.0 | 5.0 | <10.0 | <10.0 |
| | | PI(D21) | 50 | 1 | 2.0 | 0.1 | 10.6 | 5.1 | 4.9 | 5.4 | <10.0 | 20.0 |
| | | PII(D42) | 50 | 14 | 28.0 | 16.2 | 42.5 | 9.9 | 7.0 | 14.0 | <10.0 | 226.0 |

HN30 = H5N1 30 μg,
HN15 = H5N1 15 μg,
HN8 = H5N1 7.5 μg,
HN4 = H5N1 3.8 μg
HN30AD = H5N1 30 μg + AS03,
HN15AD = H5N1 15 μg + AS03,
HN8AD = H5N1 7.5 μg + AS03,
HN4AD = H5N1 3.8 μg + AS03
N = Number of subjects with available results
n/% = number/percentage of seropositive subjects (HI titer >=1:10)
95% CI = 95% confidence interval,
LL = Lower Limit,
UL = Upper Limit
GMT = Geometric Mean antibody Titer
Min/Max = Minimum/Maximum
PRE = Pre-vaccination dose 1 (Day 0)
PI(D21) = 21 days after first vaccination (Day 21)
PII(D42) = 21 days after second vaccination (Day 42)

b) Seroprotection Against H5N1 Indonesia in Study H5N1-007 (Table 15)

After the second vaccination, despite a much lower sensitivity of HI assay, HI seroprotective titers against the A/Indonesia 5/05 strain were detectable at day 42, in 20.0% [95% CI: 10.0-33.7] and 32.0% [19.5-46.7] of subjects in the 3.8 μg and 7.5 μg HA adjuvanted vaccine groups but none of the subjects in the corresponding non-adjuvanted groups. In the 15 μg and 30 μg adjuvanted group, 20.4% and 29.2% of subjects had a titer of 1:40 after the second vaccination, respectively. None of the subjects in the non-adjuvanted groups were seroprotected.

TABLE 15

Seroprotection rates (SP) for HI antibody titer at day 0, day 21 and day 42 by vaccine group (ATP cohort for immunogenicity)

| | | | | | | SP | | | |
|---|---|---|---|---|---|---|---|---|---|
| | | | | | | | 95% CI | n | % |
| Vaccine strain | Vaccine Group | Timing | N | n | % | LL | UL | UNPROT | UNPROT |
| FLU A/IND/05 AB | HN30 | PRE | 49 | 0 | 0.0 | 0.00 | 7.25 | 49 | 100.0 |
| | | PI(D21) | 49 | 0 | 0.0 | 0.00 | 7.25 | 49 | 100.0 |
| | | PII(D42) | 49 | 0 | 0.0 | 0.00 | 7.25 | 49 | 100.0 |
| | HN15 | PRE | 49 | 0 | 0.0 | 0.00 | 7.25 | 49 | 100.0 |
| | | PI(D21) | 49 | 0 | 0.0 | 0.00 | 7.25 | 49 | 100.0 |
| | | PII(D42) | 49 | 0 | 0.0 | 0.00 | 7.25 | 49 | 100.0 |

TABLE 15-continued

Seroprotection rates (SP) for HI antibody titer at day 0, day 21 and day 42 by vaccine group (ATP cohort for immunogenicity)

| Vaccine strain | Vaccine Group | Timing | N | n | % | 95% CI LL | 95% CI UL | n UNPROT | % UNPROT |
|---|---|---|---|---|---|---|---|---|---|
| | HN8 | PRE | 49 | 0 | 0.0 | 0.00 | 7.25 | 49 | 100.0 |
| | | PI(D21) | 49 | 0 | 0.0 | 0.00 | 7.25 | 49 | 100.0 |
| | | PII(D42) | 49 | 0 | 0.0 | 0.00 | 7.25 | 49 | 100.0 |
| | HN4 | PRE | 49 | 0 | 0.0 | 0.00 | 7.25 | 49 | 100.0 |
| | | PI(D21) | 49 | 0 | 0.0 | 0.00 | 7.25 | 49 | 100.0 |
| | | PII(D42) | 50 | 0 | 0.0 | 0.00 | 7.11 | 50 | 100.0 |
| | HN30AD | PRE | 48 | 0 | 0.0 | 0.00 | 7.40 | 48 | 100.0 |
| | | PI(D21) | 48 | 2 | 4.2 | 0.51 | 14.25 | 46 | 95.8 |
| | | PII(D42) | 48 | 14 | 29.2 | 16.95 | 44.06 | 34 | 70.8 |
| | HN15AD | PRE | 48 | 0 | 0.0 | 0.00 | 7.40 | 48 | 100.0 |
| | | PI(D21) | 49 | 1 | 2.0 | 0.05 | 10.85 | 48 | 98.0 |
| | | PII(D42) | 49 | 10 | 20.4 | 10.24 | 34.34 | 39 | 79.6 |
| | HN8AD | PRE | 50 | 0 | 0.0 | 0.00 | 7.11 | 50 | 100.0 |
| | | PI(D21) | 50 | 1 | 2.0 | 0.05 | 10.65 | 49 | 98.0 |
| | | PII(D42) | 50 | 16 | 32.0 | 19.52 | 46.70 | 34 | 68.0 |
| | HN4AD | PRE | 50 | 0 | 0.0 | 0.00 | 7.11 | 50 | 100.0 |
| | | PI(D21) | 50 | 0 | 0.0 | 0.00 | 7.11 | 50 | 100.0 |
| | | PII(D42) | 50 | 10 | 20.0 | 10.03 | 33.72 | 40 | 80.0 |

HN30 = H5N1 30 μg,
HN15 = H5N1 15 μg,
HN8 = H5N1 7.5 μg,
HN4 = H5N1 3.8 μg
HN30AD = H5N1 30 μg + AS03,
HN15AD = H5N1 15 μg + AS03,
HN8AD = H5N1 7.5 μg + AS03,
HN4AD = H5N1 3.8 μg + AS03
PRE = Pre-vaccination dose 1 (Day 0)
PI(D21) = 21 days after first vaccination (Day 21)
PII(D42) = 21 days after second vaccination (Day 42)
N = Number of subjects with available results
n/% = Number/percentage of seroprotected subjects (HI titer >=1:40)
n/% UNPROT = Number/percentage of unprotected subjects (HI titer <1:40)
95% CI = 95% confidence interval,
LL = Lower Limit,
UL = Upper Limit c) Seroconversion Against H5N1 Indonesia in Study H5N1-007 (Table 16)

Up to 32.0% of subjects in the adjuvanted groups achieved seroconversion against the Indonesia strain not contained in the vaccine. In the 3.8 μg, 7.5 μg, 15 μg and 30 μg adjuvanted group, 20.0%, 32.0%, 20.8% and 29.2% of subjects seroconverted after the second vaccination, respectively. For none of the subjects in the non-adjuvanted groups seroconversion could be demonstrated.

TABLE 16

Seroconversion rate (SC) for HI antibody titer at day 21 and day 42 by vaccine group (ATP cohort for immunogenicity)

| Vaccine Strain | Vaccine Group | Timing | N | n | % | 95% CI LL | 95% CI UL |
|---|---|---|---|---|---|---|---|
| FLU A/IND/05 AB | HN30 | PI(D21) | 49 | 0 | 0.0 | 0.0 | 7.3 |
| | | PII(D42) | 49 | 0 | 0.0 | 0.0 | 7.3 |
| | HN15 | PI(D21) | 49 | 0 | 0.0 | 0.0 | 7.3 |
| | | PII(D42) | 49 | 0 | 0.0 | 0.0 | 7.3 |
| | HN8 | PI(D21) | 49 | 0 | 0.0 | 0.0 | 7.3 |
| | | PII(D42) | 49 | 0 | 0.0 | 0.0 | 7.3 |
| | HN4 | PI(D21) | 48 | 0 | 0.0 | 0.0 | 7.4 |
| | | PII(D42) | 49 | 0 | 0.0 | 0.0 | 7.3 |
| | HN30AD | PI(D21) | 48 | 2 | 4.2 | 0.5 | 14.3 |
| | | PII(D42) | 48 | 14 | 29.2 | 17.0 | 44.1 |
| | HN15AD | PI(D21) | 48 | 1 | 2.1 | 0.1 | 11.1 |
| | | PII(D42) | 48 | 10 | 20.8 | 10.5 | 35.0 |
| | HN8AD | PI(D21) | 50 | 1 | 2.0 | 0.1 | 10.6 |
| | | PII(D42) | 50 | 16 | 32.0 | 19.5 | 46.7 |
| | HN4AD | PI(D21) | 50 | 0 | 0.0 | 0.0 | 7.1 |
| | | PII(D42) | 50 | 10 | 20.0 | 10.0 | 33.7 |

HN30 = H5N1 30 μg,
HN15 = H5N1 15 μg,
HN8 = H5N1 7.5 μg,
HN4 = H5N1 3.8 μg
HN30AD = H5N1 30 μg + AS03,
HN15AD = H5N1 15 μg + AS03,
HN8AD = H5N1 7.5 μg + AS03,
HN4AD = H5N1 3.8 μg + AS03
PI(D21) = 21 days after first vaccination (Day 21),
PII(D42) = 21 days after second vaccination (Day 42)
N = number of subjects with available results
n/% = number/percentage who seroconverted at the specified POST
95% CI = 95% confidence interval,
LL = Lower Limit,
UL = Upper Limit d) Seroconversion Factor Against H5N1 Indonesia in Study H5N1-007

Seroconversion factors between 2 and 2.8 were achieved by the adjuvanted groups in the trial. In the 3.8 µg, 7.5 µg, 15 µg and 30 µg adjuvanted group, the seroconversion factor was 2.0, 2.8, 2.1 and 2.3, respectively.

e) Conclusion on Cross Reactive Data Against H5N1 A/Indonesia

In conclusion, after 2 doses of a split virus candidate vaccine adjuvanted with AS03 adjuvant, cross reactivity data obtained for a H5N1 strain from a different clade than the vaccine strain, which has caused considerable morbidity and mortality in humans in Asia, were positive. Up to 48% of subjects showed sign of being primed and up to 32% of subjects were actually seroprotected against the non vaccine strain. These results show that adjuvantation of a pandemic vaccine can provide cross-reactivity against a drift variant of the pandemic strain used in the vaccine candidate. These results are confirming the potential of the adjuvanted vaccine for priming and cross-priming.

IV.7.1.3 Neutralizing Antibody Response to Homologous Strain H5N1 A/Vietnam

The neutralisation assay is a method which allows for the quantification of antibodies that inhibit the attachment, the penetration as well as the propagation of Influenza virus into cells. While for the haemagglutinin inhibition assay a seroprotection threshold is established, this is not the case for this assay. Alternatively, a four-fold increase in neutralizing titre can be used to evaluate whether vaccinated individuals have responded against the vaccination strain or a heterologous strain. Seroconversion rate is one of the key immunogenicity parameter used by CHMP/FDA to evaluate effectiveness of candidate Influenza vaccines. Testing of serum samples in such neutralization assay using drift strain would allow predicting, at least, the frequency of individuals who have been "primed" against a given strain different from the vaccine strain.

a) Geometric Mean Titres and Seropositivity Measured in Neutralization Assay Against H5N1 Vietnam in Study H5N1-007 (Table 17)

a)1. Interim Data Obtained on a Limited Number of Subjects Per Groups

The threshold for seropositivity is set at a titre of ≥1:28, the Neutralization assay is also a highly sensitive test. GMT's at day 0 ranged from 14.0 to 18.1 in the non adjuvanted and from 18.5 to 25.2 in the adjuvanted groups. After the second vaccination, titres increased for the non adjuvanted groups as a dose dependent manner to 43.9, 61.7, 86.9 and 177.8 for the 3.8, 7.5, 15 and 30 µg groups respectively. In the adjuvanted groups, titres of 381.0, 421.2, 464.7 and 333.3 for the 3.8, 7.5, 15 and 30 µg groups respectively were achieved, exactly repeating the observation made in HI titers: from 3.8 µg over 7.5 µg to the 15 µg adjuvanted group a dose dependant increase in GMT was observed (Table 17A and FIG. 10A1).

TABLE 17A

Seropositivity rates and GMTs for Neutralizing antibody titer at day 0, day 21 and day 42 (ATP cohort for immunogenicity)

| | | | | | >=28 1/DIL | | | GMT | | | | |
| | | | | | | 95% CI | | | 95% CI | | | |
| Strain | Group | Timing | N | n | % | LL | UL | value | LL | UL | Min | Max |
|---|---|---|---|---|---|---|---|---|---|---|---|---|
| FLU A/ VIET/04 AB | HN30 | PRE | 25 | 4 | 16.0 | 4.5 | 36.1 | 18.2 | 14.0 | 23.6 | <28.0 | 113.0 |
| | | PI(D21) | 25 | 23 | 92.0 | 74.0 | 99.0 | 114.1 | 76.3 | 170.7 | <28.0 | 905.0 |
| | | PII(D42) | 25 | 25 | 100 | 86.3 | 100 | 177.8 | 120.5 | 262.2 | 28.0 | 905.0 |
| | HN15 | PRE | 43 | 15 | 34.9 | 21.0 | 50.9 | 23.0 | 18.1 | 29.4 | <28.0 | 226.0 |
| | | PI(D21) | 43 | 34 | 79.1 | 64.0 | 90.0 | 70.0 | 48.5 | 101.0 | <28.0 | 905.0 |
| | | PII(D42) | 43 | 38 | 88.4 | 74.9 | 96.1 | 86.9 | 63.6 | 118.9 | <28.0 | 720.0 |
| | HN8 | PRE | 40 | 13 | 32.5 | 18.6 | 49.1 | 21.8 | 17.4 | 27.3 | <28.0 | 113.0 |
| | | PI(D21) | 40 | 29 | 72.5 | 56.1 | 85.4 | 44.7 | 33.7 | 59.4 | <28.0 | 226.0 |
| | | PII(D42) | 40 | 34 | 85.0 | 70.2 | 94.3 | 61.7 | 47.5 | 80.1 | <28.0 | 284.0 |
| | HN4 | PRE | 43 | 13 | 30.2 | 17.2 | 46.1 | 20.8 | 16.9 | 25.5 | <28.0 | 113.0 |
| | | PI(D21) | 43 | 30 | 69.8 | 53.9 | 82.8 | 40.0 | 30.8 | 52.0 | <28.0 | 226.0 |
| | | PII(D42) | 43 | 33 | 76.7 | 61.4 | 88.2 | 43.9 | 34.4 | 55.9 | <28.0 | 284.0 |
| | HN30AD | PRE | 25 | 6 | 24.0 | 9.4 | 45.1 | 18.5 | 14.9 | 23.1 | <28.0 | 57.0 |
| | | PI(D21) | 25 | 24 | 96.0 | 79.6 | 99.9 | 200.3 | 137.3 | 292.2 | <28.0 | 905.0 |
| | | PII(D42) | 25 | 25 | 100 | 86.3 | 100 | 333.3 | 246.7 | 450.4 | 57.0 | 1420.0 |
| | HN15AD | PRE | 43 | 14 | 32.6 | 19.1 | 48.5 | 22.3 | 17.8 | 28.0 | <28.0 | 180.0 |
| | | PI(D21) | 43 | 43 | 100 | 91.8 | 100 | 203.1 | 161.4 | 255.6 | 57.0 | 905.0 |
| | | PII(D42) | 43 | 43 | 100 | 91.8 | 100 | 464.7 | 372.7 | 579.4 | 113.0 | 2260.0 |
| | HN8AD | PRE | 42 | 16 | 38.1 | 23.6 | 54.4 | 25.2 | 19.2 | 33.1 | <28.0 | 284.0 |
| | | PI(D21) | 42 | 41 | 97.6 | 87.4 | 99.9 | 160.7 | 121.5 | 212.6 | <28.0 | 1420.0 |
| | | PII(D42) | 42 | 41 | 97.6 | 87.4 | 99.9 | 421.2 | 319.4 | 555.4 | <28.0 | 1440.0 |
| | HN4AD | PRE | 44 | 16 | 36.4 | 22.4 | 52.2 | 23.0 | 18.5 | 28.6 | <28.0 | 113.0 |
| | | PI(D21) | 44 | 43 | 97.7 | 88.0 | 99.9 | 135.9 | 109.4 | 168.9 | <28.0 | 905.0 |
| | | PII(D42) | 43 | 43 | 100 | 91.8 | 100 | 381.0 | 306.0 | 474.4 | 57.0 | 1420.0 |

HN30 = H5N1 30 µg;
HN15 = H5N1 15 µg;
HN8 = H5N1 7.5 µg;
HN4 = H5N1 3.8 µg
HN30AD = H5N1 30 µg + AS03;
HN15AD = H5N1 15 µg + AS03;
HN8AD = H5N1 7.5 µg + AS03;
HN4AD = H5N1 3.8 µg + AS03
N = Number of subjects with available results
n/% = number/percentage of seropositive subjects (HI titer >=1:10)

TABLE 17A-continued

Seropositivity rates and GMTs for Neutralizing antibody titer at day 0,
day 21 and day 42 (ATP cohort for immunogenicity)

| | | | | | | >=28 1/DIL | | | GMT | | | | |
|---|---|---|---|---|---|---|---|---|---|---|---|---|---|
| | | | | | | | 95% CI | | | 95% CI | | | |
| Strain | Group | Timing | N | n | % | LL | UL | value | LL | UL | Min | Max | |

95% CI = 95% confidence interval,
LL = Lower Limit,
UL = Upper Limit
GMT = Geometric Mean antibody Titer
Min/Max = Minimum/Maximum
PRE = Pre-vaccination dose 1 (Day 0)
PI(D21) = 21 days after first vaccination (Day 21)
PII(D42) = 21 days after second vaccination (Day 42)

a)2. Data Obtained on the Total Cohort

The threshold for seropositivity is set at a titre of ≥1:28, the Neutralization assay is also a highly sensitive test. GMT's at day 0 ranged from 18.9 to 22.6 in the non adjuvanted and from 17.3 to 23.3 in the adjuvanted groups. After the second vaccination, titres increased for the non adjuvanted groups as a dose dependent manner to 40.7, 53.4, 80.1 and 113.6 for the 3.8, 7.5, 15 and 30 µg groups respectively. In the adjuvanted groups, titres of 314.7, 343.0, 400.1 and 258.2 for the 3.8, 7.5, 15 and 30 µg groups respectively were achieved, exactly repeating the observation made in HI titers: from 3.8 µg over 7.5 µg to the 15 µg adjuvanted group a dose dependant increase in GMT was observed (Table 17B and FIG. 10A2).

TABLE 17B

Seropositivity rates and GMTs (with 95% CI) for the neutralizing
antibodies against the vaccine strain (Vietnam strain) at Day 0, Day 21
and Day 42 (ATP cohort for Immunogenicity)

| | | | | | | ≥28 1/DIL | | | GMT | | | |
|---|---|---|---|---|---|---|---|---|---|---|---|---|
| | | | | | | | 95% CI | | | 95% CI | | |
| Antibody | Group | Timing | N | n | % | LL | UL | value | LL | UL | Min | Max |
| FLU A/VIET/04 AB | HN30 | PRE | 49 | 12 | 24.5 | 13.3 | 38.9 | 18.9 | 16.0 | 22.3 | <28.0 | 113.0 |
| | | PI(D21) | 49 | 44 | 89.8 | 77.8 | 96.6 | 80.1 | 61.0 | 105.3 | <28.0 | 905.0 |
| | | PII(D42) | 48 | 46 | 95.8 | 85.7 | 99.5 | 113.6 | 85.5 | 150.9 | <28.0 | 905.0 |
| | HN15 | PRE | 49 | 17 | 34.7 | 21.7 | 49.6 | 22.6 | 18.2 | 28.2 | <28.0 | 226.0 |
| | | PI(D21) | 48 | 38 | 79.2 | 65.0 | 89.5 | 66.9 | 47.9 | 93.4 | <28.0 | 905.0 |
| | | PII(D42) | 49 | 43 | 87.8 | 75.2 | 95.4 | 80.1 | 60.1 | 107.0 | <28.0 | 720.0 |
| | HN8 | PRE | 49 | 15 | 30.6 | 18.3 | 45.4 | 20.9 | 17.2 | 25.2 | <28.0 | 113.0 |
| | | PI(D21) | 49 | 33 | 67.3 | 52.5 | 80.1 | 40.3 | 31.2 | 52.1 | <28.0 | 226.0 |
| | | PII(D42) | 49 | 38 | 77.6 | 63.4 | 88.2 | 53.4 | 41.6 | 68.6 | <28.0 | 284.0 |
| | HN4 | PRE | 50 | 14 | 28.0 | 16.2 | 42.5 | 20.2 | 16.8 | 24.3 | <28.0 | 113.0 |
| | | PI(D21) | 50 | 31 | 62.0 | 47.2 | 75.3 | 35.5 | 27.8 | 45.4 | <28.0 | 226.0 |
| | | PII(D42) | 50 | 36 | 72.0 | 57.5 | 83.8 | 40.7 | 32.4 | 51.0 | <28.0 | 284.0 |
| | HN30AD | PRE | 48 | 9 | 18.8 | 8.9 | 32.6 | 17.3 | 15.1 | 20.0 | <28.0 | 90.0 |
| | | PI(D21) | 47 | 45 | 95.7 | 85.5 | 99.5 | 146.6 | 113.3 | 189.8 | <28.0 | 905.0 |
| | | PII(D42) | 47 | 47 | 100 | 92.5 | 100 | 258.2 | 205.5 | 324.5 | 28.0 | 1420.0 |
| | HN15AD | PRE | 49 | 16 | 32.7 | 19.9 | 47.5 | 22.0 | 17.9 | 27.0 | <28.0 | 180.0 |
| | | PI(D21) | 49 | 49 | 100 | 92.7 | 100 | 181.3 | 144.6 | 227.3 | 45.0 | 905.0 |
| | | PII(D42) | 49 | 49 | 100 | 92.7 | 100 | 400.1 | 319.3 | 501.4 | 113.0 | 2260.0 |
| | HN8AD | PRE | 50 | 17 | 34.0 | 21.2 | 48.8 | 23.3 | 18.4 | 29.4 | <28.0 | 284.0 |
| | | PI(D21) | 49 | 47 | 95.9 | 86.0 | 99.5 | 134.6 | 101.3 | 178.7 | <28.0 | 1420.0 |
| | | PII(D42) | 50 | 49 | 98.0 | 89.4 | 99.9 | 343.0 | 260.5 | 451.5 | <28.0 | 1440.0 |
| | HN4AD | PRE | 50 | 16 | 32.0 | 19.5 | 46.7 | 21.7 | 17.8 | 26.4 | <28.0 | 113.0 |
| | | PI(D21) | 50 | 48 | 96.0 | 86.3 | 99.5 | 117.9 | 93.7 | 148.3 | <28.0 | 905.0 |
| | | PII(D42) | 49 | 48 | 98.0 | 89.1 | 99.9 | 314.7 | 243.1 | 407.3 | <28.0 | 1420.0 |

HN30 = H5N1 30 µg
HN15 = H5N1 15 µg
HN8 = H5N1 7.5 µg
HN4 = H5N1 3.8 µg
HN30AD = H5N1 30 µg + AS03
HN15AD = H5N1 15 µg + AS03
HN8AD = H5N1 7.5 µg + AS03
HN4AD = H5N1 3.8 µg + AS03
N = Number of subjects with available results
n/% = number/percentage of seropositive subjects (SN titer >=1:28)
95% CI = 95% confidence interval,
LL = Lower Limit,
UL = Upper Limit
GMT = Geometric Mean antibody Titer TABLE 17B-continued Seropositivity rates and GMTs (with 95% CI) for the neutralizing antibodies against the vaccine strain (Vietnam strain) at Day 0, Day 21 and Day 42 (ATP cohort for Immunogenicity)

| | | | | | | ≥28 1/DIL | | | GMT | | | |
|---|---|---|---|---|---|---|---|---|---|---|---|---|
| | | | | | | | 95% CI | | | 95% CI | | |
| Antibody | Group | Timing | N | n | % | LL | UL | value | LL | UL | Min | Max |

Min/Max = Minimum/Maximum
PRE = Pre-vaccination dose 1 (Day 0)
PI(D21) = 21 days after first vaccination (Day 21)
PII(D42) = 21 days after second vaccination (Day 42)

b) Seroconversion Rates for Neutralizing Antibody Titers Against H5N1 Vietnam in Study H5N1-007 (Table 18)

As mentioned above, a four fold increase is used to determine seroconversion against an influenza strain. Therefore, subjects seropositive at day 0 are only included if they achieved a fourfold increase, thereby subtracting a potential background.

b)1. Interim Data Obtained on a Limited Number of Subjects Per Groups

After the second dose, seroconversion in the non adjuvanted groups again could be observed in a dose dependent manner: 20.9, 37.5, 53.5 and 76.0% of subjects seroconverted in the 3.8, 7.5, 15 and 30 µg groups respectively. In the adjuvanted groups, 86.0, 83.3, 86.0 and 100.0% of subjects in the 3.8, 7.5, 15 and 30 µg groups respectively seroconverted, thereby also confirming the HI results. Of note, after the first dose of adjuvanted vaccine, already 66.7 to 88.0% of subjects had seroconverted in the four adjuvanted groups (Table 18A and FIG. 10B1).

TABLE 18A

Seroconversion rates (SC) for Neutralizing antibody titer (from Dresden) at each post-vaccination time point (ATP cohort for immunogenicity)

| | | | | | | SC | |
|---|---|---|---|---|---|---|---|
| | | | | | | | 95% CI |
| Strain | Timing | Group | N | n | % | LL | UL |
| FLU A/ | day 21 | HN30 | 25 | 19 | 76.0 | 54.9 | 90.6 |
| VIET/04 AB | | HN15 | 43 | 20 | 46.5 | 31.2 | 62.3 |
| | | HN8 | 40 | 9 | 22.5 | 10.8 | 38.5 |
| | | HN4 | 43 | 7 | 16.3 | 6.8 | 30.7 |
| | | HN30AD | 25 | 22 | 88.0 | 68.8 | 97.5 |
| | | HN15AD | 43 | 37 | 86.0 | 72.1 | 94.7 |
| | | HN8AD | 42 | 28 | 66.7 | 50.5 | 80.4 |
| | | HN4AD | 44 | 30 | 68.2 | 52.4 | 81.4 |
| | day 42 | HN30 | 25 | 19 | 76.0 | 54.9 | 90.6 |
| | | HN15 | 43 | 23 | 53.5 | 37.7 | 68.8 |
| | | HN8 | 40 | 15 | 37.5 | 22.7 | 54.2 |
| | | HN4 | 43 | 9 | 20.9 | 10.0 | 36.0 |
| | | HN30AD | 25 | 25 | 100.0 | 86.3 | 100.0 |
| | | HN15AD | 43 | 37 | 86.0 | 72.1 | 94.7 |
| | | HN8AD | 42 | 35 | 83.3 | 68.6 | 93.0 |
| | | HN4AD | 43 | 37 | 86.0 | 72.1 | 94.7 |

HN30 = H5N1 30 µg;
HN15 = H5N1 15 µg;
HN8 = H5N1 7.5 µg;
HN4 = H5N1 3.8 µg
HN30AD = H5N1 30 µg + AS03;
HN15AD = H5N1 15 µg + AS03;
HN8AD = H5N1 7.5 µg + AS03;
HN4AD = H5N1 3.8 µg + AS03
N = Number of subjects with available results TABLE 18A-continued Seroconversion rates (SC) for Neutralizing antibody titer (from Dresden) at each post-vaccination time point (ATP cohort for immunogenicity)

| | | | | | SC | |
|---|---|---|---|---|---|---|
| | | | | | | 95% CI |
| Strain | Timing | Group | N | n | % | LL | UL | n/% = Number/percentage of subjects who seroconverted (at least a 4-fold increase at POST)
95% CI = 95% confidence interval,
LL = Lower Limit,
UL = Upper Limit b)2. Data Obtained on the Total Cohort After the second dose, seroconversion in the non adjuvanted groups again could be observed in a dose dependent manner: 22.0, 36.7, 53.1 and 64.6.0% of subjects seroconverted in the 3.8, 7.5, 15 and 30 µg groups respectively. In the adjuvanted groups, 85.7, 86.0, 85.7 and 97.9% of subjects in the 3.8, 7.5, 15 and 30 µg groups respectively seroconverted, thereby also confirming the HI results. Of note, after the first dose of adjuvanted vaccine, already 66.0 to 83.7% of subjects had seroconverted in the four adjuvanted groups (Table 18B and FIG. 10B2).

TABLE 18B

Seroconversion rates (SC with 95% CI) for the neutralizing antibodies against the vaccine strain (Vietnam strain) at each post-vaccination time point (ATP cohort for Immunogenicity)

| | | | | | | SC with 95% CI | |
|---|---|---|---|---|---|---|---|
| Vaccine strain | Timing | Group | N | n | % | LL | UL |
| FLU A/VIET/04 | PI(D21) | HN30 | 49 | 28 | 57.1 | 42.2 | 71.2 |
| AB | | HN15 | 48 | 23 | 47.9 | 33.3 | 62.8 |
| | | HN8 | 49 | 11 | 22.4 | 11.8 | 36.6 |
| | | HN4 | 50 | 7 | 14.0 | 5.8 | 26.7 |
| | | HN30AD | 47 | 39 | 83.0 | 69.2 | 92.4 |
| | | HN15AD | 49 | 41 | 83.7 | 70.3 | 92.7 |
| | | HN8AD | 49 | 31 | 63.3 | 48.3 | 76.6 |
| | | HN4AD | 50 | 33 | 66.0 | 51.2 | 78.8 |
| | PII(D42) | HN30 | 48 | 31 | 64.6 | 49.5 | 77.8 |
| | | HN15 | 49 | 26 | 53.1 | 38.3 | 67.5 |
| | | HN8 | 49 | 18 | 36.7 | 23.4 | 51.7 |
| | | HN4 | 50 | 11 | 22.0 | 11.5 | 36.0 |
| | | HN30AD | 47 | 46 | 97.9 | 88.7 | 99.9 |
| | | HN15AD | 49 | 42 | 85.7 | 72.8 | 94.1 |
| | | HN8AD | 50 | 43 | 86.0 | 73.3 | 94.2 |
| | | HN4AD | 49 | 42 | 85.7 | 72.8 | 94.1 |

HN30 = H5N1 30 µg
HN15 = H5N1 15 µg
HN8 = H5N1 7.5 µg
HN4 = H5N1 3.8 µg

TABLE 18B-continued

Seroconversion rates (SC with 95% CI) for the neutralizing antibodies against the vaccine strain (Vietnam strain) at each post-vaccination time point (ATP cohort for Immunogenicity)

|  |  |  |  |  |  | SC with 95% CI | |
|---|---|---|---|---|---|---|---|
| Vaccine strain | Timing | Group | N | n | % | LL | UL |

HN30AD = H5N1 30 µg + AS03
HN15AD = H5N1 15 µg + AS03
HN8AD = H5N1 7.5 µg + AS03
HN4AD = H5N1 3.8 µg + AS03
N = Number of subjects with available results (ATP cohort for immunogenicity)
n/% = Number/percentage of subjects who seroconverted (at least a 4-fold increase at POST)
95% CI = 95% confidence interval,
LL = Lower Limit,
UL = Upper Limit The GMT titers and seroconversion rates for the Vietnam strain are illustrated in 18A and 18B respectively. Adjuvantation markedly improved in vitro neutralising antibody responses in the adjuvanted groups compared to the non-adjuvanted groups with 5 to 8 fold differences observed after the second dose for the three lower antigen levels. The adjuvant effect was also evident in the neutralising seroconversion rates and was most marked at the lower antigen levels after the second dose. In conclusion, neutralizing antibodies measured against the vaccine strain (Vietnam), support the results obtained by the HI. All adjuvanted groups including the lowest dose group of 3.8 µg achieved a seroconversion in over 65% after the first dose and over 80% of subjects (partial data) and over 85% of subjects (total data) tested after the second dose of the pandemic candidate vaccine. It is worth noting that post first dose, neutralization seroconversion rates were higher than those for HAI. The haemagglutination-inhibition results indicate the production of antibodies that specifically block the haemagglutinin receptor-binding site involved in attachment of the virus to the host cell. The neutralising results however confirm the production of biologically functional antibodies that can inhibit the complex process of virus attachment, entry and release from cells in tissue culture.

IV.7.1.4 Neutralizing Antibody Response to Heterologous Strain H5N1 A/Indonesia

As already discussed, due to the nature of the neutralization assay measuring antibodies that inhibit the penetration into the cell and propagation from cell to cell of the influenza virus in addition to the inhibition of the attachment of the virus, evaluating the drift strain allows to further assess the potential of the vaccine to prime also for a non-vaccine strain.

a) Geometric Mean Titres and Seropositivity Measured in Neutralization Assay Against H5N1 A/Indonesia in Study H5N1-007 (Table 19)

a)1. Partial Data with 3.8 µg and 7.5 µg HA Adjuvanted Groups Only

Partial data (of the 3.8 µg and 7.5 µg HA adjuvanted groups only) are presented herein below. In these two lowest adjuvanted groups, GMTs against the Indonesia strain achieved after two doses of the vaccine were 70.6 and 73.1 for the 3.8 µg and 7.5 µg adjuvanted group, respectively (Table 19A).

TABLE 19A

Seropositivity rates and GMTs of Neutralizing antibody titer for Indonesia strain at day 0, day 21 and day 42 (ATP cohort for immunogenicity)

| | | | | | | >=28 1/DIL | | | GMT | | | | |
|---|---|---|---|---|---|---|---|---|---|---|---|---|---|
| | | | | | | | 95% CI | | | 95% CI | | | |
| Antibody | Group | Timing | N | n | % | LL | UL | value | LL | UL | Min | Max |
| FLU A/IND/05 AB | HN8AD | PRE | 35 | 8 | 22.9 | 10.4 | 40.1 | 17.6 | 15.1 | 20.4 | <28.0 | 57.0 |
| | | PI(D21) | 35 | 27 | 77.1 | 59.9 | 89.6 | 47.5 | 35.3 | 64.0 | <28.0 | 284.0 |
| | | PII(D42) | 35 | 34 | 97.1 | 85.1 | 99.9 | 99.0 | 73.1 | 134.0 | <28.0 | 453.0 |
| | HN4AD | PRE | 38 | 4 | 10.5 | 2.9 | 24.8 | 16.3 | 13.9 | 19.1 | <28.0 | 113.0 |
| | | PI(D21) | 38 | 28 | 73.7 | 56.9 | 86.6 | 41.9 | 31.9 | 55.1 | <28.0 | 226.0 |
| | | PII(D42) | 38 | 34 | 89.5 | 75.2 | 97.1 | 93.1 | 70.6 | 122.7 | <28.0 | 284.0 |

HN8AD = H5N1 7.5 µg + AS03,
HN4AD = H5N1 3.8 µg + AS03
N = Number of subjects with available results
n/% = number/percentage of seropositive subjects (HI titer >=1:10)
95% CI = 95% confidence interval,
LL = Lower Limit,
UL = Upper Limit
GMT = Geometric Mean antibody Titer
Min/Max = Minimum/Maximum
PRE = Pre-vaccination dose 1 (Day 0),
PI(D21) = 21 days after first vaccination (Day 21),
PII(D42) = 21 days after second vaccination (Day 42)

a)2. Total Data with all Groups

In the adjuvanted groups, GMTs against the Indonesia strain achieved after two doses of the vaccine were 80.3, 95.7, 72.9 and 66.8 for the 3.8, 7.5, 15 and 30 µg adjuvanted groups respectively. GMTs in the non adjuvanted groups were lower with 14.5, 15.0, 16.5 and 20.6 in the 3.8, 7.5, 15 and 30 µg groups respectively (Table 19B and FIG. 10C).

TABLE 19B

Seropositivity rates and GMTs (with 95% CI) for the neutralizing
antibodies against the Indonesia strain at Day 0, Day 21 and Day 42
(ATP cohort for Immunogenicity)

| Antibody | Group | Timing | N | n | ≥28 1/DIL % | 95% CI LL | 95% CI UL | GMT value | 95% CI LL | 95% CI UL | Min | Max |
|---|---|---|---|---|---|---|---|---|---|---|---|---|
| FLU A/IND/05 AB | HN30 | PRE | 49 | 2 | 4.1 | 0.5 | 14.0 | 14.5 | 13.8 | 15.2 | <28.0 | 36.0 |
| | | PI(D21) | 48 | 20 | 41.7 | 27.6 | 56.8 | 24.9 | 20.0 | 30.8 | <28.0 | 142.0 |
| | | PII(D42) | 48 | 15 | 31.3 | 18.7 | 46.3 | 20.6 | 17.2 | 24.6 | <28.0 | 113.0 |
| | HN15 | PRE | 45 | 0 | 0.0 | 0.0 | 7.9 | 14.0 | 14.0 | 14.0 | <28.0 | <28.0 |
| | | PI(D21) | 43 | 6 | 14.0 | 5.3 | 27.9 | 16.9 | 14.2 | 20.2 | <28.0 | 226.0 |
| | | PII(D42) | 44 | 7 | 15.9 | 6.6 | 30.1 | 16.5 | 14.6 | 18.7 | <28.0 | 90.0 |
| | HN8 | PRE | 44 | 1 | 2.3 | 0.1 | 12.0 | 14.2 | 13.8 | 14.7 | <28.0 | 28.0 |
| | | PI(D21) | 43 | 5 | 11.6 | 3.9 | 25.1 | 15.4 | 14.2 | 16.8 | <28.0 | 45.0 |
| | | PII(D42) | 44 | 3 | 6.8 | 1.4 | 18.7 | 15.0 | 13.8 | 16.3 | <28.0 | 45.0 |
| | HN4 | PRE | 43 | 0 | 0.0 | 0.0 | 8.2 | 14.0 | 14.0 | 14.0 | <28.0 | <28.0 |
| | | PI(D21) | 43 | 1 | 2.3 | 0.1 | 12.3 | 14.5 | 13.5 | 15.4 | <28.0 | 57.0 |
| | | PII(D42) | 43 | 1 | 2.3 | 0.1 | 12.3 | 14.5 | 13.5 | 15.7 | <28.0 | 71.0 |
| | HN30AD | PRE | 47 | 0 | 0.0 | 0.0 | 7.5 | 14.0 | 14.0 | 14.0 | <28.0 | <28.0 |
| | | PI(D21) | 46 | 38 | 82.6 | 68.6 | 92.2 | 54.6 | 42.5 | 70.1 | <28.0 | 284.0 |
| | | PII(D42) | 46 | 42 | 91.3 | 79.2 | 97.6 | 66.8 | 53.4 | 83.5 | <28.0 | 226.0 |
| | HN15AD | PRE | 44 | 1 | 2.3 | 0.1 | 12.0 | 14.2 | 13.8 | 14.7 | <28.0 | 28.0 |
| | | PI(D21) | 44 | 35 | 79.5 | 64.7 | 90.2 | 38.1 | 30.0 | 48.5 | <28.0 | 287.0 |
| | | PII(D42) | 44 | 41 | 93.2 | 81.3 | 98.6 | 72.9 | 58.5 | 90.9 | <28.0 | 226.0 |
| | HN8AD | PRE | 47 | 10 | 21.3 | 10.7 | 35.7 | 17.3 | 15.2 | 19.5 | <28.0 | 57.0 |
| | | PI(D21) | 47 | 34 | 72.3 | 57.4 | 84.4 | 43.7 | 33.7 | 56.6 | <28.0 | 284.0 |
| | | PII(D42) | 46 | 45 | 97.8 | 88.5 | 99.9 | 95.7 | 75.3 | 121.7 | <28.0 | 453.0 |
| | HN4AD | PRE | 48 | 4 | 8.3 | 2.3 | 20.0 | 15.8 | 13.9 | 17.9 | <28.0 | 113.0 |
| | | PI(D21) | 48 | 32 | 66.7 | 51.6 | 79.6 | 36.6 | 28.8 | 46.5 | <28.0 | 226.0 |
| | | PII(D42) | 48 | 42 | 87.5 | 74.8 | 95.3 | 80.3 | 62.0 | 103.9 | <28.0 | 284.0 |

HN30 = H5N1 30 µg
HN15 = H5N1 15 µg
HN8 = H5N1 7.5 µg
HN4 = H5N1 3.8 µg
HN30AD = H5N1 30 µg + AS03
HN15AD = H5N1 15 µg + AS03
HN8AD = H5N1 7.5 µg + AS03
HN4AD = H5N1 3.8 µg + AS03
N = Number of subjects with available results
n/% = number/percentage of seropositive subjects (SN titer >=1:28)
95% CI = 95% confidence interval,
LL = Lower Limit,
UL = Upper Limit
GMT = Geometric Mean antibody Titer
Min/Max = Minimum/Maximum
PRE = Pre-vaccination dose 1 (Day 0)
PI(D21) = 21 days after first vaccination (Day 21)

b) Seroconversion Rates for Neutralizing Antibody Titers Against H5N1 A/Indonesia in Study H5N1-007 (Table 20)

b)1. Partial Data with 3.8 µg and 7.5 µg HA Adjuvanted Groups Only

Both the 3.8 and 7.5 µg adjuvanted groups received a high seroconversion rate against the antigenically different non-vaccination strain: 84.2% of subjects seroconverted when tested against the A/Indonesia strain (Table 20A).

TABLE 20A

Seroconversion rates (SC) of Neutralizing antibody titer for Indonesia
strain at each post-vaccination time point (ATP cohort for
immunogenicity)

| Strain | Timing | Vaccine Group | N | n | SC (4 fold) % | 95% CI LL | 95% CI UL |
|---|---|---|---|---|---|---|---|
| FLU A/IND/05 AB | PI(D21) | HN8AD | 35 | 13 | 37.1 | 21.5 | 55.1 |
| | | HN4AD | 38 | 15 | 39.5 | 24.0 | 56.6 |
| | PII(D42) | HN8AD | 35 | 22 | 62.9 | 44.9 | 78.5 |
| | | HN4AD | 38 | 32 | 84.2 | 68.7 | 94.0 |

HN8AD = H5N1 7.5 µg + AS03,
HN4AD = H5N1 3.8 µg + AS03
PRE = Pre-vaccination dose 1 (Day 0),
PI(D21) = 21 days after first vaccination (Day 21),
PII(D42) = 21 days after second vaccination (Day 42)
N = Number of subjects with available results
n/% = Number/percentage of subjects who seroconverted (at least a 4-fold increase at POST)
95% CI = 95% confidence interval,
LL = Lower Limit,
UL = Upper Limit These preliminary available data on the cross-reactivity in the neutralization assay indicate a remarkable effect of the adjuvanted vaccine containing a heterologous strain to the tested Indonesia strain and confirm the cross-reactive potential of the candidate vaccine.

b)2. Total Data with all Groups

Using neutralization assay to measure cross-reactive immunological response, results showed very high seroconversion rates at day 42, of 77.1% [62.7-88.0] and 67.4% [52.0-80.5] against the antigenically different Indonesia strain in the 3.8 µg and 7.5 µg HA adjuvanted vaccine group, respectively (see Table 20B). In the corresponding non-adjuvanted vaccine groups the seroconversion rates were <3%. Of note, seroconversion rates after the first does ranked for the adjuvanted groups between 27.3 and 54.3 against the Indonesia non-vaccine strain (Table 20B and FIG. 10D).

TABLE 20B

Seroconversion rates (SC with 95% CI) for the neutralizing antibodies against Indonesia strain at each post-vaccination time point (ATP cohort for immunogenicity)

| Strain | Timing | Vaccine Group | N | n | % | SC with 95% CI LL | UL |
|---|---|---|---|---|---|---|---|
| FLU A/IND/05 AB | PI(D21) | HN30 | 48 | 9 | 18.8 | 8.9 | 32.6 |
| | | HN15 | 43 | 2 | 4.7 | 0.6 | 15.8 |
| | | HN8 | 43 | 0 | 0.0 | 0.0 | 8.2 |
| | | HN4 | 43 | 1 | 2.3 | 0.1 | 12.3 |
| | | HN30AD | 46 | 25 | 54.3 | 39.0 | 69.1 |
| | | HN15AD | 44 | 12 | 27.3 | 15.0 | 42.8 |
| | | HN8AD | 47 | 17 | 36.2 | 22.7 | 51.5 |
| | | HN4AD | 48 | 15 | 31.3 | 18.7 | 46.3 |
| | PII(D42) | HN30 | 48 | 4 | 8.3 | 2.3 | 20.0 |
| | | HN15 | 44 | 1 | 2.3 | 0.1 | 12.0 |
| | | HN8 | 44 | 0 | 0.0 | 0.0 | 8.0 |
| | | HN4 | 43 | 1 | 2.3 | 0.1 | 12.3 |
| | | HN30AD | 46 | 29 | 63.0 | 47.5 | 76.8 |
| | | HN15AD | 44 | 30 | 68.2 | 52.4 | 81.4 |
| | | HN8AD | 46 | 31 | 67.4 | 52.0 | 80.5 |
| | | HN4AD | 48 | 37 | 77.1 | 62.7 | 88.0 |

HN30 = H5N1 30 µg
HN15 = H5N1 15 µg
HN8 = H5N1 7.5 µg
HN4 = H5N1 3.8 µg
HN30AD = H5N1 30 µg + AS03
HN15AD = H5N1 15 µg + AS03
HN8AD = H5N1 7.5 µg + AS03
HN4AD = H5N1 3.8 µg + AS03
PRE = Pre-vaccination dose 1 (Day 0)
PI(D21) = 21 days after first vaccination (Day 21)
PII(D42) = 21 days after second vaccination (Day 42)
N = Number of subjects with available results
n/% = Number/percentage of subjects who seroconverted (at least a 4-fold increase at POST)
95% CI = 95% confidence interval,
LL = Lower Limit,
UL = Upper Limit
Data source = Appendix table IIIA The data on the cross-reactivity in the neutralization assay indicate a remarkable effect of the adjuvanted vaccine containing a heterologous strain to the tested Indonesia strain and confirm the cross-reactive potential of the candidate vaccine at the lowest dose of 3.8 µg. The cross-clade neutralizing antibody responses observed infer that the AS03-adjuvanted vaccine could be deployed for a pre-pandemic immunisation.

IV.7.1.5 Cell Mediated Immunity (CMI)

For evaluation of CMI, please see sections I.2, I.3, and IV.3.2. One of the important features of an adjuvant in enhancing the immunogenicity of a vaccine is the ability to stimulate the cell mediated immunity, CMI. In this trial, an assessment of influenza specific CD4- and CD8-cells including frequencies of Th1 related cytokines as well as the evaluation of frequency of Memory B-cells was foreseen. Data are available for the T-cell responses of the two lowest antigen groups, adjuvanted or not with AS03.

CMI results are expressed as a frequency of cytokine(s)-positive CD4 T cells.

Median values (including first and third quartiles, see Table 21) are presented in FIG. 11. The results indicated that the adjuvanted groups clearly induced a much stronger CD4 response in comparison to the non-adjuvanted groups.

TABLE 21

Descriptive Statistics on the frequency-positive CD4 T-cells (per million CD4 T-cells) at each time point (ATP cohort for immunogenicity)

| Strain | Test Description | Vaccine Group | Timing | N | N miss. | GMT | Q1 | Median | Q3 | Max |
|---|---|---|---|---|---|---|---|---|---|---|
| H5N1 Vietnam | CD4- ALL DOUBLES | HN4 | Day 0 | 49 | 1 | 689.35 | 463.00 | 697.00 | 1120.00 | 2888.00 |
| | | | Day 21 | 48 | 2 | 1358.91 | 912.50 | 1432.50 | 1949.00 | 6690.00 |
| | | | Day 42 | 49 | 1 | 1522.31 | 1076.00 | 1647.00 | 2163.00 | 4809.00 |
| | | HN4AD | Day 0 | 49 | 1 | 801.27 | 620.00 | 878.00 | 1074.00 | 2217.00 |
| | | | Day 21 | 49 | 1 | 2667.58 | 2206.00 | 3051.00 | 4568.00 | 10945.00 |
| | | | Day 42 | 49 | 1 | 3093.61 | 2337.00 | 3046.00 | 4008.00 | 8879.00 |
| | | HN8 | Day 0 | 48 | 1 | 664.71 | 601.00 | 834.50 | 1257.50 | 2913.00 |
| | | | Day 21 | 46 | 3 | 1403.87 | 1078.00 | 1535.00 | 2017.00 | 2757.00 |
| | | | Day 42 | 49 | 0 | 1238.36 | 1062.00 | 1575.00 | 1906.00 | 2910.00 |
| | | HN8AD | Day 0 | 47 | 3 | 627.79 | 525.00 | 782.00 | 1093.00 | 3215.00 |
| | | | Day 21 | 49 | 1 | 3027.63 | 2304.00 | 3495.00 | 5178.00 | 11376.00 |
| | | | Day 42 | 48 | 2 | 3397.59 | 2511.00 | 3323.00 | 4923.00 | 9134.00 |
| | CD4- CD4OL | HN4 | Day 0 | 49 | 1 | 674.26 | 460.00 | 680.00 | 1120.00 | 2847.00 |
| | | | Day 21 | 48 | 2 | 1315.89 | 867.00 | 1365.00 | 1926.50 | 6691.00 |
| | | | Day 42 | 49 | 1 | 1481.49 | 1076.00 | 1582.00 | 2075.00 | 4684.00 |
| | | HN4AD | Day 0 | 49 | 1 | 771.85 | 594.00 | 815.00 | 1048.00 | 2102.00 |
| | | | Day 21 | 49 | 1 | 2576.31 | 2114.00 | 3010.00 | 4504.00 | 10503.00 |
| | | | Day 42 | 49 | 1 | 3005.85 | 2247.00 | 2940.00 | 3782.00 | 8535.00 |

TABLE 21-continued

Descriptive Statistics on the frequency-positive CD4 T-cells (per million CD4 T-cells) at each time point (ATP cohort for immunogenicity)

| Test Strain | Test Description | Vaccine Group | Timing | N | N miss. | GMT | Q1 | Median | Q3 | Max |
|---|---|---|---|---|---|---|---|---|---|---|
| | | HN8 | Day 0 | 48 | 1 | 656.81 | 530.00 | 799.00 | 1142.00 | 2813.00 |
| | | | Day 21 | 46 | 3 | 1362.22 | 1053.00 | 1531.50 | 1876.00 | 2757.00 |
| | | | Day 42 | 49 | 0 | 1189.79 | 1032.00 | 1466.00 | 1906.00 | 2792.00 |
| | | HN8AD | Day 0 | 47 | 3 | 615.32 | 512.00 | 775.00 | 1021.00 | 2951.00 |
| | | | Day 21 | 49 | 1 | 3001.77 | 2189.00 | 3371.00 | 4762.00 | 11124.00 |
| | | | Day 42 | 48 | 2 | 3295.38 | 2388.00 | 3167.50 | 4804.50 | 8690.00 |
| CD4-IFNG | | HN4 | Day 0 | 49 | 1 | 409.56 | 237.00 | 420.00 | 727.00 | 2560.00 |
| | | | Day 21 | 48 | 2 | 719.52 | 440.00 | 806.00 | 1097.50 | 3618.00 |
| | | | Day 42 | 49 | 1 | 758.46 | 563.00 | 715.00 | 1045.00 | 2402.00 |
| | | HN4AD | Day 0 | 49 | 1 | 476.45 | 333.00 | 584.00 | 778.00 | 1903.00 |
| | | | Day 21 | 49 | 1 | 1003.77 | 849.00 | 1240.00 | 1986.00 | 5743.00 |
| | | | Day 42 | 49 | 1 | 1321.30 | 929.00 | 1328.00 | 1672.00 | 3945.00 |
| | | HN8 | Day 0 | 48 | 1 | 462.73 | 322.00 | 509.50 | 979.50 | 2423.00 |
| | | | Day 21 | 46 | 3 | 694.95 | 580.00 | 849.50 | 1254.00 | 2104.00 |
| | | | Day 42 | 49 | 0 | 714.16 | 531.00 | 876.00 | 1079.00 | 2146.00 |
| | | HN8AD | Day 0 | 47 | 3 | 398.24 | 241.00 | 490.00 | 637.00 | 2531.00 |
| | | | Day 21 | 49 | 1 | 1406.88 | 980.00 | 1465.00 | 2587.00 | 6676.00 |
| | | | Day 42 | 48 | 2 | 1471.29 | 967.00 | 1417.50 | 2444.00 | 4763.00 |
| CD4-IL2 | | HN4 | Day 0 | 49 | 1 | 595.36 | 384.00 | 613.00 | 1049.00 | 2145.00 |
| | | | Day 21 | 48 | 2 | 1223.32 | 787.00 | 1276.00 | 1804.00 | 6000.00 |
| | | | Day 42 | 49 | 1 | 1370.12 | 1027.00 | 1479.00 | 2016.00 | 4233.00 |
| | | HN4AD | Day 0 | 49 | 1 | 686.60 | 501.00 | 770.00 | 965.00 | 1795.00 |
| | | | Day 21 | 49 | 1 | 2479.78 | 2082.00 | 2963.00 | 4348.00 | 10102.00 |
| | | | Day 42 | 49 | 1 | 2797.79 | 2062.00 | 2758.00 | 3617.00 | 8095.00 |
| | | HN8 | Day 0 | 48 | 1 | 611.24 | 515.50 | 744.00 | 1093.50 | 2638.00 |
| | | | Day 21 | 46 | 3 | 1225.92 | 1003.00 | 1374.00 | 1742.00 | 2606.00 |
| | | | Day 42 | 49 | 0 | 1099.43 | 942.00 | 1374.00 | 1706.00 | 2536.00 |
| | | HN8AD | Day 0 | 47 | 3 | 484.64 | 458.00 | 665.00 | 982.00 | 2588.00 |
| | | | Day 21 | 49 | 1 | 2591.08 | 2015.00 | 3205.00 | 4678.00 | 10746.00 |
| | | | Day 42 | 48 | 2 | 3056.63 | 2172.00 | 2981.50 | 4462.00 | 8662.00 |
| CD4-TNFA | | HN4 | Day 0 | 49 | 1 | 566.24 | 353.00 | 590.00 | 957.00 | 2270.00 |
| | | | Day 21 | 48 | 2 | 995.66 | 655.00 | 1089.00 | 1523.00 | 5373.00 |
| | | | Day 42 | 49 | 1 | 1039.47 | 733.00 | 1240.00 | 1532.00 | 3492.00 |
| | | HN4AD | Day 0 | 49 | 1 | 595.65 | 538.00 | 691.00 | 867.00 | 1760.00 |
| | | | Day 21 | 49 | 1 | 1703.32 | 1471.00 | 1859.00 | 3174.00 | 7577.00 |
| | | | Day 42 | 49 | 1 | 2286.39 | 1711.00 | 2222.00 | 2957.00 | 7650.00 |
| | | HN8 | Day 0 | 48 | 1 | 526.47 | 435.50 | 643.00 | 1036.50 | 2489.00 |
| | | | Day 21 | 46 | 3 | 1004.27 | 708.00 | 1120.50 | 1516.00 | 1976.00 |
| | | | Day 42 | 49 | 0 | 856.00 | 740.00 | 994.00 | 1363.00 | 2396.00 |
| | | HN8AD | Day 0 | 47 | 3 | 504.74 | 401.00 | 628.00 | 908.00 | 2892.00 |
| | | | Day 21 | 49 | 1 | 2099.73 | 1486.00 | 2373.00 | 3822.00 | 6886.00 |
| | | | Day 42 | 48 | 2 | 2442.38 | 1786.50 | 2400.50 | 3564.50 | 7629.00 |

HN8 = H5N1 7.5 μg
HN4 = H5N1 3.8 μg
HN8AD = H5N1 7.5 μg + AS03
HN4AD = H5N1 3.8 μg + AS03
N = number of subjects with available results;
N miss. = number of subjects with missing results
GM = Geometric Mean
SD = Standard Deviation
Q1, Q3 = First and third quartiles
MIN/MAX = Minimum/Maximum In the inferential analysis it was confirmed that both after the first vaccination at day 21 (with exception of IFN gamma positive CD4 cells) and after the second vaccination at day 42, the induction of cytokine positive CD 4 cells was significantly higher in the adjuvanted group in comparison to the non-adjuvanted group receiving the same dose. Therefore, the adjuvant effect seen in the serological evaluation of the antibodies induced by the vaccine was confirmed by the CMI results. In a similar fashion the analysis shows that the effect on CMI is clearly adjuvant-, but not dose-dependant (comparison of the 3.8 μg and the 7.5 μg doses only), which is consistent with the HI results (see Table 22).

TABLE 22

Inferential statistics (p-values from Kruskal-Wallis Tests) on the frequency cytokine-positive CD4 T-cells at each time point

| Groups compared | Test Description | P_value at Day 0 | P_value at Day 21 | P_value at Day 42 |
|---|---|---|---|---|
| *Adjuvant effect* | | | | |
| HN4 and HN4AD | CD4-ALL DOUBLES | 0.2150 | <0.0001 | <0.0001 |
| | CD4-CD4OL | 0.2190 | <0.0001 | <0.0001 |
| | CD4-IFNG | 0.1320 | 0.0012 | <0.0001 |
| | CD4-IL2 | 0.2497 | <0.0001 | <0.0001 |
| | CD4-TNFA | 0.3130 | <0.0001 | <0.0001 |
| HN8 and HN8AD | CD4-ALL DOUBLES | 0.4433 | <0.0001 | <0.0001 |
| | CD4-CD4OL | 0.4749 | <0.0001 | <0.0001 |
| | CD4-IFNG | 0.2771 | <0.0001 | <0.0001 |
| | CD4-IL2 | 0.3114 | <0.0001 | <0.0001 |
| | CD4-TNFA | 0.4657 | <0.0001 | <0.0001 |
| *Dose effect* | | | | |
| HN4 and HN8 | CD4-ALL DOUBLES | 0.2603 | 0.6774 | 0.3880 |
| | CD4-CD4OL | 0.2872 | 0.6941 | 0.3181 |
| | CD4-IFNG | 0.2054 | 0.3641 | 0.6366 |
| | CD4-IL2 | 0.2338 | 0.8264 | 0.2677 |
| | CD4-TNFA | 0.3538 | 0.9067 | 0.2137 |
| HN4AD and HN8AD | CD4-ALL DOUBLES | 0.4055 | 0.3958 | 0.2146 |
| | CD4-CD4OL | 0.4076 | 0.4366 | 0.2424 |
| | CD4-IFNG | 0.1498 | 0.1037 | 0.2146 |
| | CD4-IL2 | 0.3242 | 0.5673 | 0.2528 |
| | CD4-TNFA | 0.4703 | 0.3268 | 0.3787 |

HN8 = H5N1 7.5 µg
HN4 = H5N1 3.8 µg
HN8AD = H5N1 7.5 µg + AS03
HN4AD = H5N1 3.8 µg + AS03

In addition, the CMI response against pools of peptides covering H5 of A/Vietnam/1194/2004 and A/Indonesia/5/2005 was tested in the 3.8 µg and 7.5 µg adjuvanted and non-adjuvanted groups:

pool "Viet Total": covering the entire AA sequence of H5 (A/Vietnam/1194/2004)
pool "Viet-Indo Cons": covering all AA parts of sequences of H5 conserved between the 2 strains: A/Vietnam/1194/2004 and A/Indonesia/5/05
pool "Viet NC": covering all AA parts of sequences of H5 not conserved of A/Vietnam/1194/2004 (comparing with A/Indonesia/5/05)
pool "Indo NC": covering all AA part of sequences of H5 not conserved of A/Indonesia/5/05 (comparing with A/Vietnam/1194/2004)

Antigen specific CD4 and CD 8 T-cell responses are again expressed in 5 different tests:
-CD40L: cells producing at least CD40L and another cytokine (IFNγ, IL-2, TNFα)
-IL-2: cells producing at least IL-2 and another cytokine (CD40L, TNFα, IFNγ)
-TNFα: cells producing at least TNFα and another cytokine (CD40L, IL-2, IFNγ)
-IFNγ: cells producing at least IFNγ and another cytokine (IL-2, TNFα, CD40L)
-all doubles: cells producing at least two different cytokines (CD40L, IL-2, TNFα, IFNγ)

In summary, regarding the CD 4 T-cell response specific to H5 proteins, the H5-specific CD4 response was significantly higher in adjuvanted (7.5 µg and 3.8 µg) groups compared to non-adjuvanted groups. The H5-specific CD4 T cells express mainly CD40 ligand and IL-2, to a lower extend TNFα and a very low level of IFNγ. As expected was the specific response to H5 proteins (i.e. to the peptide pools used) lower than the response to H5N1 split antigen.

The cross reactivity evaluation of the CMI response to H5 Indonesia protein showed the following results:

a significant proportion (around 70%) of the H5 Vietnam-specific CD4 T-cell response recognized the conserved sequence between H5 Indonesia and H5 Vietnam, also a response to the non-conserved sequence between H5 Indo and H5 Vietnam was observed, but to a lower extend, interestingly, the magnitude of these responses recognizing the non-conserved sequences H5 Indonesia and the non conserved sequence H5 Vietnam looked similar Overall, the H5 specific CD4 T-cell response induced by the adjuvanted vaccine was strongest with the H5N1 Vietnam Split antigen, followed by the H5 Vietnam peptide pool (Viet-Total), the H5 Vietnam and Indonesia conserved (Viet-Indo Cons) and the H5 Vietnam and Indonesia non conserved (Viet NC and Indo NC, there was no difference between the last two).

TABLE 23

Descriptive Statistics on the frequency cytokine-positive CD4 T-cells (per million T-cells) for the pool "Viet-Indo Conserved" antigen at Day 0 and Day 42 (ATP cohort for immunogenicity)

| Test Antigen | Test description | Group | Timing | N | Nmiss | GM | Mean | SD | Min | Q1 | Median | Q3 | Max |
|---|---|---|---|---|---|---|---|---|---|---|---|---|---|
| POOL VIET-INDO CONS | CD4-ALL DOUBLES | HN8 | PRE | 43 | 6 | 10.89 | 64.19 | 102.02 | 1.00 | 1.00 | 26.00 | 76.00 | 460.00 |
| | | | PII(D42) | 44 | 5 | 131.98 | 194.50 | 118.61 | 1.00 | 116.50 | 179.50 | 278.00 | 433.00 |
| | | HN4 | PRE | 43 | 7 | 29.99 | 85.00 | 84.77 | 1.00 | 5.00 | 77.00 | 113.00 | 326.00 |
| | | | PII(D42) | 44 | 6 | 110.39 | 206.64 | 181.99 | 1.00 | 88.50 | 149.50 | 266.00 | 724.00 |
| | | HN8AD | PRE | 43 | 7 | 40.25 | 121.42 | 136.84 | 1.00 | 15.00 | 92.00 | 184.00 | 750.00 |
| | | | PII(D42) | 43 | 7 | 323.19 | 537.63 | 446.13 | 1.00 | 227.00 | 434.00 | 717.00 | 2408.00 |
| | | HN4AD | PRE | 42 | 8 | 16.26 | 151.31 | 348.68 | 1.00 | 1.00 | 27.00 | 165.00 | 2163.00 |
| | | | PII(D42) | 44 | 6 | 350.50 | 527.14 | 407.58 | 1.00 | 220.00 | 426.00 | 666.50 | 1891.00 |
| | CD4-CD4OL | HN8 | PRE | 43 | 6 | 10.43 | 58.47 | 94.73 | 1.00 | 1.00 | 22.00 | 73.00 | 460.00 |
| | | | PII(D42) | 44 | 5 | 115.41 | 186.39 | 119.66 | 1.00 | 93.50 | 166.50 | 282.00 | 456.00 |
| | | HN4 | PRE | 43 | 7 | 33.34 | 82.84 | 81.68 | 1.00 | 23.00 | 59.00 | 120.00 | 300.00 |
| | | | PII(D42) | 44 | 6 | 95.93 | 201.57 | 176.68 | 1.00 | 86.00 | 138.50 | 286.50 | 689.00 |
| | | HN8AD | PRE | 43 | 7 | 37.09 | 114.14 | 134.05 | 1.00 | 18.00 | 92.00 | 166.00 | 778.00 |
| | | | PII(D42) | 43 | 7 | 307.01 | 509.12 | 432.32 | 1.00 | 238.00 | 377.00 | 672.00 | 2350.00 |
| | | HN4AD | PRE | 42 | 8 | 19.78 | 139.95 | 301.66 | 1.00 | 1.00 | 40.50 | 133.00 | 1864.00 |
| | | | PII(D42) | 44 | 6 | 332.42 | 508.50 | 396.32 | 1.00 | 215.50 | 424.00 | 642.50 | 1891.00 |
| | CD4-IFN-γ | HN8 | PRE | 43 | 6 | 5.13 | 23.56 | 36.07 | 1.00 | 1.00 | 1.00 | 37.00 | 148.00 |
| | | | PII(D42) | 44 | 5 | 23.07 | 65.30 | 70.44 | 1.00 | 3.50 | 52.50 | 98.00 | 349.00 |
| | | HN4 | PRE | 43 | 7 | 14.87 | 48.51 | 67.28 | 1.00 | 1.00 | 34.00 | 54.00 | 384.00 |
| | | | PII(D42) | 44 | 6 | 17.74 | 52.55 | 53.47 | 1.00 | 1.00 | 37.00 | 80.00 | 197.00 |
| | | HN8AD | PRE | 43 | 7 | 10.90 | 36.74 | 43.71 | 1.00 | 1.00 | 24.00 | 54.00 | 169.00 |
| | | | PII(D42) | 43 | 7 | 68.02 | 142.05 | 217.10 | 1.00 | 40.00 | 70.00 | 218.00 | 1388.00 |
| | | HN4AD | PRE | 42 | 8 | 7.42 | 64.48 | 134.51 | 1.00 | 1.00 | 1.00 | 62.00 | 697.00 |
| | | | PII(D42) | 44 | 6 | 50.81 | 105.84 | 116.34 | 1.00 | 33.50 | 62.50 | 149.00 | 660.00 |
| | CD4-IL2 | HN8 | PRE | 43 | 6 | 10.05 | 59.26 | 93.00 | 1.00 | 1.00 | 21.00 | 88.00 | 459.00 |
| | | | PII(D42) | 44 | 5 | 85.32 | 147.82 | 99.74 | 1.00 | 77.00 | 141.50 | 228.50 | 434.00 |
| | | HN4 | PRE | 43 | 7 | 24.98 | 74.88 | 80.87 | 1.00 | 3.00 | 50.00 | 122.00 | 272.00 |
| | | | PII(D42) | 44 | 6 | 99.53 | 186.34 | 169.03 | 1.00 | 89.00 | 142.00 | 222.00 | 752.00 |
| | | HN8AD | PRE | 43 | 7 | 24.32 | 85.09 | 84.59 | 1.00 | 1.00 | 62.00 | 153.00 | 279.00 |
| | | | PII(D42) | 43 | 7 | 330.45 | 467.56 | 375.07 | 27.00 | 175.00 | 373.00 | 656.00 | 1743.00 |
| | | HN4AD | PRE | 42 | 8 | 17.88 | 118.31 | 253.10 | 1.00 | 1.00 | 41.50 | 132.00 | 1565.00 |
| | | | PII(D42) | 44 | 6 | 277.78 | 456.34 | 378.28 | 1.00 | 180.00 | 371.00 | 616.50 | 1888.00 |
| | CD4-TNFA | HN8 | PRE | 43 | 6 | 10.10 | 52.05 | 74.44 | 1.00 | 1.00 | 16.00 | 76.00 | 293.00 |
| | | | PII(D42) | 44 | 5 | 65.28 | 128.70 | 97.03 | 1.00 | 34.00 | 131.50 | 211.50 | 369.00 |
| | | HN4 | PRE | 43 | 7 | 12.12 | 58.30 | 80.40 | 1.00 | 1.00 | 25.00 | 102.00 | 309.00 |
| | | | PII(D42) | 44 | 6 | 44.84 | 129.00 | 116.24 | 1.00 | 29.00 | 111.00 | 228.00 | 392.00 |
| | | HN8AD | PRE | 43 | 7 | 39.83 | 98.26 | 136.53 | 1.00 | 25.00 | 60.00 | 129.00 | 806.00 |
| | | | PII(D42) | 43 | 7 | 193.36 | 364.91 | 299.01 | 1.00 | 121.00 | 309.00 | 555.00 | 1409.00 |
| | | HN4AD | PRE | 42 | 8 | 14.77 | 124.02 | 304.56 | 1.00 | 1.00 | 21.00 | 106.00 | 1897.00 |
| | | | PII(D42) | 44 | 6 | 243.66 | 351.84 | 268.81 | 1.00 | 154.50 | 285.00 | 429.50 | 1176.00 |

HN8 = H5N1 7.5 μg
HN4 = H5N1 3.8 μg
HN8AD = H5N1 7.5 μg + AS03
HN4AD = H5N1 3.8 μg + AS03
N = number of subjects with available results
Nmiss = number of subjects with missing results
GM = Geometric Mean
SD = Standard Deviation
Q1, Q3 = First and third quartiles
Min/Max = Minimum/Maximum

TABLE 24

Inferential statistics on the frequency cytokine-positive CD4 T-cells for the pool "Viet-Indo Conserved" antigen at Day 0 and Day 42 (ATP cohort for immunogenicity)

| Groups compared | Test description | P-value PRE | P-value PII(D 42) |
|---|---|---|---|
| Dose effect | | | |
| HN8 and HN4 | CD4-ALL DOUBLES | 0.0313 | 0.6462 |
| | CD4-CD4OL | 0.0142 | 0.7606 |
| | CD4-IFN-γ | 0.0114 | 0.4762 |
| | CD4-IL2 | 0.0618 | 0.6432 |
| | CD4-TNFA | 0.7373 | 0.8053 |
| HN8AD and HN4AD | CD4-ALL DOUBLES | 0.1621 | 0.9155 |
| | CD4-CD4OL | 0.2901 | 0.8886 |
| | CD4-IFN-γ | 0.4640 | 0.3591 |
| | CD4-IL2 | 0.5114 | 0.9020 |
| | CD4-TNFA | 0.1023 | 0.8618 |
| Adjuvant effect | | | |
| HN8AD and HN8 | CD4-ALL DOUBLES | 0.0057 | <0.0001 |
| | CD4-CD4OL | 0.0041 | <0.0001 |
| | CD4-IFN-γ | 0.0672 | 0.0086 |

TABLE 24-continued

Inferential statistics on the frequency cytokine-positive
CD4 T-cells for the pool "Viet-Indo Conserved"
antigen at Day 0 and Day 42 (ATP cohort for immunogenicity)

| Groups compared | Test description | P-value PRE | P-value PII(D 42) |
|---|---|---|---|
| HN4AD and HN4 | CD4-IL2 | 0.0432 | <0.0001 |
| | CD4-TNFA | 0.0085 | <0.0001 |
| | CD4-ALL DOUBLES | 0.4136 | <0.0001 |
| | CD4-CD40L | 0.6009 | <0.0001 |
| | CD4-IFN-γ | 0.1774 | 0.0083 |

TABLE 24-continued

Inferential statistics on the frequency cytokine-positive
CD4 T-cells for the pool "Viet-Indo Conserved"
antigen at Day 0 and Day 42 (ATP cohort for immunogenicity)

| Groups compared | Test description | P-value PRE | P-value PII(D 42) |
|---|---|---|---|
| | CD4-IL2 | 0.6957 | <0.0001 |
| | CD4-TNFA | 0.7129 | <0.0001 |

HN8 = H5N1 7.5 µg
HN4 = H5N1 3.8 µg
HN8AD = H5N1 7.5 µg + AS03
HN4AD = H5N1 3.8 µg + AS03
P-value = Kruskal-Wallis Test In conclusion, AS03 in combination with the potential pandemic strain A/Vietnam was able to stimulate a cell mediated immune response with the two lowest antigen doses tested. In addition, the response observed in the adjuvanted groups was stronger than the CD4 response induced by the non-adjuvanted groups. Moreover, the adjuvanted groups with the lowest antigen content showed a higher response also against the antigenically different Indonesia strains (conserved peptide sequence): with the exception of IFNγ, a significant higher response in comparison to the non-adjuvanted group could be shown. The results obtained for the cell-mediated immune response therefore confirm the results of the serology with responses elicited against the vaccine strain and the antigenically different non-vaccine strain by the adjuvanted vaccine.

IV.7.1.6 Influenza Specific B Cell Memory

Influenza specific memory B cells (Antigen: H5N1 A/Vietnam/1194/2004) were measured in the two lowest dose groups with and without AS03 adjuvant. Results (Tables 25 and 26) have been expressed as a frequency of Flu-specific memory B cells within a million of memory B cells.

In summary, pre-vaccination frequencies of influenza-specific B cell memory were present at a similar level in the four groups (3.8 and 7.5 µg with and without AS03). The induction of influenza-specific B cell memory responses was significantly higher in adjuvanted groups. No antigen-dose effect was detected on the CMI response in terms of influenza-specific B cell memory.

TABLE 25

Descriptive Statistics on the frequency of memory B cell specific to
H5N1 antigen (per million memory B Cells) against vaccine strain
(A/Vietnam) (ATP cohort for immunogenicity)

| Group | Timing | N | N miss | GM | Mean | SD | Min | Q1 | Median | Q3 | Max |
|---|---|---|---|---|---|---|---|---|---|---|---|
| HN8 | PRE | 36 | 13 | 1451.45 | 2118.67 | 1660.59 | 101.00 | 779.00 | 1656.50 | 3058.00 | 5672.00 |
| | PII(D42) | 38 | 11 | 3652.78 | 4549.21 | 2933.64 | 660.00 | 2185.00 | 4144.50 | 5741.00 | 11463.00 |
| HN4 | PRE | 41 | 9 | 1441.16 | 2634.88 | 2944.67 | 71.00 | 730.00 | 1566.00 | 3179.00 | 14835.00 |
| | PII(D42) | 40 | 10 | 2981.20 | 4164.95 | 2973.37 | 142.00 | 1983.50 | 3523.00 | 5446.50 | 11390.00 |
| HN8AD | PRE | 39 | 11 | 1732.49 | 2670.28 | 2163.99 | 56.00 | 1084.00 | 2146.00 | 4101.00 | 9696.00 |
| | PII(D42) | 37 | 13 | 6557.32 | 8124.30 | 5777.05 | 1087.00 | 4962.00 | 6698.00 | 9776.00 | 30346.00 |
| HN4AD | PRE | 38 | 12 | 2166.36 | 3193.68 | 2832.49 | 405.00 | 1186.00 | 2270.50 | 4223.00 | 12147.00 |
| | PII(D42) | 36 | 14 | 7639.18 | 9696.64 | 6018.86 | 469.00 | 5177.00 | 8765.00 | 12955.50 | 24092.00 |

HN8 = H5N1 7.5 µg
HN4 = H5N1 3.8 µg
HN8AD = H5N1 7.5 µg + AS03
HN4AD = H5N1 3.8 µg + AS03
N = number of subjects with available results
N miss = number of subjects with missing results
GM = Geometric Mean
SD = Standard Deviation
Q1, Q3 = First and third quartiles
Min/Max = Minimum/Maximum

TABLE 26

Inferential statistics on the individual difference between the
post-vaccination (Day 42) and PRE (Day 0) of frequency of memory
B cell specific to H5N1 antigen (per million memory B Cells) against
vaccine strain (A/Vietnam) (ATP cohort for immunogenicity)

| Groups compared | P-value PII(D 42)-PRE |
|---|---|
| Dose effect | |
| HN8 and HN4 | 0.3255 |
| HN8AD and HN4AD | 0.4470 |
| Adjuvant effect | |
| HN8AD and HN8 | 0.0105 |
| HN4AD and HN4 | 0.0001 |

HN8 = H5N1 7.5 µg
HN4 = H5N1 3.8 µg
HN8AD = H5N1 7.5 µg + AS03
HN4AD = H5N1 3.8 µg + AS03
P-value = Kruskal-Wallis Test

IV.8. Overall Conclusions

IV.8.1. Reactogenicity and Safety Results

The leading candidate for the next influenza pandemic is the avian virus H5N1, which has resulted in a high mortality rate in cases of bird-to-human transmission, although efficient human-to-human transmission has not been fully confirmed. Should H5N1 demonstrate the ability to spread efficiently from person to person combined with the global transport network, the outcome may feasibly be a widespread influenza outbreak affecting a high percentage of individuals, leading to increased mortality and morbidity in all countries.

Therefore, an immunologically effective and antigen sparing approach to vaccination has to be established to prevent potentially devastating effects of a pandemic. This can be achieved by using a suitable adjuvant, and for the first time, the immunogenicity enhancing effect of a novel adjuvant on a H5N1 candidate vaccine could be shown in this trial.

This study was designed to evaluate (1) the safety and reactogenicity in healthy adults of an pandemic influenza candidate vaccine adjuvanted or not with oil in water emulsion, i.e. AS03, (2) the antibody and cell-mediated immune responses.

Reactogenicity data show that the adjuvanted pandemic candidate vaccine induced (independent from antigen content) more local and general symptoms than the non-adjuvanted groups. However, the safety profile of all 4 adjuvanted groups was clinically acceptable. No serious adverse event was reported.

From these results, it can be concluded that the reactogenicity and safety profile of the pandemic candidate vaccine adjuvanted with AS03 is satisfactory and clinically acceptable.

IV.8.2. Immunogenicity Results

Regarding the immune response, the pandemic influenza candidate vaccine adjuvanted with AS03 exceeded with all antigen contents tested (3.8 μg, 7.5 μg, 15 μg and 30 μg HA, H5N1 A/Vietnam/1194/2004) the requirements of the European authorities for annual registration of split virion influenza vaccines ("Note for Guidance on Harmonisation of Requirements for influenza Vaccines" for the immunological assessment of the annual strain changes—CPMP/BWP/214/96) together with the "Guideline on dossier structure and content for pandemic influenza marketing authorization application, CPMP/VEG/4717/03", currently used as basis for evaluation of pandemic candidate influenza vaccines.

The four different antigen contents for a adjuvanted pandemic influenza candidate vaccine tested in this trial were immunogenic in the healthy adults, who developed a excellent antibody response to influenza haemagglutinin as measured by HI (Table 27).

candidate could be confirmed. Finally, CMI data collected are also in line with the serological results for response against the homologous and the heterologous starin tested.

In summary, 2 doses of the adjuvanted pandemic influenza candidate vaccine induce at the lowest tested dose of 3.8 μg HA a protective titer against the vaccine strain H5N1 A/Vietnam/1194/2004 in a very high proportion of subjects, markedly exceeding all FDA and EU licensure criteria established for evaluation of immunogenicity of influenza vaccines, against the homologous Vietnam strain. Furthermore, more than 75% of subjects receiving the lowest dose of the adjuvanted vaccine seroconverted for neutralizing antibodies against a drifted H5N1 isolate (H5N1-A/Indonesia/5/2005-clade 2), documenting the ability of the candidate pre-pandemic vaccine to induce immunity against a drift strain.

The results support the use of the described vaccine composition even at as low a dose as 3.8 μg HA, to achieve seroprotection in a pandemic situation in which the pre-pandemic priming is performed with a vaccine comprising a strain heterologous to the circulating pandemic strain. In other words, the described composition can be used to prime for subsequent responses to drifted pandemic strain(s). The results are supportive of the use of the claimed composition in a heterologous and homologous 1- and 2-dose prime-boost use of pandemic monovalent (H5N1) influenza vaccine adjuvanted with AS03:

priming of patients with one or two doses of the adjuvanted vaccine containing one pandemic strain (e.g. the Vietnam strain), at a selected dose, including a low HA amount, followed several months later (e.g. 6 or 12 months later) by one dose of i) either the same pandemic strain (e.g. Vietnam strain, i.e. homologous prime-boost) or ii) an heterologous (e.g. Indonesia strain, i.e. heterologous prime-boost) strain, given as a boost.

The adjuvanted vaccine was shown to provide a substantial level of immune protection against different strains of H5N1, and this strong cross-immunity was shown to develop rapidly—just 6 weeks after the first vaccine shot (two shots given 3 weeks apart). The value of this adjuvanted vaccine will importantly lie in a situation in which pandemic is declared after individuals have been primed prior to or around pandemic onset once or twice with either the same strain or a strain different to the 'pandemic' strain.

TABLE 27

| Variable | EU standard for antibody response | HN30AD | HN15AD | HN7.5AD | HN3.8AD |
|---|---|---|---|---|---|
| Conversion factor | >2.5 | 27.9 | 38.1 | 60.5 | 36.4 |
| Seroconversion rate (%) | >40% | 85.4 | 95.9 | 90.0 | 82.0 |
| Protection rate (%) | >70% | 84.0 | 90.0 | 95.9 | 85.4 |

HN30AD = H5N1 30 μg + AS03
HN15AD = H5N1 15 μg + AS03
HN8AD = H5N1 7.5 μg + AS03
HN4AD = H5N1 3.8 μg + AS03

Data evaluating the cross reactivity towards an antigenically different strain, H5N1 A/Indnesia/5/05, with the Haemagglutinin inhibition assay indicating in addition a cross-priming of the vaccinees in the adjuvanted groups against a drifted strain. Serological measures were completed by evaluation using the neutralizing assay for homologous and heterologous strain. Also by neutralization assay the immunogenicity and the cross-protective potential of the vaccine Furthermore this pandemic or pre-pandemic vaccine has achieved a strong neutralizing antibody immune response 25 times greater than observed with a non-adjuvanted vaccine, and this response was achieved with 12 times less antigen than is required for a regular seasonal flu vaccine, validating its antigen-sparing effect: a low-dose vaccine means greater production capacity now, making more vaccine available for stockpile and/or priming; and cross-protection in the vaccine means early vaccination (priming) of some priority groups could enhance overall preparedness.

Example V—Pre-Clinical Evaluation of Adjuvanted and Unadjuvanted Split Influenza Vaccines (Comprising H5N1 Strain) in C57Bl/6 Naive Mice V.1. Experimental Design and Objective This study investigated the humoral and cellular immune responses induced by H5N1 Split vaccines adjuvanted with AS03 in naïve mice. The objective of this experiment was to demonstrate the added value of the adjuvantation in order to increase the immunogenicity of an adjuvanted influenza vaccine compared to naïve mice immunized with PBS or the unadajuvanted H5N1 Split vaccines.

V.2. Treatment/Group and Vaccine Formulations

C57Bl/6 mice received two (28 days interval) administrations of different doses (3, 1.5, 0.75, 0.38 µg) of A/Vietnam/1194/2004 split vaccine adjuvanted with AS03. Immune responses were compared to the administration of two doses of the unadjuvanted split H5N1 vaccine (3 µg). Sera were collected 21 days post-boost to evaluate the humoral response by ELISA and HI assay.

Groups of 10 mice per group (dose/mice) for the assessment of humoral response:
  H5N1 Split AS03 (3 µg)
  H5N1 Split AS03 (1.5 µg)
  H5N1 Split AS03 (0.75 µg)
  H5N1 Split AS03 (0.38 µg)
  H5N1 Split Plain (3 µg)
  PBS V.2.1. Preparation of the Vaccine Formulations V.2.1.1. Split H5N1 Adjuvanted with the Oil-in-Water Emulsion Adjuvant ASO3A in a 1000 µl Dose.

Split H5N1 clinical batches at 60 µg/ml-30 µg/ml-15 µg/ml-7.5 µg/ml are mixed vol/vol with ASO3A adjuvant (prepared as taught in Example 2). Injections occur within the hour following the end of the formulation.

V.2.1.2. Unadjuvanted Split H5N1 in a 1000 µl Dose (Plain).

Tween 80, Triton X100 and Thiomersal are added to the Final Bulk Buffer (PBS pH 7.2±0.3 prepared as taught in Example 3) in order to reach a final concentration of 230 µg/ml for Tween 80, 10 µg/ml for Thiomersal (the added quantities taking into account their respective concentration in the influenza preparation) and 35 µg/ml for Triton X100. After 5 min stirring, 30 µg of H5N1 strain (HA antigen) are added. The formulation is stirred for 30 minutes at room temperature. Injections occur within the hour following the end of the formulation.

V.2.2. Read-Outs
  Anti-H5N1 IgG antibody titers at day 49, by ELISA
  HI titers at day 49 by the Hemagglutination inhibition assay
  CD4+ T cell responses at day 35 (7 days post-immunizations)

V.3. Results and Conclusions

V.3.1. Humoral Responses (Anti-H5N1 ELISA Titers).

As shown in FIG. 12, AS03-adjuvanted H5N1 split vaccines induced significantly higher anti-H5N1 IgG antibody responses compared to mice immunized with PBS or the unadjuvanted H5N1 vaccine (p value <0.00001) (GMT with [95% CI]=30,444 [7,461; 5,992] with 0.38 µg split adjuvanted H5N1 vaccine versus 49 [73; 29] for the 3 µg of unadjuvanted split H5N1 one). No antigen dose response effect was observed between mice immunized with different doses of AS03-adjuvanted H5N1 vaccines (p value >0.5).

V.3.2. Humoral Responses (HI Titers)

As shown in FIG. 13, AS03-adjuvanted H5N1 split vaccines induced significantly higher anti-H5N1 HI titers to the homologous strain compared to mice immunized with the unadjuvanted H5N1 vaccine (GMT with [95% CI]=1,810 [541; 416] with 0.38 µg adjuvanted split H5N1 vaccine versus 11 [10; 5] for the 3 µg unadjuvanted split H5N1 one). No antigen dose response effect was observed between mice immunized with different doses of AS03-adjuvanted H5N1 split vaccines. Nevertheless, a trend for lower anti-H5N1 HI titers (2-fold reduction) was observed between the highest antigen dose (3 µg) (GMT with [95% CI]=3,620 [5,938; 2,249]) and the lowest dose (0.38 µg) (GMT with [95% CI]=1,810 [541; 415]).

V.3.3. Cellular Immune Response (CD4+ T Cell Response).

As shown in FIG. 16, a clear difference was observed between CD4+ T cell responses induced by non-adjuvanted H5N1 vaccine and adjuvanted H5N1 vaccines for both doses of antigen (1.5 or 0.38 µg). No antigen dose response effect was observed between mice immunized with two different doses of adjuvanted H5N1 vaccines (1.5 or 0.38 µg).

In summary, immunogenicity studies in mice showed that AS03-adjuvanted H5N1 split vaccine induced significantly higher humoral (anti-H5N1 IgG and HI titers) and cellular (CD4+ T cell) responses compared to mice immunized with PBS or the unadjuvanted H5N1 split vaccine. Thus for humoral immune responses AS03 adjuvant clearly enhances vaccine immunogenicity. No antigen dose response effect was observed for humoral or cellular responses between mice immunized with 3 µg to 0.38 µg HA of AS03 adjuvanted H5N1 split vaccine. These data suggest that even lower doses of HA than evaluated here may be required to observe a dose response effect in this model. This finding further illustrates the potent adjuvant activity of AS03 in this vaccine formulation and supports antigen-sparing strategies and increased vaccine supply, in particular in a naïve population that may require 2 vaccine doses for protection.

Example VI—Pre-Clinical Evaluation of an Adjuvanted Pandemic Split Influenza Vaccines (Comprising H5N1 Strain) after Heterologous Challenge in Ferrets VI.1. Rationale and Objectives This study investigated the efficacy of H5N1 Split vaccines (A/Vietnam/1194/2004) adjuvanted with AS03 to protect ferrets against a lethal challenge with the H5N1 heterologous strain A/Indonesia/5/2005. The objective of this experiment was to demonstrate the efficacy of an adjuvanted influenza vaccine compared to ferrets immunized with PBS or the adjuvant alone.

VI.2. Experimental Design

VI.2.1. Treatment/Group (Table 28)

Four groups of ferrets (n=6) (*Mustela putorius furo*) were immunized intramuscularly with four different concentrations of A/Vietnam/1194/04 (Clade 1, NIBRG-14) (15, 7.5, 3.8 and 1.7 µg) vaccine in combination with AS03 (standard HD, 250 µl/dose). Two control groups consisted of ferrets immunized with either AS03 alone or the unadjuvanted A/Vietnam vaccine (15 µg). Ferrets were vaccinated on days 0 and 21. Sera were collected on day 21 and 42 for analysis of serological responses. Neutralizing antibody titres to homologous (A/Vietnam/1194/04) or heterologous (A/Indonesia/5/05) virus were determined by neutralization assay. Ferrets were then challenged on day 49 with a dose of $10^5$ $TCID_{50}$ (50% Tissue Culture Infective Dose) of A/Indonesia/5/05 (Clade 2). Lung tissues were collected after the challenge to assess virus shedding by virus titration culture on MDCK cells. Data were expressed as $TCID_{50}$ per gram of lung tissue. On day 54, all surviving animals were euthanized.

TABLE 28

| Group | Antigen +/− adjuvant | Dosage | Route/ schedule | Other treatment |
|---|---|---|---|---|
| 1 | AS03 alone | | IM Days 0 and 21 | Challenge H5N1 (A/Indonesia/5/05) Day 49 |
| 2 | H5N1 Plain | 15 μg HA | IM Days 0 and 21 | Challenge H5N1 (A/Indonesia/5/05) Day 49 |
| 3 | H5N1 AS03 | 15 μg HA | IM Days 0 and 21 | Challenge H5N1 (A/Indonesia/5/05) Day 49 |
| 4 | H5N1 AS03 | 7.5 μg HA | IM Days 0 and 21 | Challenge H5N1 (A/Indonesia/5/05) Day 49 |
| 5 | H5N1 AS03 | 3.8 μg HA | IM Days 0 and 21 | Challenge H5N1 (A/Indonesia/5/05) Day 49 |
| 6 | H5N1 AS03 | 1.7 μg HA | IM Days 0 and 21 | Challenge H5N1 (A/Indonesia/5/05) Day 49 |

VI.2.2. Preparation of the Vaccine Formulations

VI.2.2.1. Split H5N1 Adjuvanted with the Oil-in-Water Emulsion Adjuvant ASO3A in a 500 μl Dose A premixed buffer is previously prepared in the Final Bulk Buffer (PBS pH 7.2±0.3, prepared as taught in Example 3) containing Thiomersal, Tween 80 and Triton X100. Thiomersal and Tween 80 are added in quantities taking into account their concentrations in the strain. The final concentration of Thiomersal is 10 μg/ml. Detergent are at a HA/detergent ratio of 0.13 for Tween 80 and 0.86 for Triton X100.

The day of the immunizations 15-7.5-3.8 or 1.7 μg of HA (H5N1 strain) are added to the premixed buffer. After 30 minutes stirring, 250 μl of SB62 emulsion (prepared as taught in Example 2) is added. The formulation is stirred for 30 minutes. Injections occur within the hour following the end of the formulation.

VI.2.2.2. Unadjuvanted Split H5N1 in a 500 μl Dose (Plain)

A premixed buffer is previously prepared in the Final Bulk Buffer containing Thiomersal, Tween 80 and Triton X100 in order to reach a final concentration of 230 μg/ml for Tween 80, 35 μg/ml for Triton X 100 and 10 μg/ml for Thiomersal. The added quantities take into account their concentrations in the strain. The day of the immunizations 15 μg of H5N1 strain (HA antigen) are added to the premixed buffer. The formulation is stirred for 30 minutes. Injections occur within the hour following the end of the formulation.

VI.2.3. Read-Out

Protection at D+5 Post challenge as measured by % protection (number of ferrets alive/total number ferrets per group) (Table 29)

TABLE 29

| | Read-outs | |
|---|---|---|
| Readout | Timepoint | Analysis method |
| Protection | D + 5 Post challenge | % protection (number of ferrets alive/total number ferrets per group) |

TABLE 29-continued

| | Read-outs | |
|---|---|---|
| Readout | Timepoint | Analysis method |
| Neutralizing antibody titers | Days 21 and 42 | Neutralization assay |
| Viral shedding | Day 49 to Day 54 | Virus titration culture on MDCK on lung tissue and throat/nasal swabs |

VI.3. Results and Conclusions

Table 30 summarizes the protection data obtained in ferrets after challenge with a heterologous H5N1 strain.

TABLE 30

Protection of AS03-adjuvanted H5N1-vaccinated ferrets against a challenge with a heterologous H5N1 influenza virus.

| Vaccination regimen | No. dead/ total no. (% survival) | % of ferrets with viral load per gram of lung tissue | | |
|---|---|---|---|---|
| | | <$10^2$ $TCID_{50}$ | $10^2$ $TCID_{50}$ < X < $10^{5.5}$ $TCID_{50}$ | >$10^{5.5}$ $TCID_{50}$ |
| Adjuvant alone | 6/6 (0) | 0 | 0 | 100 |
| Unadjuv. H5N1 (15 μg) | 6/6 (0) | 0 | 0 | 100 |
| H5N1-AS03 (1.7 μg) | 1/6 (83) | 68 | 32 | 0 |
| H5N1-AS03 (3.8 μg) | 0/6 (100) | 50 | 50 | 0 |
| H5N1-AS03 (7.5 μg)* | 0/5 (100) | 80 | 20 | 0 |
| H5N1-AS03 (15 μg) | 0/6 (100) | 84 | 16 | 0 |

*One animal immunized with 7.5 μg HA of the adjuvanted vaccine died after challenge with A/Indonesia. However, macroscopic examination was not consistent with H5N1 infection-induced death and was not comparable with pathologic findings in control ferrets immunized with AS03 alone or the unadjuvanted vaccine. This animal was excluded from the analysis as not compliant to the protocol and not replaced by another animal.

VI.3.1. Protection Data.

Following the challenge of ferrets with H5N1/A/Indonesia/5/05, all control animals receiving adjuvant alone or non-adjuvanted H5N1/A/Vietnam/1194/04 vaccine died or were moribund and were euthanized on days 3 or 4 (Table 30). In contrast, the majority of animals immunized with adjuvanted H5N1 split vaccine survived to the end of the challenge phase on Day 5 and were protected against the lethal challenge with H5N1/A/Indonesia (Table 30). All ferrets who received two doses of at least 3.8 μg of the AS03-adjuvanted H5N1/Vietnam (Clade 1) vaccine survived the lethal heterologous challenge. Furthermore, all except one animal survived the challenge in the group of ferrets who received the lowest dose (1.7 μg) of the AS03-adjuvanted H5N1 vaccine (see Table 30).

VI.3.2. Humoral Responses (Neutralizing Antibody Titers)

Serological assessments showed that the AS03-adjuvanted monovalent H5N1 A/Vietnam/1194/04 split formulations induced a neutralizing antibody response against the homologous H5N1 A/Vietnam strain (FIG. 14A). Furthermore, AS03-adjuvanted H5N1 A/Vietnam vaccine induced neutralizing antibody responses to the heterologous clade 2 H5N1/A/Indonesia strain (FIG. 14B) while no neutralizing antibody response (<40) was observed in ferrets immunized with the the non-adjuvanted A/Vietnam vaccine or the adjuvant alone. Interestingly, 97% of ferrets immunized with the H5N1/A/Vietnam vaccine adjuvanted with AS03 that showed neutralizing antibody titers to H5N1/A/Vietnam higher than 40 were protected against a challenge with A/Indonesia (mortality or viral shedding in the lung). Moreover, all ferrets with anti-H5N1 A/Vietnam neutralizing antibody responses below 40 were not protected in terms of mortality or viral shedding in the lung.

These data demonstrate the potential of this adjuvanted H5N1 split vaccine to generate cross-reactive humoral immune responses against a heterologous H5N1 pandemic influenza strain.

VI.3.3. Viral Shedding after Challenge with Heterologous A/Indonesia/5/05 Virus

Viral load higher than $10^{5.5}$ TCID50/g of lung tissue was observed in the lungs of all ferrets immunized with the adjuvant alone or with non-adjuvanted H5N1 A/Vietnam/1194/04 vaccine (Table 30). An antigen-dose dependent decrease in viral load was observed in all ferrets immunized with adjuvanted vaccines (FIG. 15). In 70% of ferrets immunized with adjuvanted H5N1 vaccines, no virus was detected (under the limit of detection of $10^2$ $TCID_{50}$/g of lung tissue) (Table 30).

TABLE 31

Viral shedding in upper respiratory tract (throat and nasal swabs).

| Groups | % animals shedding virus | % ≥$10^2$ $TCID_{50}$/ml |
|---|---|---|
| Adjuvant alone | 100 | 83 |
| 15 µg Non-adjuvanted H5N1 | 83 | 83 |
| H5N1 AS03 (1.7 µg) | 33 | 33 |
| H5N1 AS03 (3.8 µg) | 17 | 0 |
| H5N1 AS03 (7.5 µg) | 20 | 0 |
| H5N1 AS03 (15 µg) | 33 | 33 |

As shown in Table 31, 92% ferrets immunized with the adjuvant alone or the non-adjuvanted H5N1 vaccine shed high levels of virus in the upper respiratory tract (throat or nasal swabs) throughout the course of infection. Conversely, only 17% ferrets receiving AS03-adjuvanted H5N1 vaccines shed virus in throat or nasal swabs demonstrating a reduced risk of viral transmission in ferrets receiving the AS03-adjuvanted vaccines. No ferrets immunized with 3.8 or 7.5 µg of AS03-adjuvanted showed viral shedding >$10^2$ $TCID_{50}$ in throat or nasal swabs.

Importantly, it should be noted that most animals from placebo (PBS) and adjuvant only groups died or were euthanized on days 3 and 4, while most animals in the vaccinated groups survived through to euthanasia on day 5. Consequently viral loads were not measured on the same day post challenge for all animals.

In summary, these results show the potential of a split adjuvanted pandemic vaccine, such as H5N1/A/Vietnam formulated with AS03, to induce even with as low a dose of antigen as 3.8 µg, a strong cross-protective response in ferrets against a lethal heterologous H5N1 virus from another genetic sublineage (such as A/Indonesia/5/05 virus). The ferrets in the two control groups, who received either adjuvant alone or a non-adjuvanted vaccine, were shown to be highly susceptible to H5N1 influenza infection, and did not survive challenge with the drifted strain. These data suggest that cross-protection may be mediated at least in part by antigen-induced humoral immunity.

These data support the concept of pre-pandemic vaccination, in order words the use of an adjuvanted H5N1 vaccine produced from a strain (e.g. clade* 1 H5N1A/Vietnam/1194/04) that does not optimally matched the pandemic strain (e.g. clade 2 H5N1/A/Indonesia/5/05) for a pre-pandemic strategy of vaccination. Such a pre-pandemic influenza vaccine being effective against different strains, offers the possibility to provide protection both before, and in the months following, the declaration of a pandemic.

The invention claimed is:

1. A method for immunizing a human against influenza virus infection, the method comprising:
    selecting a human who was previously vaccinated with a monovalent first vaccine composition comprising a low amount of an influenza virus haemagglutanin (HA) antigen from an influenza virus of subtype H2, H5, H6, H7 or H9, in combination with an adjuvant, wherein the low HA antigen amount does not exceed 15 µg of HA antigen per dose, and wherein said adjuvant is an oil-in-water emulsion comprising squalene and an emulsifying agent; and
    administering to the selected human a monovalent second vaccine composition comprising a low amount of an influenza virus HA antigen from a variant of the same influenza virus subtype, in combination with an adjuvant, wherein the low HA antigen amount does not exceed 15 µg of HA antigen per dose, wherein said adjuvant is an oil-in-water emulsion comprising squalene and an emulsifying agent; and wherein the variant comprises an antigenically distinct HA.

2. The method as claimed in claim 1, wherein the emulsifying agent of the first or second vaccine composition is polyoxyethylene sorbitan monooleate.

3. The method as claimed in claim 1, wherein the emulsifying agent of the first or second vaccine composition is present at an amount of 0.01 to 5.0% by weight (w/w) of the vaccine composition.

4. The method as claimed in claim 1, wherein the emulsifying agent of the first or second vaccine composition is present at an amount of 0.1 to 2.0% by weight (w/w) of the vaccine composition.

5. The method as claimed in claim 1, wherein the adjuvant of the first or second vaccine composition comprises alpha-tocopherol.

6. The method as claimed in claim 5, wherein the ratio of squalene: tocopherol is equal or less than 1 in the adjuvant of the first or second vaccine composition.

7. The method as claimed in claim 5, wherein the alpha-tocopherol is present in an amount of 1.0% to 20% of the total volume of the vaccine composition.

8. The method as claimed in claim 5, wherein the alpha-tocopherol is present in an amount of 1.0% to 5.0% of the total volume of the vaccine composition.

9. The method as claimed in claim 1, wherein the adjuvants of the first and second vaccine composition comprise alpha-tocopherol.

10. The method as claimed in claim 1, wherein the influenza virus HA antigen of the first or second vaccine composition is from an influenza virus subtype selected from the group consisting of: H5N1, H9N2, H7N7, H2N2, H7N1, H7N3, and H5N2.

11. The method as claimed in claim 1, wherein the second vaccine composition contains an influenza virus HA antigen that shares common CD4 T-cell epitopes or common B cell epitopes with the influenza virus HA antigen in the first vaccine composition.

12. The method as claimed in claim 1, wherein the amount of HA antigen in the first or second vaccine composition does not exceed 10 µg per dose.

13. The method as claimed in claim 1, wherein the amount of HA antigen in the first or second vaccine composition does not exceed 8 µg per dose.

14. The method as claimed in claim 1, wherein the amount of HA antigen in the first or second vaccine composition is between 1 and 7.5 µg per dose.

15. The method as claimed in claim 1, wherein the amount of HA antigen in the first or second vaccine composition is between 1 and 5 µg per dose.

16. The method as claimed in claim 1, wherein the influenza virus HA antigen of the first or second vaccine composition is a non-live influenza virus HA antigen.

17. The method as claimed in claim 16, wherein the non-live influenza virus HA antigen is selected from the group consisting of: a purified inactivated whole influenza virus, and a split influenza virus.

18. The method as claimed in claim 1, wherein the influenza virus HA antigen of the first or second vaccine composition is derived from cell culture or is produced in embryonic eggs.

19. The method as claimed in claim 1, wherein the variant is a drift variant.

20. The method as claimed in claim 1, wherein the influenza virus HA antigen of the first and second vaccine composition is of influenza virus subtype H5.

21. The method as claimed in claim 1, wherein the second vaccine composition is administered 6-14 months after the human was vaccinated with the first vaccine composition.

\* \* \* \* \*